United States Patent
Hyten, Jr. et al.

(10) Patent No.: US 10,568,280 B2
(45) Date of Patent: Feb. 25, 2020

(54) LOCI ASSOCIATED WITH CHARCOAL ROT DROUGHT COMPLEX TOLERANCE IN SOYBEAN

(71) Applicant: PIONEER HI-BRED INTERNATIONAL, INC., Johnston, IA (US)

(72) Inventors: David L. Hyten, Jr., Johnston, IA (US); Andrea Beth Kalvig, Waukee, IA (US); Leslie Charles Kuhlman, Lawrence, KS (US); Donald Kyle, Princeton, IL (US); Jean Liu, Johnston, IA (US); Joshua Michael Shendelman, Ankeny, IA (US); Jeffrey A. Thompson, Edwardsville, IL (US); John Bryan Woodward, Ankeny, IA (US); Ming Yang, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 0 days.

(21) Appl. No.: 15/816,780

(22) Filed: Nov. 17, 2017

(65) Prior Publication Data
US 2018/0084745 A1 Mar. 29, 2018

Related U.S. Application Data

(60) Division of application No. 14/882,655, filed on Oct. 14, 2015, now Pat. No. 9,894,857, which is a continuation-in-part of application No. 14/815,236, filed on Jul. 31, 2015.

(51) Int. Cl.
| | | |
|---|---|---|
| *A01H 5/10* | (2018.01) | |
| *A01H 1/04* | (2006.01) | |
| *C12Q 1/6895* | (2018.01) | |
| *C12N 15/82* | (2006.01) | |
| *A01H 1/02* | (2006.01) | |

(52) U.S. Cl.
CPC .............. *A01H 1/04* (2013.01); *A01H 1/02* (2013.01); *A01H 5/10* (2013.01); *C12N 15/8282* (2013.01); *C12Q 1/6895* (2013.01); *C12Q 2600/13* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | |
|---|---|---|
| 8,212,108 B2 | 7/2012 | Kyle et al. |
| 8,710,295 B2 | 4/2014 | Campbell et al. |
| 8,710,925 B2 | 4/2014 | Campbell et al. |
| 2004/0031072 A1* | 2/2004 | La Rosa ............... C07H 21/04 800/278 |
| 2008/0166699 A1 | 7/2008 | Bagley et al. |
| 2010/0275286 A1 | 10/2010 | Wu et al. |
| 2013/0227725 A1 | 8/2013 | Kyle et al. |
| 2013/0333061 A1 | 12/2013 | Wu et al. |

FOREIGN PATENT DOCUMENTS

| | | |
|---|---|---|
| WO | 1993/25067 A1 | 12/1993 |
| WO | 2012/106759 A1 | 8/2012 |

OTHER PUBLICATIONS

Baird, et al., "Microsatellites from the charcoal rot fungus (*Macrophomina phaseolina*)," Mol. Ecol. Resour., vol. 9:946-948, 2009.
Batley, et al., "SNP Applications in Plants," Association Mapping in Plants, pp. 95-102, 2007.
Fallen, et al., "Selective Genotyping for Marker Assisted Selection Strategies for Soybean Yield Improvement" Plant Genetics, vol. 2(1):95-119, 2015.
Funke, et al., "Physical mapping of a region in the soybean (*Glycine max*) genome containing duplicated sequences," Plant Molecular Biology, vol. 22:437-446, 1993.
Glycine max strain Williams 82 clone GM_WBb0124F21, with a NCBI/GenBank accession No. AC235404, selected pages, published Mar. 12, 2009.
Muchero et al., "Genetic SNP markers and legumes synteny reveal candidate genes underlying QTL for Macrophomina phaseolina resistance and maturity in cowpea [*Vigna unguiculata* (L) Walp.]," BMC Genomics, vol. 12:1-14, 2011.
Songa et al., "Screening Common Bean Accessions for Resistance to Charcoal Rot (*Macrophomina phaseolina*) in Eastern Kenya", Experimental Agriculture, vol. 33(4):459-468, 1997.
Stukely et al., "Genetically Based Resistance of Eucalyptus marginata to Phytophthora cinnamoni," Phytopathology, vol. 84:650-656, 1994.
Search Report and Invitation to Pay Additional Fees dated Jan. 15, 2016.
International Search Report and Written Opinion for International Application No. PCT/US2015/043179, dated Dec. 10, 2015.
Office Action for U.S. Appl. No. 14/815,236, dated Sep. 23, 2015.
Office Action for U.S. Appl. No. 14/843,392, dated Oct. 2, 2015.
International Search Report and Written Opinion for International Application PCT/US15/055484 dated Apr. 11, 2016.

* cited by examiner

Primary Examiner — Bratislav Stankovic

(57) ABSTRACT

The invention relates to methods and compositions for identifying soybean plants that are tolerant, have improved tolerance or are susceptible to Charcoal Rot Drought Complex. The methods use molecular genetic markers to identify, select and/or construct tolerant plants or identify and counter-select susceptible plants. Soybean plants that display tolerance or improved tolerance to Charcoal Rot Drought Complex that are generated by the methods of the invention are also a feature of the invention. This abstract is intended as a scanning tool for purposes of searching in the particular art and is not intended to be limiting of the present invention.

1 Claim, 2 Drawing Sheets
Specification includes a Sequence Listing.

```
                        SEQUENCE LISTING

<160> NUMBER OF SEQ ID NOS: 26

<210> SEQ ID NO 1
<211> LENGTH: 130
<212> TYPE: DNA
<213> ORGANISM: Glycine max

<400> SEQUENCE: 1
ctatttgccc gcaatgctat ctgcttatgt tttagcagat tattggctat ctkccatttt      60
ccatgatctg caattggtga cacttttaaa ttttaaatat atttttcgag gacttgaaat     120
gatgctttcg                                                            130

<210> SEQ ID NO 2
<211> LENGTH: 20
<212> TYPE: DNA
<213> ORGANISM: Glycine max

<400> SEQUENCE: 2
ctatttgccc gcaatgctat                                                  20

<210> SEQ ID NO 3
<211> LENGTH: 21
<212> TYPE: DNA
<213> ORGANISM: Glycine max

<400> SEQUENCE: 3
cgaaagcatc atttcaagtc c                                                21

<210> SEQ ID NO 4
<211> LENGTH: 14
<212> TYPE: DNA
<213> ORGANISM: Glycine max

<400> SEQUENCE: 4
ctatcttcca tttt                                                        14

<210> SEQ ID NO 5
<211> LENGTH: 14
<212> TYPE: DNA
<213> ORGANISM: Glycine max

<400> SEQUENCE: 5
tatctgccat tttc                                                        14

<210> SEQ ID NO 6
<211> LENGTH: 127
<212> TYPE: DNA
<213> ORGANISM: Glycine max

<400> SEQUENCE: 6
```

```
gattccggtg aattggacct cagtggacct cgctgcgacc cagcccgaat ccagcgtggt    60
cttgcggygt tgctccgcca tcggaaacct cagatcgccg gagaggcttc ttcctcactg   120
ctctcgc                                                             127
```

<210> SEQ ID NO 7
<211> LENGTH: 20
<212> TYPE: DNA
<213> ORGANISM: Glycine max

<400> SEQUENCE: 7

```
gcgagagcag tgaggaagaa                                                20
```

<210> SEQ ID NO 8
<211> LENGTH: 20
<212> TYPE: DNA
<213> ORGANISM: Glycine max

<400> SEQUENCE: 8

```
gattccggtg aattggacct                                                20
```

<210> SEQ ID NO 9
<211> LENGTH: 14
<212> TYPE: DNA
<213> ORGANISM: Glycine max

<400> SEQUENCE: 9

```
caacaccgca agac                                                      14
```

<210> SEQ ID NO 10
<211> LENGTH: 13
<212> TYPE: DNA
<213> ORGANISM: Glycine max

<400> SEQUENCE: 10

```
caacgccgca aga                                                       13
```

<210> SEQ ID NO 11
<211> LENGTH: 150
<212> TYPE: DNA
<213> ORGANISM: Glycine max

<400> SEQUENCE: 11

```
ccctcctcca ggtatttttg tgactacaaa ttagtttcaa tcaagtaaat cctcaaataa    60
atttgktctt cacattttca ttactttttt ttatcaagta aatattactt gatcaattca   120
tatcgaggct tctatattca gcatcaggga                                    150
```

<210> SEQ ID NO 12
<211> LENGTH: 21
<212> TYPE: DNA
<213> ORGANISM: Glycine max

<400> SEQUENCE: 12

```
ccctcctcca ggtattttg t                                              21
```

<210> SEQ ID NO 13
<211> LENGTH: 23
<212> TYPE: DNA
<213> ORGANISM: Glycine max

<400> SEQUENCE: 13

```
tccctgatgc tgaatataga agc                                            23
```

<210> SEQ ID NO 14
<211> LENGTH: 17
<212> TYPE: DNA
<213> ORGANISM: Glycine max

<400> SEQUENCE: 14
aatgtgaaga acaaatt                                                17

<210> SEQ ID NO 15
<211> LENGTH: 17
<212> TYPE: DNA
<213> ORGANISM: Glycine max

<400> SEQUENCE: 15
aatgtgaaga ccaaatt                                                17

<210> SEQ ID NO 16
<211> LENGTH: 140
<212> TYPE: DNA
<213> ORGANISM: Glycine max

<400> SEQUENCE: 16
cttggtgaga gtatggacgt gaggagtatc ttctcagtta agtgtatgaa tgaaggccac    60
atacatgatr gactttaaaa agaataatga catgcatgac tttataaacc atataagcgg   120
ctgtaatttg cttttgcgtg                                              140

<210> SEQ ID NO 17
<211> LENGTH: 22
<212> TYPE: DNA
<213> ORGANISM: Glycine max

<400> SEQUENCE: 17
cttggtgaga gtatggacgt ga                                           22

<210> SEQ ID NO 18
<211> LENGTH: 21
<212> TYPE: DNA
<213> ORGANISM: Glycine max

<400> SEQUENCE: 18
cacgcaaaag caaattacag c                                            21

<210> SEQ ID NO 19
<211> LENGTH: 16
<212> TYPE: DNA
<213> ORGANISM: Glycine max

<400> SEQUENCE: 19
acatgatgga ctttaa                                                  16

<210> SEQ ID NO 20
<211> LENGTH: 18
<212> TYPE: DNA
<213> ORGANISM: Glycine max

<400> SEQUENCE: 20
ccacatacat gatagact                                                18

<210> SEQ ID NO 21
<211> LENGTH: 112
<212> TYPE: DNA

<213> ORGANISM: Glycine max

<400> SEQUENCE: 21

| ggtaagggag ccaatttgt ttatattata aggaaaatgt ttataatgat gaagaattaa | 60 |
| tggactttt kataatgacg aagaatggaa ttaaacaatg ctaagacatt ca | 112 |

<210> SEQ ID NO 22
<211> LENGTH: 21
<212> TYPE: DNA
<213> ORGANISM: Glycine max

<400> SEQUENCE: 22

| ggtaagggag ccaatttgt t | 21 |

<210> SEQ ID NO 23
<211> LENGTH: 26
<212> TYPE: DNA
<213> ORGANISM: Glycine max

<400> SEQUENCE: 23

| tgaatgtctt agcattgttt aattcc | 26 |

<210> SEQ ID NO 24
<211> LENGTH: 18
<212> TYPE: DNA
<213> ORGANISM: Glycine max

<400> SEQUENCE: 24

| ttcttcgtca ttataaaa | 18 |

<210> SEQ ID NO 25
<211> LENGTH: 10001
<212> TYPE: DNA
<213> ORGANISM: Glycine max

<400> SEQUENCE: 25

| ttgttaaact gtgcttttgg ttctgagagt tctttccctt cataggggac aacaaggtat | 60 |
| ggtaataaac gatagcctga atctccaatt atatattctc ttatttctga tccttcagag | 120 |
| agctgtaata tgcttccatt caatctctca cccttctcac aaagtttatt gaaatttgaa | 180 |
| ctctcaaata tcatccagtc ctccatttta cccggccaac cagtgactat gtccctgaac | 240 |
| ctcatgtccg gatccactat tgcttgcaag accatgctat gatttttctt gtgatcaagc | 300 |
| cacacattac aggaaggttc agatgcaggt aaacacattg tgatgtgagt agcatcaatt | 360 |
| acaccacagc aattaggcaa gccgtgtatt ttctcaaatt tggatttgat tgcattcatt | 420 |
| tccacttctg ttgaaggcca tcgcaggtgg tgaagacccc tttcttccat ggattcaaca | 480 |
| aatcgccagg tgacttgtga aacagtcgag tggtttaggc caaatgaatc accaattgtg | 540 |
| accagtgact caccagatcc cagtcttctc agtgccactg ctacttgttc acataaagat | 600 |
| attggcttgc gatttgtaaa cacaaaatgt gcagctttca tcatcatatc atccttaaca | 660 |
| agtgaacata tgtactcaaa tgtctttctg gagatcttga aaacagattc gaaattatcc | 720 |
| aagcactttg atggagactg ctgaagacct gccaagtaac atgagttata tcttctaatt | 780 |
| ctaaatgtta ataatgcagg cttttcagat atttttaca aggtctttca ggtcatgcag | 840 |
| gattgaaatg ccaaggcatg gcgaattccc ttcactatgc ctaaaaagaa aagggttagg | 900 |
| ggaaggatgt aatgctaagt gagaaaaatc acaagccttc gatttgtttg tgaaatcagt | 960 |
| gagattccta tgataagagg aacaaaaaca catcaatgaa aatgaaaacg ctatacatta | 1020 |

```
tgtcttgatt cacgagggaa gaggccagac aaacagctcc tgaattaatc atactaaact    1080
aattaagaag gacataactt atttattgta tagttaagca aataaagctt aacacagaaa    1140
tttataaaaa aagtaattta cttcagtata tataaaaaaa ctgatgcatt ccagttgaac    1200
acagaaataa cataaaaata gttatcacag cagccagttt ctgcaaagtc atagtatcat    1260
gtacagcagc tgatgctact ttccaaatgt cagttgtttt ggcgatttca gttcaagaag    1320
aaactaatta cttgaaaaac tgataggttt cccaaagttc tttgaaatgt tgcaattatg    1380
tctttaagca atcactcaaa acgtaacatt ggttgaaaga aattataagc tttgccaatt    1440
aaatgccggt gttgacatta gcaggtaagg agcatagatt gaactaaata ccaactaatt    1500
ctactttata aaaatgtga tcttgtttct gcaaatggtt tgattaaatt cccccatatg    1560
atcacacatc acaaaggtac accatttcaa aactatacag aggatgaaca tatatagttt    1620
gtgcaagagt gtggtactaa aagatcataa ttcataaaca taacatagac aaggtaaaat    1680
ttataagcaa atatcaagct tgtaaacaga ccccccccc ccaaaaaaaa aaaaaaaaca    1740
attcaccaag ctcaacatct tcaaactaac cgatcaaatc atggctgtaa aactagatac    1800
agaaataaat aaaaaattct ctataaaggt taggaatagg aacacatttc atgcatactt    1860
tctttgacta atagaagata caatgaagat aaaaagtctg ctctgttatt tttcctgcat    1920
aacccacatc cccatttttt ttttttattt tcatttagtt tcttcgactc agtgaatcta    1980
atagactatg cttgccaact gaggcaccag gctgcaataa tcaggcttc aattaatcac    2040 ttgagtagaa cagcaaaata agacaatgag caggctaaaa agctttagga cccaaaacac    2100
tgaatttgaa gtattatgtc aattacatta aattgttgaa actttctaat agaatctgta    2160
aaaaaacatg ttcacaacta acaaaattca ggtcccttct ttataagcag gaggtctagt    2220
gaatggaaag cagaactgca ataaagcatt acacaaaata tattgtgcac gaactacaac    2280
tggtatgaag ggaatacaaa catatctaat acatgtgtta cacatgcttg ctttttattta   2340 cttaaaaat caaaattaca aaaaattagc atgaaaagtc agaaaactct ggaaatatga    2400
agcctaatac cacaccagac ataaaacagg aagcaaaaga cagactacgt gcatatttgg    2460
acacgcatcc aatacacact tatattgaaa aaaacaggtt aaattaggtc aattaagcat    2520
aagttataac ctattgcttc tgatggatgt gctggaaatc cttgaagatg tggaaacaaa    2580
cagactgtac aaccattcca gcaccaagaa gaaagtacca tttttccttg gaatttctca    2640
tacacacata atgtactaca tgaatacaca aacttgttca gggttaatta tatgctacta    2700
tataatgtga ttaagcattc cttgattggt aagataagat aacacgatag gaatgacaaa    2760
caacttgaaa gtcaaattag ggatccttac atatacatat accaaaatgc atttgaacga    2820
cacagtgtgc aaataatttc aatgacaaaa cagttatttt gcaaaataga gatgagaacc    2880
aaggcattca gcaaagcagg tcaggattca ttagcaaaaa gcaacatcac acataaaaaa    2940
gcgaatagca aacatgaaag gaattattga acacggtaaa agacagaaag aaatctacca    3000
ttcattctct ttgacaagtc atcccaccaa tctacaggac catctccctc gggtgaccca    3060
gaagcagcag cagaaccatt cttgtcatgc ttcttctctg ctttctttt cttcttgaat    3120 cctctcacag gacccatcac aagtcaatcg gggaggcaaa gtctgcaaca attcacgggg   3180
tcaagagaaa acaaaaccaa aaaaaaaaga ttcattacta tcaccataga gcaataacac    3240
tcaccagaga atgatggtgg tgcaacaag ttatgagaat aggagtaaat aatggttagt    3300
tgcaaagcaa agagtggtgt atgagtgttt gtttaaagca tgcaagaaag gagtgaaaag    3360
```

```
ggaagagaga ggacataaaa gaaggaagta tcctaaggtt aaggttaagg taaggtaact    3420
aatgcaaaat ccaagcaaca ccaacacatg tgggttggtt taagacaatg tgtcaacaca    3480
gacatagata tgaatatgat atatatgggg tgcagagaaa gagcatcaat caccaattca    3540
ccatgtctat gcctgattca cttcgtgctt tcccacagaa aaatttatga gtaaaatgct    3600
gccttggttt ggttatcgtc ataaaaatta aaataataa aaaaagcgac ttctctccct     3660
cgatttgaaa actaagtgca taacaaaaaa aaaaaaaaaa ctagcataaa aatgaacata    3720
tgtcattgaa tgattattca aaagacaaaa aaaatatca attaggattg aagagacaat     3780
tcacaatata tattgtaaat tcttttttt atcgaaatca aagatagta tcaataaatt      3840
tataataatc catacacctt ctttaatcaa ttatattaga tcaatatata ttacaaaata    3900
aataatatat ttcttgataa tataaatatt tcatttacgt tggttgtagt ataagtctaa    3960
gcctaagtaa agtcccatat gagtagaagt aaaaaaattg agcaccatat aaataaggaa    4020
aaaacttata aacttcaatt ttaatttagg tgattgatta aatattgata cttttttcta    4080
tctatacttt ttttaatccc ctaactattt aatcacaaat aattaacttt tataataata    4140
atttttaatt aatgatagat ttattaacat ttataataat catcttctaa tttatttcaa    4200
taataatttc ggattggtga agagtatgaa gttttatgc taatactgta tgtttgtttg    4260
actcataata atatttaaat ttttaaaaga attaacaata ttattgtaac ggagagaaaa    4320
aatggtaagt tggtctgggt ttaatgtttt aaatattaat attttgcat tgaacacata     4380
cttaatacag caataattct tttaacttta ggggtgcggt tatcttctaa atgcgattcc    4440
gcccattgga ttataatatt aaaggccaag ctcacttgta atattaaata atctgttgac    4500
tagtttggtt tatctcataa aaatatatat taaattattt taaggattta ggttatatcc    4560
atagacaaca taaatttcat ttaccacgtc aatcaatcac aaaacatcat gtttctaaaa    4620
aaaattttaa gtttcatgct aattatctta aaaagcacac atatcatgta ttataattga    4680
ttataaatgt aaaataaaat tatactaaca atatataata attaaactct taggtataat    4740
ttaactacaa ataaaaaata tagttaaatt atttcttaaa agagtatgga cagaaaaaag    4800
ttttaccttc agaacattga ttagtcgtta aaattctaaa aaattgttgt ttgtaaaaaa    4860
caaaataaat ttttttggtgt aaactgttca cattaatcat taaaattaca attattaatc   4920
atttagtttt taaattaagg atttttcaat ttaaatttaa atttcgataa taataagtca    4980
ttttagtttta taacttttat gtgtattaga caatttgatc cctaaaataa gtatcaaatt   5040
aattgatgat tgtcaaactt atatatatat atatgaaatt gtaaatacta attactttag    5100
tttttaatat ttaaaaagt gaattaatta attttataat ttaagaatct aaattaatta    5160
ttgaagttaa tttttatgtat taaattgatt aatagctgtt aaattttgaa attaatttca   5220
tgcttctgta ttattaggaa ttaaataaat tgatatttat aattttaaga attaatttga    5280
tatgttacag acattctttt ttagattatc ggaggtttta tttatatgta tttcaaacta    5340
cttgtcttta tacttataac gatgagtaac catgtagacc ccttttttcat tcaagtcttg   5400
tcaaattaag gttgatgatt tgatgcgatc agttttttcca gaggcaaacg tggtattgga   5460
aggctgattg catgttgtat ttataatttc agtacagcac ctttagcatt tttgccttgc    5520
gttgttatat acggaacatt gcatagcaga aggaactaga ataatatttt cacttgaatt    5580
tttttttaaa ttaagataat ttaaaaaaat aatcatttca ctaaaaataa agtaaaatca    5640
acacacatgc aaggatacct tttattgtt attattaaaa taatagtgat atgtctttta     5700
tatttctaat gaagtcttct cttttgatca accacgtttt ttttatatat ttaaatttaa    5760
```

```
aattgaaatc ttgtactttt atatttaatt atttattttc aattgtagtt agtagttaca    5820
cgtattgatt caatcagaat tagtacattg tatttatttt caactgtagt tacatatggt    5880
cacatagttt ttttttttgt cttttacaa aatctaatgt tttcaaaatc ttaactattg     5940
```
*Note: line 5940 — best reading*

```
aatattttc tcctaaatta tttcaaccat gaaaatattt cgaatattta tatattttt     6000 gcaattaatg tttctaacat ttatcaccaa tattgataag attttatat tatttttta    6060 aaaaacttat tattatttat aaatttaact taaactaaat actataaatt tttgtattta    6120
tatataatta taaattctaa attaaataat aaaatcatgt tatcaaagct tttgtaattt    6180
atatttccat tttagtgcaa aaataaaagg ttaaatcatt tgaattcata tcgccatttt    6240 attttagaa tataagttga agaaaaaata tttatatatt ataacagatt tatattatct    6300
ttgtaaaaat agttatttta tttttatat ttgtcatttt tttcattctt agagtttgac    6360
tctaacacta tcttcctaat actttcttta tgatccgcta gtatttatta tagatcatca    6420 attttgtgg attacatttt ttatttattc accaaaatta ataattttta ataaaatata    6480
atcaatcata taacaagtgt tagaaagaaa gtgtcactga tattttctt ttctaaaatt    6540 atatgcgatt agaattgcaa ttttggtctt taataatac ctaaatggta tttgatttaa    6600
tttaaaaaat ggctatgata aatttaagtg attatcttaa cttattttat atagaaattt    6660
tttgttataa atggtttatt ttgaacaaaa gtatttaat attattaaaa ctatttactt    6720
tatttatttt atatactcta attttaaatc aaaacaagtc ccggccgatc tataacaata    6780
acaatatgag tattattatg gttattatta tttatttaat actcttaaat aatttataaa    6840
aatagttatg tttgtaaaat gcctaatgat tattatatac attttattg atattgtcat    6900 tattattact attattttca ttattaatat tctgttagtg aaaaataaaa taatttatta    6960
attggtataa ttggtgaatt tttatagtta ataaatatga ttcttatttc ttaatatttt    7020
ttatgtttac gtatcttaaa taaacaaatt aagtgaacaa tcttttgata acttatttac    7080
actgcggaaa tatatttatc cacaatatttt tttcaatgta catgtatctt ataaaaatag    7140
taaataacta tttgataatt tgtttacaaa ttttatttaa taagaatggc ttatatgttt    7200
gtaagggaat tttatcacaa tatttaaaa ttggggtgtt caaatgtttc agtcacaatt    7260
catttctcaa actaacttaa ttatattgga ttaagttttt tactcaaact aacttaatta    7320
cattggatta acttttttaa gtgttcagat caaaattgac ctaattaaat taagatctaa    7380
ttataaatga gtcatgtaat aggttttatt ttttttatc tacctcaatc catagcatat    7440
aattatattt attactatat ataaattaat tattaaataa aaaacattaa ttttagttt    7500 ttatagttta ttaaattatt aaattagacc actcataatt tttcttttct ttttaagttt    7560
tttttatctt tgtattgatt ttgtttgtgt tttctcatat taatataata tttatttct    7620 attaaaaata aaactatgat gttagcatta aaatcattaa ttttactagt caaataatat    7680
tatcacaatt tgatttcttt taagtacatt aatcattata ttttacaaaa ttttagacaa    7740
aaataaatta ttattctaaa aaaatcatgt tttacaaaag aaatttattg tttcaaagat    7800
tcatatgagt tgagtgtata aaaaaatatt acacaaaccc aacacaaccc ataaaatttta    7860 gtcaaatccc tattttaaaa acatgtcgtg cttataaatc atgctaacaa ccaaattgaa    7920
gtccaaatgt acaaaagacc aggttgtatt catttgactg aactactgaa ggatggtgtc    7980
taacaaaaac acatgtttaa ggaagattat ggattataat gtatagtttg atctggcaaa    8040
tttgatcatt caggttaaag aaaaaatgta tgtgtagagt aaaatttgc tatgattta     8100
```

```
ttcctagtaa agaacatctt agtttaaaaa ttcattcttc aacaaaacac ttagtttagc      8160
attttactac atggaaaaga gtttaataag gttgaaatca cctaggaaga aaataaagaa      8220
ttgaaaatgc tataaaagac atggaaaaga gcattttgcg acgcaggtaa gggagccaat      8280
tttgttata ttataaggaa aatgtttata atgatgaaga attaatggac ttttttataa       8340
tgacgaagaa tggaattaaa caatgctaag acattcagaa aaattacaca cacacacaca      8400
gattccagat gaattgaggc ttcgcatgaa agctattcat gtagacattc agcttctat       8460
atgtgtagac gaatgtccaa acttatcatg atataacgtt cgatttaata cccttatgtc      8520
agcatggctg ggtagtagta acgtcgctta caatttatct atttgtatcc ttcactttt       8580
tatgttataa ttatatgtcg aatttctttt tgctgcatat ttattacaac atcgtcattt      8640
aaataaatgg tctgcttatc tgatgcaagt tgtcaatacc cttttcaatg ttttgtcgca      8700
gaaaacaaca aatcatttga tattcagaca tgggccataa tcaaagccca aggactgtcc      8760
ttttgttatc gtcttttgtc atttggattt tggaccgact atgctgtcct tagaccatag      8820
tcccaatcaa gactgcaact tcctgctcct ccaagttgct ttttgaaccc cctttatggc      8880
ttccagactg gccaatctga aatgtaaatt taaattccga aatgcacccg ttttttagc      8940
tttcagaaga taaaaatatt tcaaaagggg tgcaggaagc aacaaccct aatcaaatat      9000
acagatcgca tagcaatcat attagggttc cgaactagtg agcacaccac aatactttgg      9060
atcacccaaa acaaaaaaa caaaaaatc ccacaggtaa cacctgacca gaatactgtg        9120
tgcctaattg ctaaatgtac tcggttactg ctaaatatat tatttctctc ttttataaaa      9180
caactacttt aatattttcg tttcttcttt ttacttgttc aagcacctct ttcttctatc      9240
ttcctttcaa tcaaaaagtt tgaatctatt agattcaatc tttctatgtt catgtacatt      9300
ttttattgtt ttaattttatc caacttgaga gtttatagct atcctacagt ctaccataca     9360
tatatattct tgcattagat ggtctaatta gagggcgagc cttggtgcag cggtaaagtt      9420
gtgccttggt aacttgttga tcatgggttc gaatctggaa acaacctctt tgcatatgca      9480
aggataaggc tgcgtacaat atccctcccc catactttcg catagcgaag agcaggacac      9540
tgatcattt ctctcaatcc atcaaggtct tttgtggctt agattcttca ttattttcca      9600
agagcatttg attgtcaaga catgaattta gataatcttg catctatttc tgagacttt       9660
atacatttt gtgatgaaa ggattattaa gtggagcaaa aacggaactg ctatactatg        9720
agctgtgatt atttcagtat attgtgcaga ctgtaggata gctataaact tggtgagagt      9780
atggacgtga ggagtatctt ctcagttaag tgtatgaatg aaggccacat acatgataga      9840
ctttaaaaag aataatgaca tgcatgactt tataaaccat ataagcggct gtaatttgct      9900
tttgcgtgat cactgatcag tgatcaccaa agtgcaagtg cttcgtcacc gcaacagtcc      9960
ccacatggta tagctctcca accaaatccc tcctatgtga g                        10001
```

<210> SEQ ID NO 26
<211> LENGTH: 40001
<212> TYPE: DNA
<213> ORGANISM: Glycine max

<400> SEQUENCE: 26

```
tctggttagt agaagagaga aaggaccgta accataaccc attttactta cttagagcgc       60
aatagtgtga actgcgaagt gaaggattct gcaaatgcaa actttagatt agtttaaacc      120
tcccacactc tagcagaagc agaaagctta aaccctacta catcaacagg cattgcgcca      180
acgccaagcc tcaactctca cgtcagggta atgtgagatt actaactcca ctgcaaatgc      240
```

```
caactttaaa cctccctctg acacactctt gaaactaaag cttaaaccct actacataca    300
ttgcgccaac gccaaacctc aactctcacg atagattatt tttaaaacta acatcatatt    360
gtttctcaca gttcgttttg tttcttaggg tctatttagt gttgtgatat tcacttataa    420
ttttttaaag agtgtatcaa aatcaagtga tatttaatta agattttttaa taacttcaaa   480
aatactttttg atatttaaaa atacaaatct tttttttctc tcattactca taattttttac  540
ttatcaacat ccagcataag aatccccggg tattgagata cacattaatc gattttaaaa    600
cttgcaggaa cgaaaaagtt taactagctt ccatggtcaa tagaatcttt ttattgctgg    660
accacagtaa aaccctatgc atatgtttat ttgtttcatt cccttgttgg taatcagtct    720
gtagcacatt ccttaagtat aatatatatt acttttgtct tctgtgtgta catgtgtatt    780
cctcttttca agtagttttt tcttttcttt tctgatgtgc gtgtgttcag tggaagtaga    840
tgcaatttgt tttcttgttc tataactgca tgtcactaac aaatggatca tggtggtcta    900
cctaatcagc atttaatcaa aacaatgaag agtgagaagt caatatatga aaggatatct    960
gctataaact tttcttaaat ggttggacct ccaggcatag agcaatataa aagcttcagt   1020
ttcctttgta agagttgtat accgtcatcc catagaatgc taagttacat gtattgatgg   1080
aatatctttg taattactct gcaaatattt tctaggctac ggtatcttaa gatgagttgt   1140
ctccttgata tactttccta tattagtttta ttttgtttcc ttgattagcc ctgcaattta   1200
tgaaaatatt cttggtttac aaggatatct ttgtatatat acacacacgg ctttgtccaa   1260
attcaataac agataatcat tccaaaaaac tctaacatgc cacaaaaaaa tattagaaaa   1320
ggatgactga ctgttaatac ataacctagc atgagagagg ctgtatggtt taacaaggca   1380
tcccatgaga ctgcatcaca gattcaccaa aattcctttg gggaaacacc gacccaaatc   1440
caattcaatg catacagcaa aaatagagac aaatgcaaat aaggaaataa aaacgaggaa   1500
attgggttaa agagggtaaa gttaaaacct ggcatttcat cagagctatc ctcattagag   1560
gttgctggca aggtcaagta ccttcgagat tcttatcagc catggggttc ttgcttgtgg   1620
ttatttcagt taatttcata gtctcgtgca acaaagtttc ccccagcttt tgactatcca   1680
cttttttcact tagcaatact tgcacatcac ttgcagcatt tttctccaca gaattctcac   1740
aaaacgtcat ctgatcatgt tgcacaaaag atctgcttcc atgagaactt tgatccatga   1800
aactatatttt gccagacact ttatcatcaa tgaaggagct ctgcacacta cttgaagcag   1860
aagtatcagt ttgtggagtc ctctcaggag ctgttctcat ccgagggtct aaaaagggat   1920
tttgggtaca ggcatcagaa gctacaggtt ttgtaaaagt tgtgcgaacc ttaaggtttt   1980
ctcccctgca agccacagat tggtctatgg aatccattaa atataatttt taaggcttgt   2040
ggaggtatgg tccccctatgc attaaagcaa actctccatt tgtacagttc ctcaacactg   2100
tacttgcttc caaaccttcc atttcatgtt gaccaaaaca ttcatctttt ggccgactag   2160
taacttgtaa aagactgtca ctgccagctg aaggggcag tttcccatgc actatattag    2220
catgattgct aacttcagat tcataattct tctggtgttc cttttcttct tcatcagcta   2280
gcattgtttt taaatccagc ttgttcaact cgataggatc gctttcgcct catcaagtcc   2340
cgcaaagagc agttaaccat aaaaagagaa tcaacttcta aaacattgga gtactcgtac   2400
ggaggaaggg gatgcaagag ggagagggag gcgaaatttt ttaaaagagg gactagggga   2460
aagagtgaga gttttagaaa ttaaaaaaat gtgtgaaatt agcaaagccc aacttacgta   2520
tctaagggca attgcttcct gcaatagaac actcaaatga acaaaaatat cctttctttc   2580
```

```
taaaaattga ctactttcag attgtacatt ctagaattgt gcatacataa ttccataatg      2640
gacaataaaa aagcattctt tttttttgt gtgtgtctat tatagattct ccaatttgaa       2700
attataacca gatctagaaa aaaaaaaacc ttggaattta cttcttcgac gcatagcaat      2760
gattcatgga gggaaattat ggttttggag gttttcagac agaggaaaag ggagcaatta      2820
tggtacgatg gagcaaaagg gaggaaacgg tggtagcata gaggggaacc ttgggatatt      2880
tgaaaataag gaggtgcagg tagcaaaaca atagggtgga agaagcaact gttgtatcaa      2940
tctagatggt attgatgtgg gtggccgaaa tgataaaata ccactgaaaa attaattaat      3000
taattaatta atcaattaaa ttattaattt taattctttt ttagtttttt tctttttataa     3060 taaccaatgt acaatttttt gtccttcatt tttcactcga gtttagtcca atttctcgta      3120
ttatttgtaa tcaagtactt ctgattgtac ctaaaaaaaa taattctgat tgttttacat      3180
aaaatcttca taaattcgaa aatttgaggg tttgtggcat atctgagata gaaaataatt      3240
taaaaggttt caaagttaga aattttgatg attcaattag ggtttaaaaa aggtaaacat      3300
ttgaaatttt caaattttag aagaaatata tcattttgaa ttagtaagat ttgagtagaa      3360
gagcctagag ataaaaatga tacattagtc ataataaata gatcaaaggt gtaattaaag      3420
attaaatatt atatatatat atatatatat atatatatat atatatataa gaaaatttta      3480
aaatttaggg gggaaggagg ggaaatgccc cccttcaaaa tatatgtagc tcctgtttcc      3540
tatcccacct aagttcctct aaaaattcag aaagaacatc acttttacca tcaacttgca      3600
tgattctctt taacgaatca gttgcccttt ttcagcccct ttctgacgac attctagtta      3660
ctcagcgtct agcatattat atggatacag tgttgctact ttcttttttgc gtttagtata      3720 agatatggat ccagctcaat aaagctatta catgaattaa taaccttttcc ctaaagttta     3780 tactttatac tatgatcact cattatatcg ttcagatgat ttatgtccat tacctgtcaa      3840
agcatcaaaa aacaagatca aactcataaa tcattatacg ggtggagatc agatccctgc      3900
actttaaaaa caaactggag aggatcatga tccaagggcc atttcagttt tatttcaatt      3960
attttccata ttattaacca ataccaaaag cataaaaaaa cacaagaaag atggcatcac      4020
gcattaaaca tagtacactc aacgaccaat agagaatgcc cccttttcaa aaccaattga      4080
cagtagttca actggtacta actgattcac accagttcat acacttaacc aggataaata      4140
agtttcccag acctaagctg gcctgattat ccagtcaggt tcagttttag aaacactggt      4200
tttaaccaag aaatttcaat atctcaataa aggaaaagga aaatcctta aaaagtatat       4260 ggaagagttt attagactgt aacctttagt ttttctacaa ggagagtttg aattaatata      4320
acaaatatag cacaatcatc tatctaaatt actaaaatat ctcaagtaca ttggttaaaa      4380
attcttctta ccaaacactt taaaaaaata attccaaaat ccaaacacaa aaagtagctc      4440
caaactagag catacaagag caatcagctc aaaaatgtca aggttttttt ttttcccta      4500 caagtatctt ctcatgcata gttgctcctt agtgtatcat ctcacaccct tcagcaattt      4560
tgaaaatgta aaacagcaaa aataaataac atacaacatg tgggctttag ctggcgagaa      4620
ctacatatgg tacgagcttc agcttcttga ctaatacaat gtgtgagcaa tatgaagtag      4680
agatactatc tgcaagcgtg aatgttggcc agtaaaatcc agtgatcact ttcaccaacc      4740
atgatgtcca tgaccaagtc catatgcatc catataatta gctccatgga tgtgtgcatc      4800
accatagtga tcatgtccgt gaccatgatc atgactgtga tggtgatggt gatcatgacc      4860
actgcttttt gcttcatcaa gcatcttctg tatgtgctct gggatggact cttgctcaac      4920
tttcctaaca gactttggta atgacaagac aaattgagaa atttttcag ctatctcaac       4980
```

```
tgctgcatcc tcctgagatc acaacaattg gattagtttc aacaacaaat gaataacatt      5040
gacatcagat gttaagttac atgaataaac agtgagtgaa cagaatatga aaataatcag      5100
gaggtggagg caagatttct cggctttcat ttattgcatc ttcaagcaaa gccaaaaaca      5160
aagttcatta gctcaacaat atatttctcc ccatccctca gatatcctac tcgaacattc      5220
tcttcccaaa ggaaccagag catcattcct ccttgaaatg agaatgaatt atgaatctat      5280
tgaggagaaa gaattgctag atctggccat attcaattcc acaagataag aaacagttat      5340
attcaagata aaaatttgag ggagaaaagg ttatgttgtc attatgaatt tgatgttacg      5400
attagttatc taccatagga ggaacttgaa aaatgaaggt cttcccaata attacttcat      5460
tagtaaagaa tgtctgttgg tataagaggg tttttttttt tttttggta gagtatgtat      5520 aagaggtttg cattggcaga ctagtttaag ttgaagcata tggttcacgc ttcacacaag      5580
attaggaaag acccacaaaa acaaataatt tatgcatagg gtaacacaaa atacactaaa      5640
ttgtttatta actaatcatg gtagttgact ctctatgttc atcactcttt ctctgccttc      5700
actaacaaac cttatcaaag ggggactact ttacaactga gtttgactga ctagggacca      5760
taacctcatg ctttgcacca gatcagaaaa acccacataa actgaaacca aggtgtatag      5820
acacattgaa aagttagcat ctatattcga tggcagcttg gatacttgaa aaaattcaat      5880
caaagtacag caagcaagag ttttcaagaa agtttagatc aacataacat accatagtca      5940
caactcacaa catcacaaaa tctaatacta ccaaaattag ttagcctccg atagcagtaa      6000
gaaaccagct cattcagcaa ggctaaatta ttagtctaat gtaaagtgta aaacacccaa      6060
tttgaatttc attccaccat ccatttcaat ctgatcaaac aatctctcca tgacaacaaa      6120
aatacaaaaa agcaagcaat aacaaatctt gatctcacct gagcccaccg gcctccagta      6180
tgtgtaacaa aactagcctg tggaagtgca tccgcaaccc ggtgaccctc ctggctccat      6240
tcctcggacc acccagcaga ccacatcacc tgcattggca tccctttcaa cccctcaccc      6300
cactcttcca agccaaagct agaattcacc ctcttcccaa cattcacaac cgccctcctc      6360
ccatctcttc ccttcaacaa ggccctcgac gcctctgaat cggcgacacc aaccctcttg      6420
gaacagcaca aagccaccac cttagcaaaa acaaaagaaa ccccccaacac cacctccctc      6480 accacaggca cctccagagc ccaaacggga aaagccccct tagtagacga cgccgtatcg      6540
ataagcgtca cgctcctcac caactcaggc ctctcagaaa caaaattagc actcaacccc      6600
aatgcggaat cgtgcagaac caagtgaaca ggtgcaagcc ccatggaatc aataacttcc      6660
cccaacacct tccccatctc ttgtggaccc aaatcaatag gctttcttgt ttttctcttc      6720
gacatacgag cttgaatttc ctcgtacgga atttgacccg tttccaccat ctgatcaaac      6780
gcccagaaaa gacccctctc ttgaatctcg ctgtaaacgt accaaaacct cccaaaaacc      6840
ccgtttacgc cctcgacgga agcctcgacg gacttgtcgg agaagccgtg tccggggagg      6900
tcgagggagg tgacgtggag tccgttggcg gcgagggatt gggcaaggtg gcggtaggag      6960
tatgagctga gaccctggcc gtggagaatg attatgtttt cggacgatgt gggaccctct      7020
tggagggtga agacttggat gggggcttcg ttggaatgtg tttggacctt gatggtgcgg      7080
ccgttggagt agtggtggcg gaggggggga ggagggtga ggaaccaggt cttggggtct      7140 tgggggggaga ggctggaggt caagacaaag aagagagtga ggaggagac ggagagggtg      7200 aagtagaacc agaaggagaa ggggttgttg ttgctgttgg ggggtggaga agaagggggtt      7260 ttgagtttgg gtttgcgggg ttttgggatc tgtgagtgtg agtctgcttc tgcttctggt      7320
```

```
tcttctgtga tgatagccat gccaactagt cactgctccc agcttcgctg tggctcaaag    7380
actaaaaacc agcttttta cgctgtgaca gcatcattgc gtgagtaatg gggcggtagt    7440
gttagtctgt gttatggttc ttttttttat ttataatttt ttctattctt ttaaaagaa    7500 aaaaatgaaa attaatatat aacataagc aatactcatt atatgaaaaa gtaggaagta    7560
ataaaatgtt aaatatattt tatattttca ataaattaaa tatacttatt ttgtttgagt    7620
attattcttt acaaaataat tagaatatgt gtaagattat ttttttata aaaaaaactt    7680 atgattctct ctagatttt tctataagga ggaatttcat ttctctgatt tttttgtttt    7740
tatctttggt gtttgtaaat tcaagtggct aaaatgttag tattaacaac tattaacaag    7800
ctaaaaaaaa tataagaaaa tttatataca tgatcatttt ttgaggattt agtgtgtgtt    7860
tgttctatag gtgaatttgt tgtcacaata aatgtaatgt gatttcattg taaaatatg    7920 ttttttttt gttacttatg agaacataag ttgaatcacc gtaataacaa ttcaaacacg    7980
ctcttaatcg tatataagta tattactttt gagagaaaaa atactgaaga tgttaattta    8040 gattttgca acatgaaatc atatcaaata ttttgattca agtagtaaca agtttcattt    8100
ttcttaagta atgagtcaaa ttcatgtttt ttaaataaaa gaaacatgt actaaaattc    8160 ctaattgatt cgccaaactt gttcctaggt caaaatttca agtgttttg aaaaccaaaa    8220 atcttaagaa aaacacaagg taaatcctta aataaatcta ctaaaattac atgcatatta    8280
attattattt ttaactcttt ttcacaaaat tagtttatta aatattttg ttacattatt    8340 aattttgaa tgaaattata atctcaaatg tttaatttat tacaaaaata tttataggaa    8400
atttaaaaaa ttcttcatac atattttat aaaggattaa aacaatgaca acaaaaaatt    8460 ttaaatttt ttaacaaat tcaatgataa attaatttt aaaaataaaa tttttgttga    8520
taaataatag attaaattaa ttttttattc ctttaattta ttttttaaaa ttaaattaa    8580 ttctttaatt ttttaaatta atttaatttg attattcaat ctaaattgta agaatcacat    8640
tttatgatag ttcaaaatag tcacaaaata tacatttttc aaaaaagaa tcaatttaaa    8700 aaaaataaag aattgaatta aaaaaataaa aatcaaattg aattaatttt aaaagttaaa    8760
aattcaaatt aaaaaaaact aaaaaatcaa attaaaccca aataataaat taaaagaaaa    8820
aaaaaactaa tttaacccaa atattagtaa agattgaaag tttgagatgg gagcagatgg    8880
cataggcacg cacggatgag cacatataaa acgaaggag aaggttatcg cgtgagtgag    8940
attcgaaaag caattgccaa ctacaatgca gcgtggcctc cttgcttcct ctcttccact    9000
ctcaacccgc tctctcttcc ttcctctccc tctatgcctc tcaagcccaa acccattctt    9060
ctacaaactc aattcccata gtaagccttt cttcaccatt cgcaattgca gcagctcctt    9120
caaagtgaaa ccctcttccc aaatcaaaaa aatccgcgcc gaagccgagc ttgaccccaa    9180
gctcaccgcg ctccgaaacc tcttctccaa acccggagta acattgacg cttacgtcat    9240 cccttcccaa gacgctcacc aggtttagtt tcttcaaca tctctatcaa tctaagtgtt    9300
tatagtttat acatactaat ttgaatttga atttggtgtt agagcgagtt cattgccgag    9360
tgttactcta ggagagccta catatcgggt tttactggca gtgctggaac tgctgtggtt    9420
actaaggaca aagctgctct ctggacagat ggcagatatt ttctccaggt ttgctttgat    9480
cttcatccag cacgaatcgt atcgtatcta tttcatgatt tattttctac tatcgctggt    9540
tgtaggcgga gaagcagctg agctctaatt ggattctgat gcgggcggga aatccaggag    9600
tccctaccgc tagcgaatgg ctcaacgatg ttttggctcc aggtggcaga gttggtattg    9660
atcccgtgag ttttcatcgc ccatttatta ttgcgtgttt agaaacatat agtagagtca    9720
```

```
catactaggt gaaaactcta actaccgtat tagcttctag ttaaacatga aaaatcacgt    9780
cagctgcgtg caaccaaaca cgccattaat ttatgttgca agctgattcc ctaacttcct    9840
attttttgat tccttggcca gtcagggcac tagttaggat gacccaaaga taaatgattg    9900
caatagactc tccaatacac tcttttgaat ccactctttt caattgattg aaatttatgt    9960
gaaatcacaa gattttgtgg gtcccccccat cttaattaat gaacctacct tataatctgg   10020
tagtttccaa taaattttaa ccaataataa agaattccct gaaatattat tttctatttt   10080
tattacaaga gaagtgttag caactcattc ttttgaacac actttctact gttaactaaa   10140
tttattggaa ataacaattt tgttgggtct cactttcat ttaatgtctc tctctcttga    10200
ttttttagtt ttcaacaaat tacaaattgt tcttttttg agtctgccta cctttttgg     10260
tctctgtgcc tgatacaatg ttctcttcca tattgttaag gaggcagttt ctttttactt   10320
cggatgctgc agaggaactt aaggggtta tctctaagaa caaccatgag ctcgtatatt    10380
tgtacaattc aaatcttgtg gatgaaatat ggaaagaatc taggccaaaa cctccaaata   10440
atccagtaag agtgcacaac ttaaagtacg ctggtttgga cgtggcatca aaattatcat   10500
ctttgaggtc agaacttgtc aatgctggct catctgcaat tgtcatctcc atgcttgatg   10560
aaattgcatg gttgttgaac ttggtaatct atctttagtt ctttacacct tttctttgat   10620
atactgatgt ttttgtatat actatcacat gtccgtgtaa gttgtaaacc ttcttttcaaa  10680
atcttattta agttgcttgg gtctaacata agtaaattat tggttccttt ttcccactgt   10740
tctttgctaa tgtttctttc agtgtgtgag taactttttgg cttttttcttt tgaagagagg  10800
cagtgatatt ccacattcac cggttgtgta tgcatacttg attgtggagg ttagtggagc   10860
aaaattattt atagatgatt ccaaagttac cgaagaggtg agtgatcact tgaagaaagc   10920
agatacagag atcaggccgt acaattcagt tatatctgaa atcgaaaggt aataatggaa   10980
atccattttt ttatgccact cccatttttt gcctagtttt actagaaatg tctaataata   11040
ttatagtaga caggccaagg tgactttcta aagtagtagc ttacattctg ccattgttta   11100
tgcttacttt gtaaaagcag catggttttg ggaaactgag cttgattttc ttttcaggt    11160
tggcagcacg aggtgcttcc ctttggttgg atacttcatc agttaatgct gctattgtga   11220
atgcctacag agctgcctgt gacagatatt atcagaactg tgaaaataaa cacaaaacca   11280
ggacaaatgg ttttgatgga tcctcagacg tacccttttc tgttcacaaa gtctctcctg   11340
tttctcaagc gaaggccata aaaaatgaat cagagttaga aggaatgcga aattgtcatt   11400
taaggttacc atatttacc tttgtgatga ttattgttga tggttttgt atgttttgat     11460
ttttgtattt taatgatctt tttcaaattg gagttctaca gtctacatat atggagacaa   11520
tagaatgtcc tagacaggct atgtactgtt tcagttatta aaaaaatggt ctgtagttt    11580
gaaaaagagt ttcagtagtt ctacatatat ttaacagtag aatgttaaat atgtataaga   11640
gtcacacaga agcttgcttt cagcacattt atatatacat tgtgctatct tattgtttcc   11700
agggatgcag ctgcacttgc tcagttctgg gattggctag agacagaaat tactaaggat   11760
aggatattaa cagaagtaga agtttcagat aaacttcttg agtttcgctc aaaacaagct   11820
ggtttcctag atactagctt tgacacaata agtggtactg tggtagactg acaattatt    11880
ttaatatttt ccattgaatt atggttaaat aaacatggaa agatactgcc ataattttc    11940
cacagaattg ttttaactgc caattatttt aggggaaaatt accaaaaaca cttcctgatt  12000
cctactataa atatggagta tgaaggatca cccttagta ttcctatgta acagaatatg    12060
```

```
gtaattctat gaaaatatgt tgctattatt cctccatcac tccatggtac ttatgtttac   12120
cattagttcc atttagtatt tttatttctc ttcttaggct tcaattcaat tcctctttgt   12180
ttttggctat aatttgttca tttcattggt tcaggttctg gtccaaatgg cgctatcata   12240
cactacaaac cagaaccaga gagttgtagt tctgtggatg ccaataaact gttcttattg   12300
gatagtggtg ctcaatatgt tgatggcaca actgacataa cacgcacagt tcattttggc   12360
aagcctacag caagagagaa ggaatgcttt acccgagttt gcaggtacc ttgcttttat    12420 actttttcc tgggtcgatt tctgcatttg attcatggga gtgtccttca caattcttca    12480
atctaggtta atatgtcaat tatacaaatt catgtgttta ttttcaagta tatgtataat   12540
ggctgtgtta ttaatgttta acatcccagt cctgctaatt tgaccttctt aaataattgt   12600
ttgtctaaac ccatatattt aattgcaggg ccatatagct cttgatcagt cagtcttttcc  12660 agaaaatacc cctggttttg tgctggatgc gtttgcccga tcctttctt ggaaagttgg    12720 acttgactac aggcatggta tattcctact tcaaatggag ggctgttata tattttctta   12780
aaaccaaatg gatttattga ttgattgaac aattgtgctt aattgctatc tgttcaggga   12840
ctggacacgg tgtaggagct gcattaaatg ttcatgaagg cccgcaaagt attagtcatc   12900
gttatggaaa tttgacccct ctagtgaagg gcatgattgt tagcaacgag cctggctatt   12960
atgaagacca tgccttcggt attcggattg aggtgatatt ctcttcagct atcttatgct   13020
ctgaaatgat aactttagct cctagtgttg ctgtatggat tggatcatca ttcaattaat   13080
tttattaggt gttgttaata ctcgtattaa ttttatctcc tttacaaagc tcatcctttta  13140 cacctaatgt aagttgaaat atgtgagagt aattcaagaa gtattctgaa tttgtaatga   13200
gagaggctgc cttttgagat cttttgaagc ttgattgcta ttttccagat ttccttactg   13260
gttaataagt tgcagtttca atttcatgga tggattgcaa aaccttccat caatcatgag   13320
tgtcttaaga ggcttgctgt ggattacttg attcatgatt tttctatatt taaatattct   13380
tgccatctct tattaatgaa cagaaatgcc agggtaccat cctacactat gccatttccc   13440 cttttctct ctgcttaact gttaaaataa cattttctca gtcttatctt ctggcttgca    13500
tgatgatgac actctttag cttgcagaat ctcctgtatg taagaaatgc tgagacacca   13560
aatcgttttg ggggtatcga atacctagga tttgaaaaac ttacatatgt acccattcag   13620
gtatgttgtt gcctgttggt cgttcttacc atttgttgct gaagttgata gttttctttt    13680 cttctttt ttagttgata ttgatgaaag ataaaacacc tgttgtagac ttgtagttca     13740
acatcaggag attgaggatt ttttaattgc aagagacagt taaatagctt attctcccat   13800
aaatttggat ctaattatat ttctctactg atgtagtagt ggcaagtcct ttctttaag    13860 agttgatatg cgaccgacag aggtccttga ggcctatttg atagtggaca atccagtgtt   13920
tttagtcaat caattatgaa actttataga atattaatcc tattcctata aaactcaagc   13980
attaagcata ggtaaaatac tagtcagatt ttttctttt ttctttctgg atcagcacta    14040
atcagaaatt ataaataatc tattttctcc atacctgcat tgctgaaagt atccttggga   14100
aatttatcat taattagaat tggttgttca ttccgttctg aatgcttgtt tatattttaa   14160
atcagtgttg ttaaatagca gctatagtgc tattgcattg cggaatttct tggatccgca   14220
attgcgactc cgtcttctat tgcagtcatg gttgcgacat acatttggca tcctcttgtc   14280
atctccaaca actctccatc caattgaacc gagttaatat tatgtttatt tttatttgca   14340
tacaacttaa ttttttacgt gcgtgcgggc gcgcacacac acgtacatat atatatcaac   14400
tgctatgcga ctttcgctat ttgcccgcaa tgctatctgc ttatgtttta gcagattatt   14460
```

```
ggctatcttc cattttccat gatctgcaat tggtgacact tttaaatttt aaatatattt    14520
ttcgaggact tgaaatgatg ctttcgtttt tcattaggtc tatctcattt tcacctgaac    14580
tttaaagcat tctattctga gccaagtacc cttttgagca cttgcttact aacctgggaa    14640
tatcttgcag attaaattgg ttgatttgtc tctgctatcg gctgcagaga ttgattggct    14700
gaacaactat cactcactag tctgggaaaa ggtattttgc tttggctctt ttaggtacat    14760
tggattttcc ttctggtgtg ttcaatggct ttcttttttct tcttgttttg ttcttctttg    14820
gattctcctc agttcctttt tccctgtcta ttatgcaaat gcatgctctc tgcaaggcca    14880
tatgtaccat ggctttgctt ttgtaattgc cgttctgatc cttagtcttg ggtttcttta    14940
aatatacatt ttgatgccac tgcaactcag caatttaaga atgctaaaaa gtcatggagc    15000
atccttgtgt ttatgtctat cttatcagat caccctctct ctttggcatg tccacggaat    15060
ggaaccaccc cttcccccett ctataagaat ctaaagtcct gcattgtgca atctattttg    15120
tagtcttgta tagttgattg tcttgtaact actatgatac ctcacaggtt tcaccgttga    15180
tggatggctc tgctcgccaa tggctttgga acaacactcg gcctatcatc catgagaaaa    15240
tttaatattt ttcatgttaa tgtgctatgg tactcgaggt tcacattttg gcgtgctgcc    15300
tcctcgtcta ttttgtctat actctagctt atctccataa tttatatagg agacgctgtg    15360
aaatgtgaat aaaatagtga gttgggatta catgaatttg atcataggat ctttggctgg    15420
gcaaatgaac atttagccat tagcaccctt ttaagtatgc ttacttgtga tattcaatat    15480
aattttttta actgttgtca aagtttacac tctcaactgt gaatcataga agttatataa    15540
aaaataatga taaagcctcc aatttcttgc tttccatggt atcaattata tatgatatat    15600
ataatagaaa taaaatgaag actctccaga caccagcaca ctcgcgcaca ctgaattgat    15660
gcttatttat tatggaccct aatgatgtca agaaacttt tgacgttcaa actcaattac     15720
tgctctgcca aaaacatgtg cgggaatcta taccaaaaat attgtaatgt ggtttctctt    15780
ggtggcatgc accggcccgg catttgggcc ttttcaatat aaaaatttgt tactatgata    15840
ctatcattag atttgtaact taacttttgg tgtcacgtac cttatggtta tcagattatg    15900
attcttttcg gactaaagtt aaactttatg tttacggacc ctattaccaa cgaaaaaatt    15960
atgacccaac ttgtatcaaa attgctactc taaaaaatca tacattttag acctgagttt    16020
ttaagaaata ctctaaccat aaaattccat tgtgtgaat ggggatgatg acaacaatca     16080
gtttaaaaat aaaagaaaa atgatttat catttaatgg ctgcaatgta gtatagactc       16140
tagtgaagga tatttgtgtt cttaaaaaaa aatcttatca tactttgaaa ttttttgctaa    16200 ttgttaatta aagaaagtaa atttaattat ggcatgcatt tcatgggcc ataaaaaaga      16260 acacactagt tactgaacaa tgtaatattt caaaatcaaa gaaatgaagc aatgactctc    16320
ctaaagaaag tattccgtaa taataactta aatatttact gacctcaagt atggaatcat    16380
tggacatttc ggcagaagaa ataaattata gaaattaaaa attgaaatga tagattatct    16440
gcatttatct ttgtgtacta ccgttgtcct tgcttatttc attaattgta cacataacaa    16500
tgatagacca ttacagtact tttcaaagtt gtccttcttt attccattaa ttgtaaacat    16560
aacaatgata aacattata atatattta gggataaaag tctctcaaaa agaatctgag      16620
tttcatatca ttgtggctag atgtagagcc tttcttccta atcctacaaa ttccatggtg    16680
agttttgaga ggagacaaac taataatatt gctcatacac taacaaagac atcattattt    16740
aacgcttgta acaagtcttc tgacaatatt catacttgta tcaaaacttt gatttggaat    16800
```

```
gaaaagtcct aattatattt cctataaaaa aaatgatcaa aatgtctctt acattttgga   16860
aatctattac atgcgttaga agaaaaaact tagagggaat ttttttgttct aacgaaacta  16920 aatatataca aagtttaaaa tagaacaata agtttataaa tttcgtgata actatcttta  16980
aagtgttacc aataattatt ttgattagtt gacggtgaac aaaaacttta ctataaccgt   17040
agttgagaat taaattcaaa ttaaaagact aaattctatt tttttattaaa aaaatacccg  17100 tatacatttt tttaattgat aaatttttgga ccaaccacaa cttgtacctt tgttttgttt  17160
atatataaag atgactaatt ctatataagt gagattaatt aatattaaat attataataa  17220
attatcaaaa ttaaatataa aagtaataat tttgaaataa attatataat tttaacaaat  17280
ctttaatctt aataattcat cgtgtgtgtt gttatataat taatttttg tgattctcta   17340 tcctctttc attgtgcaca ctattttga ttattttctg aaaataaaac tgacattttg    17400
ttagagaatt gcttcatagt atttctcaat tattatatga attccaaaga agaaaaaact  17460
cgaagaatta gagagaggtc aagtcaataa taataatgat gagttgaaca aagggtgaaa  17520
actgaaaagg aaattgaagt ataacaccaa attaaccaac gagtccaaaa aaccaaacaa  17580
ttaacaaaac ggccccaaaa ataactttta ttatattcgc aagtcaccca aaatttgaaa  17640
agtgatgttc gcgacccctt ttccctttttc cctctattct ctcccttttg ttgtatttgt  17700
atagttcagt tctttctgtg gttgccgacg caacgtctct cgcactcgca tcgctctcac  17760
agaatcacta ccaatgcaag acattttcgg atcagtcgc cgatcactgg tattccgcgg   17820
ttcgccggag aacgaagaat cctctcttgg agtcggagga agcctcgtcg ataggatcag  17880
ttattgtatc cgaagttcca gagtcttctc caaaccctcg acgccgtcgc cgccctcctt  17940
tcctaaggac gctgctcctc cgatccgatg gcggaaaggc gagttgatcg gttgcggcgc  18000 cttttggccaa gtctacgttg gaatgaatct cgattctgga gagcttctgg cggttaaaca  18060
ggtcaattac tttctgagtt cttttcttcgc ttcatcgtta atttccactt tctaattta   18120 tcgtcatttc gatttttttt tttaatttcc ttttggagtt cggttttag cttttgtttg    18180 tttctccttt tcgcttgatt cttcggaatt gatttcgctg tagcatgtttt tcttttattt  18240 gaactaattg tgattttagc tttattgctt aaattgattt cgttttcttg tctgtgtttt  18300
taggtcttga ttgcggcaag taatgctacg aaggagaagg cacaggttcg ttgtttgatt  18360
aagttctatt tgcaactact gctgattgca tctactaaag caattcgatg ccagtcaatt  18420
gttgtgactt ataggtgttt gattgtgcct tttgctgtta gttgtttcaa tttatttta   18480 actaaaggca tcgcacttgc tttgttatat atagttttt catctgaaat atcaaggtta   18540
ctgcaaaact tgaaggtggg ggaagtaaat ccgtaattta tgctttaaac tagggattgt  18600
ctttgagtga tgagaaaaca gttcctttc acataattat gtaaatgctt tgtttatttg   18660
ttcttaaaca tggcatgatt cagattttgg gctgttatta tgagattttc attgaattag  18720
cgtagttctt atgtggctgt ttgattaatg ttgtcatacc accaacaggc tcacataaaa  18780
gagcttgagg aagaagttaa attactgaaa gacctttcac atccgaacat tgttgtgagt  18840
atgatatttt attggtctaa gatactccaa gtcaattagt tcacccggac tatctcttga  18900
ctgaatagtt tttatgctg tagagatatt tgggtacggt cagagaagag gacaccctaa   18960
atattctcct ggagtttgtt cctggtggat ccatatcatc actattgggg aagtttgggg  19020 ctttcccctga ggctgtaagt tttagttacc gagccactat acttttgtaa ttttatatgc  19080
caaatcagtt tcactaattc attcaacagg taataagaac ttacacaaag cagctactac  19140
ttggacttga gtacttgcac aaaaatggaa tcatgcacag agacattaag gtgaatttta  19200
```

```
tttcattgat atgcatgcta tcttggttct ttactggcag ctgatgttca agtttttatt   19260
aatttcaggg ggccaatatt cttgtagata ataaaggatg cataaaactt gcagactttg   19320
gggcatccaa acaagttgtt gagctggtaa tctcagtctt atctatagct ctactactgt   19380
gtatgttgct tgacctttgt gagggctttt ctgtttgcaa atttgtttaa gcagtgtttt   19440 ttttttttt tataaataat ccaggcaacc atttctggtg ccaagtccat gaaaggtact    19500
ccatattgga tggctccaga agttattctc cagactgggc attgcttgta aggacattaa   19560
ccatctactc tatagacata ttttacttac aatgtgctgc tctattttta atattctttg   19620
acatgattaa aaaactggat gtttcttctg gtcagatatc acttggtatt gtagttgtga   19680
ttgactgttt atgattctac gtgttgacca ttctgtgcaa aagttttgta tatctagagt   19740
tgtgttagaa ctgcctgcct taattataca atgatggttt ctgttagaaa ttagaaatat   19800
ttgcttggga tatcgaaagt tagttgcagg aattttcagc aagacacatg ggctaactat   19860 gcttttaaa gtttctggtc ccaagcaatt tgaatcggag tatcattgct tgcatgttag    19920
tttcattctc tagcagagat agttatatgt tttatatgaa tgacatgtac aaattcaagg   19980
tcaagggttc taccttttcaa attttattag gagattctta tatactgttc ttgtggcatt   20040
gcttgagttt tattttgttt attttttttgt gcttgtgtat aatatctttt ggtaatgatg   20100
tttcatttga agccaaataa agatgttttc atatattgac gccttttcag ctctgctgac   20160
atatggagtg tgggttgtac tgtgattgag atggccactg gaaagcctcc ctggagtcag   20220
caataccaac aagaggtatc tcttattctg actccttaaa ttctgttaga ggttctctct   20280
ggacatctac taaaaaagtg aactttcagg ttgctgctct cttccatata gggacaacta   20340
agtctcatcc gccaatccct gatcatctat cagctgcagc aaaagatttt ctgctaaaat   20400
gtttgcagaa gtatgttact tttaattttc tcctgctttg cttgtatcac aattcacaaa   20460
ttcctaattt tagtgtgttt cattgtgtca attatgtttt gaagtatatg atggaagatt   20520
gatcatgcta aacattattg agttttttctt tttggtggtt ggagtggggg caggaagggg   20580
gttgggggag aaagattcct cagcacattt ctatactgtc aactatttgt caaaaaagag   20640
gagtttaatg ttcaagttgt gtcacttgtg tgtgtgtgtg tgcgtgtgcg agtgtgtgtg   20700
tgtgtgtgtg agagagagag agagataatg tatgccttgt atgctttctt ttcaaatgtt   20760
cattatcaga tcacaaaagt cacatataaa aatataatcc ttttgtaggg aaccaatttt   20820
gaggtcatcg gcatccaaac tgctgcaggt gattctatga gcttttttctc tctagactgc   20880 gcatatgaaa tatataacat tttgagtggc cattactagt agtagtattt ttcatgaaat   20940
atttcagttc tccctaagat tttaattttt tactgcagca tcccttttgtt actggtgaac   21000 atatgaattc tcttcctctg tcatctaatg tcatggtatg taaaattgaa gtgatattta   21060
aaattctgtt ctatgtatct tttataaacc aattttttaag aaaaaaaatc actttcactt   21120
ctgacaggaa aatttggaag cttcttcacc atcatgtgcc ccaaatgcgg aatccttgta   21180
agtgttaaac attggcagtt atttcggtgg aacacttaaa gagctatatt ttttatgcta   21240
gtgaatggta atatgatatt gtttaacaaa cttttgtgat ttatgtagcc tttgctgttc   21300
aacggtaaat cctctggact tgggaattaa acagtcatgg ggaatgagca acgatgatga   21360
tatgtgtgtg attgatgaca aagaagagtt ctcacagagt gatgccaaat acaaatcatt   21420
tatgtcaact aatatcgagg tgattgcatt caagcccttta ttgttttatt taatattaaa   21480
ttaatgagtt ctcagaaaca ttttttttaa tgtagagttt caacccaatg tctgatccct   21540
```

```
ctgatgattg ggggggggtgt aaatttgatg caagtccaga actggaaaat agaggggtta    21600
attttggcac tgatgaaagt tacgtgccac ctgatcagtc aggggatgat gataagggc      21660 agaaagattt ttcctttcca ggtgtgccat ctctgtcaga ggaagatgat gaactcacag     21720
agtcaaaaat taaagcattt ttggatgaga aggtattggc ttctagttga aattgagtta    21780
gtcgttttgc tgtaacttga ccaatatttt tgtctcctaa ctgccgtgtt ataatgatga    21840
ttatgcattt atgacaggct cttgaactga aaaaattgca gacacctta tatgaagagt     21900 tttacaatag tttaaataca tcttgttctc ccaatgtgat tgagagcacc agtgatgata   21960
ctgcttgtcg aaaatatttg aaattacctc ctaaaagcag gtcaccaagt cgggtaccaa    22020
ttagtactcc gtctaaagcc gttgataatt ctggaagtcc tggaagtaat ggccggtcat    22080
catcaactgt tggccatgta aataaccata gtccacagga tattccagca tcttcccta   22140 atgaatggaa aggactgata gctgactctc agcagcagcc cagtagccca aggttggttt    22200 gttttgcct tgctttgctt ttctaagcat cgattatttt cagaaatata aagtaattga     22260
agaactatat gttgtacttg cagtctaagc ttttctgaga gacagaggaa gtggaaagaa    22320
gagctcgatc aggagcttga gagaaagcga ggttagaagt ctcttctaag taaaatgtct    22380
aagaagttcc tgtaattcct aattttgcaa ctgtcattaa ttttggtcct tagctttggc   22440
atgcattagt taatttgatc cttgacctgg tacgtgtcag tcaatttaat cgctattatc    22500
aggtactaaa tcaattgatg atcgttaaat ttaagtatca aattgactgt ttagtgtcaa    22560
tttcaagaat ttcataaacc agggatcaaa ttgaccgatg attctcattt taaggatcaa    22620
atcactttct tttaacttgt ttttttgctt atctagagta gcactaaatt tgactattta    22680
atgtaagcga gaggcatgag gagagactcc aaagtggtca ctttggtgca taattgaaaa    22740 atacttttaga tgatcgaaac ataatatgct agctgaattt gtataattaa tttatttact   22800
agttgcttgg gcacaaacgt tgcagaaatg atgcggcagg ctggcatggg cggaaagaca    22860
tcttcaccga aggatcgagc tttaaatcgg cagagggaga aaacaagatt tgcttctccc    22920
agtaaataag agagactcgt tagagcattc atcctgcgtt aactactggg attgcaaaca    22980
cgtgttactg cagttttgtt ggggtcgtta atgttatata ttcatccaat ttggccgttt    23040
tgccatatga aaaatctcat gcttatcttg tccgtgttgt tgtgccatgt aaagcttttt    23100
atacatgcat tgcttgaaat ttttttttact ttcctttggg gttttgagag atgcatggcg   23160
tcaactttat gcccttctg tattatgaaa atacaaataa tcagaactat gtggcgcaag     23220
attgcctatg aatctgttgc cacttgtttc tcttttcccc ctgctaattg tttctcaatg    23280
gtaatttgtg gtctgatttg ttactcctac agtatggaat taatcctcttg aatatagcaa   23340 acttaaaata tgatagcatt agaactataa tctagaattg ttaatttcaa cttttttttt    23400
ttatatagaa acaaagttga ttaagtcatt tttctatgag cggcacaaaa gaaaattaaa    23460
attttattgg aggacattag ctatgatgtg attagatatg acagaaact atggtggtga     23520 aagacatcgg gacatttgca atgggagttt cttaactatc agtttaattc aaataagaat    23580
tttgtactac tggagaacaa ctatgtgaga gtgagactca tttatgggtt tgccaacaga    23640
aacaattagt tctctctcaa atgtgggtt atcttcttc atgcaatagt ttcacgttgc     23700
tttcacatta tattgcaatt tgacattta tacaagaaag tttcaattg acatcttttt      23760 gaaggagttt ttaacgtaca tacagtgaaa aacaatataa ttaacgatta aaattttaat    23820
ttataaaata atttacattt cgataaccct ttcaattttt cttgttgtgt ttcgtttatt    23880
tgttttctta atttataaac aaaaataatt cattattaaa ctgtcgcaag gagagaataa    23940
```

```
aattatacac tcaacgtgaa gcagtaaaaa agatgtagac catagaaaag gatctatttt   24000
gggagaacaa gacttggatc ctctctagcc caactctctt caatctcgat atctttattt   24060
aggtcaaatg ttttaatttc gattaaactt actttaata tccaaacttc aactttgatc   24120
aatttaattt taaacttaac tttaaaaaca gtggttattg tcccttctca agaagaaaat   24180
cgtctgtaag aaaagacaaa aatgactatt ttctaaaatc cttagactaa attaatccaa   24240
attaaagtag aagaattaac acaaattttt atcaaaagta caaagactaa aaatatgttt   24300
aattcttttt atttttttca tcatctgtcc tcatttctcc attcactctc tccttgcttt   24360
tgttttttta gctgtagaga caagacatgg gagtcgggag aggatctatt ttgagaaaac   24420
aagactttgg ataatttctg atacaattct ctctagtctc tctatctccc tatttttttc   24480
tccatcatct accttcattt gtccactctc tctctaattt ttggctacat aaaggatcta   24540
ttttgagaga ataggttttc gatcctcccc ataacacaac tctctctatg ggttagggga   24600
gttacacgat tggaataaga tgtgaaagtt gcctattgat agttaaccaa tccattacct   24660 tttttggta aaccaatcca ttaactgcat aattaaaaaa aagtattttt tatccattgt   24720
aaagtaaaaa aaaaaaatc attttactg gcctatatac catttgggta aaaaatcata   24780
ttttctacta gtaaaaaaaa atgcaagtta aaccatgagt ttaggggcga aattaagctt   24840
atttaaacat gagtttatgt ttattcaaca tgtatgttta taaataagt aaaaaaacca   24900 acacgtataa aaaaaaggat attcacacaa acactctcta ggagctagca ttattttta   24960 agttagaagc ttatttacta ctctaaaaag ataataaaaa cccttcaaac tcttgagaat   25020
taagatatta ttgacctcat caaagcttaa aaaaaaaaag agagtagcat gtcactttgc   25080
tgggcgttgt ttcaatccac ttactaaccc atcgctttgc tgtgcccttt tcctgctctt   25140
caatggtgaa acaaatcttg ttgccagcct tgaaggagag aaagatcgac atagttttga   25200
tgcaactgat ctctttggag aacacttcct caaatttact accccatcac ttttttgcac   25260
agttttcttg ctctttattg gtgaagctaa taatcttgtt gccactctag gagagaaagt   25320
tcgaacccat ctctttgttg gagaactctt cttgctcaaa ctcaaacttg tatttgtagg   25380
tcttgtgggt gaagaagaaa taaacataat tgatgggttt tttactttga cttgaacttt   25440
ggaagctgct gaaggtgggg acatgatcaa acacttttgt tgtgttccta tgtttcttga   25500
tatgacatga gattttgtct tgcaaaatag ttgttgcctt gaagaatgtg tagacaagaa   25560
taaaggtttg gggacaagca ctgtcttgtt agtactactg ctagcacatg ccctatttgg   25620
caaacacttg ttattattct cttttgtcaaa ctctactgtt cttttggag gagaaacctt   25680 gaagttaatc cttgaacgag cccattgaga tggtggggta tcagaaagtg gtttaatttg   25740
cttctctttc ctccttctag cattgagttg tgtgttttca gtgtcaactt tctggtttga   25800
ccgttgggac tgtggagttt ttggttcctt ggtggcagtt ttcctactaa ctgctgagac   25860
tatttcgctg gcaaattgac ttgcctttaa aatttctcca acagtttcgc caacaagcat   25920
tgaaggcagt gacatttgcc tccattcttt acctgaataa agattacatt tgcaagtgaa   25980
ggggtaaaat agatgaattg ccctttgtt tttacagata aaataatgaa tcattgtaca   26040
ttatggtcga ttcaaagtg aagtaactaa tttgggta taccggtgcg acaataaaaa   26100
taaccgtagg atatattaaa aaaatattga atgactgaga tttaagaaag gacactggat   26160
gagcaagcta ttttgataca ttatttttt tataaaatat tattttttt ctttttcttt   26220 ttctatcttc cagctttacc ctaaccattc ttctgctgct agcaatggca caagacccaa   26280
```

```
catcaaattt cattcagatt tccaaaccaa attctaaaac ttaattcatt ctaaatttta    26340
tattttaaac aaattacaca ttatcaatct cacaacaaaa acattacgcc cctatgttgt    26400
tgaaagaacc caacgttaac gaagacatgg ctgccaccga ttgaagccct tcaagagatc    26460
aaagaagata gaaaaaaaca aaaaaaaata attattttta tttttttaatg atttaatata    26520 attctttttt tcttacggtt ttaaatccac tactggtcgt ttcagggta cacgggtgag    26580 ggagggagag aattttggac ttcaccctag aagccaccgt acattatatt aactaatgta    26640
gtccatgaaa agtaaactga ctttattttt gacaaaaaga ctacttcatg gctaagagta    26700
taactgtata aaaagagag agaggtaaca agaccttctg aatttgttgg cttaggaaac    26760
ttccccggtg gagatcttct tggtgcatca tgcttgatcc ttcaaaacat gtttatgttt    26820
atgaacaata gtatagttac aagtagtaag atatttatac tcttaatcaa taaaaaaaca    26880
ttcatcatgt gattttaaaa ataattatta tgaaagttta ataccatact taataatact    26940
caacgaaaaa ttattggata atttgagacc gtcgtagttt caactcatct ttgtatcaca    27000
catgttatta attttttta ttgaaaaact taaatacatg ttacataaaa attgacagag    27060
acaataataa tttctcatat ctaacaccat acttaacaat gtttaattgg gtgacaattt    27120
catctattct aatcaaattt cattttttat aaactaatct taaaattcaa atagaatgta    27180
accaaaacca aaatttacct gactgattct tgcttgcacc ttagactggt tcgcagataa    27240
cctctggtgc tgcgagggct gagacttacc cctgagacaa ccttatttcc accggccacc    27300
gtgtactgaa gttcttgtaa tcgaaccatg cactgatcca ccttcaaggg cccacaacaa    27360
ttcactgtca gggaaactcg gattaaaaat ataaggttta attacttatt agttctttat    27420
atttacacta tctttacata tagttatact taaaaactac tcattttact tctacacata    27480
ttttttttaa tctgtttaag tccttgccat ttaaaattgt catataaaat tatataaatt    27540
aaaatggatt aaaaagtgta tatataagaa ataaaacaag acaaaaaata catgcatgta    27600
tagagattaa aacgagtggt ttttaaagat aagaagtaaa tcgtaaaaat tgagtaatta    27660
aaccttaaaa taaacaaaaa gcaaacaaag aaaggagtgg tgcagggtgg ggatctaatt    27720
ctaatttatg aagtgtcatt agagaaaatt agtaatgtat tttagttacc ttgttgagtg    27780
tttctctgat tagagaacga ttgagaacag ctaacatttt gttatgcttt ggtgggcttc    27840
tagcaaccat ctttgggaag tgggtctcaa aatttgaaac tcactcggat aactcagaat    27900
ctgaatttca gacctcaaaa cttgttcttc cagattccat agtttggctc cgaagtgtga    27960
gaattcaaac taaacggtcc cctcctttgc aacgtgttag actatccaca ggaaacggta    28020
acgattatta ttgaaccgtt ctgttttctt tttaaaaata acaaatcgcg ttactgtttt    28080
caactcaacg cttttatttg gaaaaacaaa aaaatccaa aaacttaaaa aaatcgttat    28140
aatctactta ttcattgaat acatttcttt ttaaagtcgt taaattacaa taattgatca    28200
ttcaaattat aaaaattaca acagcaaaaa atagttttaa aaactggcac catggatcat    28260
ttcaattctt aacgttagag attcttaagc ttttacatgt tttcagaaat caaattaatt    28320
aataattatt attataaaaa taattaataa ttatcaaatt tagaaattaa taatcattat    28380
aaattccagg aacaaaatca attgattga caatgttaca aattaaattt accaatgaga    28440
ctaatttcaa gaaccatttt ttttttttatg attgtcaaag ttaaagacta acttttcctt    28500
ttcttttaat atcacagatc aaattgattg gtgatactaa ttaaaatgac taaacccact    28560
aaagtaatgt tttactctta aaattttgcg tgtatacaag taatccattg ttttaataat    28620
aaatgaaata ttgagaggtt ttatgataaa atggctaata gaaaccaagt cctggattca    28680
```

```
tatttcctta aaaaatgtct catatttaaa cttttttcaat ggaaaaaaat atgattaaaa    28740
aattattaag taatcaatca agcttttttcg acaaaaatta attattaata aaactaatag    28800
gcatgcacac ctatatcatg gtaaaattga tcaattaaat tttgaagttg tctctttgac    28860
gctagtccgt gaacagccga ccgtcctatt gtaaaaattg gagcctctta aaaaatctac    28920
taaattcatc aaattgtttt aaaggatcaa aacggcccgt tttggctctc tgtaaaatat    28980
tcgtttgggc gggggcaaat aaccaaccaa ttggtggaaa cgttgttatg gagggtgcca    29040
aaatggaaaa attgaatgga gtacctgtgc tagttttatt ttacgggttc aagagatgct    29100
tggcatttaa atctgcacga atgaaaaaaa aaaagcttga acttgtgaca aacagaaat     29160 ttgattgaac aagtattaga agtataatga acaatggata ttaaacgaaa ataatttcaa    29220
tttataaaac caacagtagt aagacagact atcaaaattg aacttttttt ttccacttct    29280
aaggaattaa tttattagtt ccttgcattt gggtggatgg ccgagatggc aagagtgatg    29340
aaatctgcta ttttttcagc cattttttcct atgtttttaga aaacaaagat catagcattt   29400
cagtagaaag gccgagatgg tataaccaat gactttctgc tgctattttt caagcccttc    29460
agcttgagag gagtccacac taagggtttg cgtctttgat gcctaggct gccggcaaac     29520 ttactgctgc tcctcatcaa agttggtgat gctgtctcga ctgaggttat agcttctggc    29580
aatggggcaa acaaccttga atactgagtt tcccttttggt tccttttcgg tgattgctga   29640
gtggggaaac cgagtggagt tctgacagga caaagtgtag ctacagaaac acgcctcctt    29700
ctaggctgaa gggcctgtga tgctgatggt ggggtgggg gtcttacagc tatggatacc     29760
ctccttcttg gtttcataag gtcttgtgtg ttaattgaag ttgttctggc aatgttttcc    29820
tgtccatcca tggaagagct gcatgagggc cttctcggtg attgctgagt ggggaacgg     29880 agtggagttc tgacaggaca tagtgtagct acagaaacac gcctccttct aggctgaagg    29940
gtccgtgatg ttgatggtgt ggttgggggt cttacagcta tggatacccc ccttcttggt    30000
ttcacaaggt cttgtgtgtt aattgaagtt gttctagcaa tgttttcctg ttcatccatg    30060
gaagagctgc atgagggctt tctctctggt ggtggaggta aaatgttagt aattcttcta    30120
agtggcagtc ttggatcgag cggtggcttc ttcatgattt tccgagcagc tattgactcc    30180
gacattgttg aaggttgagc tgaaactgct gcaagtgatt tactttcttg tttcagtctc    30240
atttttctct cctctgtcac ctggttctca agatcccgaa cctttgaaaa ttcaacgata    30300
ccttcggtga gttatatttc caaaatgaat gcattaataa tagcatctaa ataaaaagag    30360
acaagtgtaa aggtttgtgc cttctcttga agatttcggc acatgagttc tcttgtagta    30420
agtctcattt gcattgcctg caagttatct tgtaattttc tagtttcctt ctcatcatgt    30480
ttgaccttct ctacctattt gtgatcaaat tcccagattt aagaattaaa aatcagattt    30540
attaaacaaa gcttctcttg ttcttaataa tagcacaatt agactctagc ataccatttg    30600
cttgtactta ttcagttcag taaggtccgt ttgcttgcgg gctgggccac tctcaattcc    30660
tcgtacacgt gtggcaaaat tcagagaaca aagtgtctct gttaagtctg ctgcacctgg    30720
acttatctgg acaaacatta atgttttgca atcacctcct gcatttcaaa ttttcaatcc    30780
cagatcaaca tcataaataa tgaaaaaaaa agaagagaaa atgcactcac caacagacct    30840
tttaaataat aaaatagcta cgaagttgca atctaatgaa tgcttttttaa tccaagacat    30900 aacaacatca cttataaaga gcgcttgaat taaaatgtaa ataaaacaat tgaggagcat    30960
caggctgtga aatgaatcct cacctaaaga gctctggagt atatgggtga gctttgagtt    31020
```

```
cctatttgaa aaagaaaaag aaaaagaaaa agaaaactag tgagaaaaag aatgattatg   31080
tagaggatat tatatgttga gagatgagag aattacctgt aaggtatgtg ggctgatttg   31140
gatgcaagag ctgaaataac atcaccaagt gctgatagag acttgtttat gaattgagat   31200
tccttcagtc tttctccttc agcttcagtt ttccccacac gttcactgcc agctaaatct   31260
actagccaaa ggtgactcct tgttttctgg ccattgatta aattctcccc taaaacagtc   31320
actcgcaaca aactgcatgt taaacaaaac cacatctttg tcatcatcaa tggtgaacga   31380
ttaatatcca tttgccagct tgtccaataa tttcactcaa attattcaac acatttactg   31440
atgcatagaa ttatgcctca tccaacttta gaatagtata cacacaaata tagtttatct   31500
aaaataagca agacatacca atgagaacga ctgctaagct cattagcact agtggatcca   31560
acagatcggg cttggtttcc agacttcagc ttttcccaca catccactgt tccataaaca   31620
cgagcttcaa taagtcctgg gacttcttgg gttccatcta cagcttgctt tatctccaac   31680
ctacatttta tcagataaag cttacaattt gttcttcaca tcagtaataa cacttgagaa   31740
acatttaaaa cgtcaaagtt tcatgcttaa ttggattgaa aaggaggggg aagaaaggtt   31800
tgagattatg acaaaatgtt aatgggtttt actgtatatg cattttcaac tatgctacca   31860
tagaagacag gtgcagagat aatcaattaa agtcataagg tcttttagta aagttattag   31920
gttccaccaa aagtcatggt taatttatc agcatctcta ccttgcaaag caatatgcgt   31980
ttggcactca gattttatta cattagcatc atgtgcaaca gtgtaaaagt gaagcatta   32040 tttcattata aagcttatca aagtatagct gaagttgaat gaaaactcac ttcttagtag   32100
gttcaactga attttccacc aaaagatctc ttatcttctc attgtaaacc tctaacatgc   32160
taacaaacaa ttcatatttt attacatcat ttctctcttc agatattcga ataattcct   32220 ccagggttct atagttaact cccctatgct gaggtgttcc ctccatagta aaggtcttgc   32280
cagttccagt ttgaccatat gcaaaaatgc aaacattata cccatctaac acagatgtga   32340
cgataggtat tgtttgttcg aaaacagtct ctgcacaata aaataatcga cacactatta   32400
atcattaacc aacaaagaa agaaaatttc tcaactgaaa cttaaccacc aaaagttt    32460 aatttcttat gtaccttggt tatcttcagg tctgaataca taatcaaatt tgaagtgctt   32520
ttttgaagaa tcagagcaaa tgacttggag ctcatcagaa gatgactcaa aattgacaac   32580
agatactgct gatccatttg caatttcact ttcatttagt ggtctgcatc tacagaaaac   32640
tctgatattt cccttttagtt caatcacttc attgtaaagc cgcctacgct cagaggactc   32700
ctctacgtac tttcttttca acacttcata ttcagcacct agtgacagat aaaaaagatg   32760
aaaatctagt ataaagtaat cacatggaac cagatattat tattcaattt taggttagag   32820
ccttaccaag aagctgaaca gactttaaaa catctaggcc tggaaatgac tcagttgtga   32880
gtttcacttg attagatagg gctacatgtt gtttcttcaa attctgatac atgaaccata   32940
taaaccaaca tcaacaaaag caatgataca gaaggaattt gattagaagt gatactccga   33000
aggattttga ttcttttgtt tgaccaagcc atcaaccaac atttaaaatt tacctgaatt   33060
ttagtactca agtcaaggat tttcttcaat attgggagtg tatgatcctc acgaggagaa   33120
cattcatgga ttccattggg tatactactc tcatccatat tgtcagaggt ctcattgttc   33180
agttgtgcta atacattatc tgctgatata ccaaaatcca aataatcaga gggcagaggc   33240
aacatcgtaa ccagctttgt aagataagaa tcttttactt ccttaatttt tggataaat   33300 caaatctaaa ccccaaatca cattctctat ttaaagtata ttaggtttga aattttgttt   33360
gcacaaaatg aatgcctatt taaaacagaa actaatttgg aaaattagaa caagaagatt   33420
```

```
caataattca catttgcatt ccagaatcga ttataataac agtaataata ataaaataga    33480
aatttataag gagaagatag agaactgttg cagagaaata atctcgtaga atcagtgtct    33540
gtatacaaga tcttacaaaa gcattaagtg gatatgaaga aggagaaaaa cctgtttcat    33600
cacaagcttc agttgatacg cttggctgtg actctgaaat taaacaaata atccaataat    33660
tatgattttc ccaaacttaa aaaaaaaaaa aaaaaccta tataacaaat aaaagaatgg    33720
aaacctgatg acggcttcaa attgcaatta ataccgaatc gattgaactt ttctgtaagc    33780
atcttaatga tttgatctac aagaatattt acagcaattg ttaaatttcc tcgaagacaa    33840
agcgaaataa gaagaaagaa ggaaatgaag gaaagagcga gtaccgtcca tgacaacgta    33900
gattttgaag aagaagaaga agagatgaga tttcgctgac gaattcagag agagtgggag    33960
agattttgct tacgaaggaa caccgtttta gcgagaggta tttagctgtt gaatggttaa    34020
agcaaaaatg agagtttgaa ttttgggatc ggacactgaa agcagctatc atgcaacggc    34080
tactcataca tactaacaaa taatatgggc cgggccgggc caggcctctt attgaatgct    34140
aatggacaac atcccacacc ccctacggca atttaatgac tgttgctttc tgcagtccta    34200
ctattggctt cttacacttc tattatggaa aattcattct gaaatataat ttgtatttca    34260
gaatgggttt ttccataatg caatgataat tgcaagaagc aatagtggaa gtgtaagaag    34320
ttctatccca atttaatttg caattttttct ttcccctctt tgcatctctg tattttttct    34380 tattttttt atcaaaaata ttttttgccga aaaataactt ttagaactta tatttaacaa    34440
tatataaatg tccagaattt attttttcata attttagcttt ataacctttc gaaaacaaaa    34500
ttctaaaatg cctataaaat taattccatt ctagaattta gtttccaaaa taatgttgta    34560
aaaatataac aattttggaa attaaattcc agatttggtt ttatttttaac ttttgttgct    34620 ggatattata caaataattt tttttttagt tactataatt acttgagaca taaaaattta    34680
ttggaacact attttctatc tccattaaag tgatttttata aagataaaatt tattgagata    34740 tataacatat cattaggtgt ggtctatata taatttgtag atatcataag ttttatttat    34800
ttctattctt atgatgtcaa aatagaaata agtaagtcgt aacttttgtg aatgagtata    34860
attgtgaata gatataaggt ttaaaagata taactcttca tgaaagagta cttgcttgtt    34920
gtaaaaatag ttatggtcct caaatcatat gcatcaattt tctttcctaa ctaccatcaa    34980
taaagaagat caacacaatt atttcttcct caaacaatca tccatggata tggatatgga    35040
tatgcttcca cgtcaatcgc aattttatat tattgatgat ttaacataaa agttcaagtg    35100
atgtttatca taattctagt ttctcatctc acatggtcta acattacata cttatgaatt    35160
atgataaact tgaacgtcat tttaattatt tctcttgcct tttgctttttt ttgagctggc    35220 tgagacttta ttttgtatcc catgtatctc ccggagagtc agagactaat tccaactagt    35280
ctaaaggata taggaaagac aggtcgtgcc tcctctctca ttctcttaac agcaaaaaag    35340
aaaataaata tcaattgaca ctacatatgg ttttgccaga catttgtttc caaagtccaa    35400
atgcatgcat ttaaaagag aacaaaaaaa ggaagcagtc aagcagaaat gatacgaaga    35460
catctaattt gtcatcggtt agattaactt gtttatacat gaaaacagg catgttgcat    35520 agcaattctg catgatatgt tgcattacac aaacttgcca ccttgtcatg aaatgacacc    35580
cctagcagct cccctatcct tactaaaatc ataaagaaa gatacaataa atgagatata    35640
aaatgaaaaa tatatatata catagacatg gcaatggggc gggacgggta cgagtattgt    35700
ctccccaatc ccttactccg acttcccaac atatccccat acccgtatcc gatacccgac    35760
```

-continued

```
gggtataagt ttattgtccc atcccgatac ccgtcgggta cccgtcgggt attggatatc   35820 cccgaccca tcccatacac cattcaaatt agaaaaatat ttttttttgt aaaaaaaata   35880
ttaaaaattt gattttagaa aaataaatt gattgttaaa catttatttt taactactta   35940
tatatcaata aatttattat agtgcgtatg tctacaaaaa tagttaagaa aataatatta   36000
aattatgtaa aaattctaaa ataaaattaa ttagtaataa aaattctatg ccttttgatt   36060
aaattatgca aaaattctaa agattttaag tggcggggcg ggttcgggac gggtctaata   36120
atctcatacc tgtacccgta cccgactttt gtttatcggg gaaaacccga acccataccc   36180
gattaactcg gatattaccc gtcaaagtcg ggacgaattc gggcgggtac ccatgaatac   36240
gggttttctt gccatgtcta tatatgcata tccgaaactg tatgtagctt atattcttgg   36300
cgtatgtttc agagaaatta ggtataaggc ttctatgagc atctgatatc tagcaactgg   36360
tagtgtattg taaaccatgt cccaccaatt tcagtgctat tgactaggga cagtatatgg   36420
gcagggttgc tatccaaatg ttaaaaacaa tccacatgtt tgcttgaaga tttgggttgc   36480
tgcttctttg ttttttgata tcggttattc tcaaacttag cgttagttat aagtgaatag   36540
aggcatagag caagtcggcc tcagctgatg tatcataggg tacttccagt atactgcaac   36600
atcaaccaaa tggaaacaag aaataaaaag aatgtatata ataaactcca gattctatat   36660
agcatttcaa cgaaattacc acaggaattg aggcatttta tatgctatag aagattaatg   36720
ggaaaccagg ctagcttgta tcctttagt tttatacgag aaataataca tcaacagccg   36780
gaattgctaa tctgataaat tatcctgcat cagaaaatga tgttgtatta gcatctctgt   36840
taaggacctg aatgaatgaa gtaataataa caataatagt tgatatcggc ggcggagcag   36900
tgagggtcca gaggaccatc tctcagactg caactcgctc ttgccttctt cttcttagca   36960
aacaccgcaa aactgcgact tccaaattaa ttaagctcat cattgctact cttttctgtg   37020
cttcttcgta ttgcacttac tcttttatt ttcttactgt tataaattaa ttaagtaatt   37080
aaactttgac ttgaccccctt tattcattat atttctgcag ttgctcacat tttatattta   37140
attataagct ccacgtttta gtctaataca aatgaagtta gtttattgta atgataattt   37200
tttaacacct ctaaaaaatg aatatttctc taagactaat tatttctgta cccctctgat   37260
ccctcggttg gtcgctttat ctttttatgt tgttaatctt ccatccatgc ccgtataatc   37320
aaacaggctg ttcgcagacc gagagaagag agctcaaatc tgcatggttg agggcagatt   37380
ttgaggttgc aggaaatggg ttttgagaag ttggtgggtt cttcatgatg gaaggtatat   37440
tgagagaatc catccatgaa ggaagatgag cattgaattt ccatctggat ttcatccatg   37500
aaagggaaaa cagggaggct gatggggcgg ggaggaccct atttcacaga ctaattctaa   37560
acctaaggat aagtaaaagg tttatgctcc ggtgcctttg ccttttggta ttttttttaaa   37620 ttattatatt tgttaaacaa tagatattta ttttccaata aagaagagga aggatgtaaa   37680
agagtaatga atatcatgga ttgttaggtc acaaaggagt ggtggatcaa cttgacctaa   37740
ttcaccctaa caataggtta ggttggattt gtttgggtta aaaatctcaa ttcaacccaa   37800
ctttgatgag ttgtgagttg agtttgattg gcctcctgaa taaagaaata tttaattaaa   37860
caatccatca aataaaatta aaacttaac ttgatgagtc tgttcaatcg gattatgcag   37920
gttgaaaaat taaatcacac aatccaaaga aagttgtttt ggcaagttaa atgagttcac   37980
ttgtcaaatt taatttgttt tgacatctat aaccaacatg agactataac tttattgtgt   38040
gccttataat ccacacaaaa cacccatctt tcgtatatat ttttcttaa taaaaataat   38100 aggacttgag taagggctga tactaggttg tatgacgcta acagctacca agtcattaat   38160
```

```
tatttattcc atctcacacc ttttcgataa tagggatagt tgtactgtca cataggtatt  38220
ttagccactt cctttagtat aatagcatgg tcatgttttt gaaggggagg tagaccttcc  38280
actcttaaaa catatcttgg aattccacta aaatgtcttt aatggctagg aaaatacctc  38340
ctacattgtt ttgttctttt ggataaaata tgcacaagtc attgttagtg aacgtataat  38400
actagtggag taagtctgtg tagctgcaat acccgtgcat cattctctct tattttgtat  38460
tgcacagatt taccattaga taaacaattg caaagattaa tcttcaaaca ttgcaacgat  38520
atattagcct tttgaggtat agtaaaccaa caaataaaat tgaaatcatt aaggtctctc  38580
tttgtgatgc attttaata acacacacaa gactttatca tttcacaagg tttcaggaga  38640
ttactataca acttcgcaaa tgatttcacc tccatcgtaa ttccagccat gcagaataac  38700
tcgaggagtg acacccagag gaacctcaaa agatatattt ataggcatgg tctctcctgg  38760
gactagtgag aaatagttat ctgagtaatg aaccggaaga attcttgtgt ctttcccttc  38820
attgtggtcc atctttgaag tatgaacaga aaaatgaaga aagaaagcaa cgcctacatc  38880
aggcccactt atttcagtaa ctttcaaacc atcactttc ccagcaaaac atctatgtat  38940
cctcttaaac caactagatt tttgttctat tccaaccccca caagccagag tttccagtga  39000
gtgtgtgcca taaaaaccat cacttagcct agctgttgaa cttgtagagg ctggtctttt  39060
agatgtgttt gccacaagca tttgaatatt ataagtgcat tcttcaattg aaaccttcga  39120
tgttatcttg agaggtattt tcttctccct atatggctcc aataacttgt aatctccacc  39180
agaaagatgc aaccaataaa agtttctgga tataactcta ttatctgaca tgttatagag  39240
tttgagaaga agaaagtaga ctggctttgg atcttttgac tctggatact tcatcttaaa  39300
aataggtgct acttttttg gcagcaaaga gaaattttca tgaactctgt agtaagggca  39360
tgtcccgtca agatcccaca ctgaagcttc aatggcaaca ttagacattt cttctgctgt  39420
agtattaaca acctgttgtg ggaagaaaga taaaaagata cagaaccttt aatgacccac  39480
tctttcataa gtggaccatg cataaattgc aatgaaaatt gtgaatcata caattttcac  39540
aatttcttac actaataatc tttttaactt gccacatttg acttcctatc tcaattttaa  39600
cttaatgaat gggggaaaat atttatcata ttggtaaaat tgagacactc ataaaactag  39660
aaattcattt agacacttac ctctatcaaa tatgtagcca gattaagctg tacatgaact  39720
ggttctgcag cacaccgaca accatagaaa cctgctgttt gatcaagtag atgatcataa  39780
aattgacctc tcagaccagt ccagggattc tgtgtcttcc atattaatac acctgtatat  39840
ttactccaca tgcgagaagt ccatccctcc agaagagctc tatattgtat gtagttgaca  39900
agttgagcct gaaaagatta tagcatctaa attatacatc aacttcagca aaagatcatg  39960
aaaaatagga cgataaaaaa tgcattgcta atggccaaca g                      40001
```

LOCI ASSOCIATED WITH CHARCOAL ROT DROUGHT COMPLEX TOLERANCE IN SOYBEAN

CROSS REFERENCE TO RELATED APPLICATIONS

This application is a divisional of U.S. application Ser. No. 14/882,655 filed Oct. 14, 2015, which is a continuation-in-part of U.S. application Ser. No. 14/815,236 filed Jul. 31, 2015, which is incorporated by reference herein.

FIELD OF THE INVENTION

The present invention relates to compositions and methods for identifying soybean plants that are tolerant, have improved tolerance, or are susceptible to Charcoal Rot Drought Complex, where the methods use molecular genetic markers to identify, select and/or construct disease and/or drought-tolerant plants. The invention also relates to soybean plants that display tolerance or improved tolerance to Charcoal Rot Drought Complex that are generated by the methods of the invention.

REFERENCE TO A SEQUENCE LISTING SUBMITTED AS A TEXT FILE VIA EFS-WEB

A sequence listing having the file name "5185USCIP_SEQLIST.txt," created on Oct. 1, 2015, and having a size of 68,766 bytes is filed in computer readable form concurrently with the specification. The sequence listing is part of the specification and is herein incorporated by reference in its entirety.

BACKGROUND

Soybean, a legume, has become the world's primary source of seed oil and seed protein. In addition, its utilization is being expanded to the industrial, manufacturing and pharmaceutical sectors. Soybean productivity is a vital agricultural and economic consideration. Unfortunately, soybean is host to one of the widest ranges of infectious pathogens of all crops. More than a hundred different pathogens are known to affect soybean plants, some of which pose significant economic threats. Improving soybean disease tolerance to these many pathogens is crucial to preventing yield losses.

Charcoal Rot (or alternatively referred to herein as "Charcoal Rot Drought Complex") is caused by the fungus *Macrophomina phaseolina*. The fungus has a particularly wide geographic distribution and is found throughout the world. *M. phaseolina* is most severe between 35° North and 35° South latitude (Wyllie, (1976) '*Macrophomina phaseolina*—Charcoal Rot' P 482-484 In L. D. Hill (ed.) World Soybean Research Proc of the World Soybean Res. Conf., Champaign, Ill. Interstate, Danville, Ill.). The fungus also has a wide host range and infects over 500 crop and weed species and is highly variable. Known major crop hosts include alfalfa, maize, cotton, grain sorghum, peanut and soybean.

In localized areas, yield losses can be as high as 90%. In the period from 1996-2005, charcoal rot was the third leading cause of soybean yield loss in the U.S. Average annual losses were 29 MM bushels resulting in approximately $188 MM annual income loss. Only soybean cyst nematode and phytophthora root rot caused greater economic loss during that period (Wrather and Koenning (2006) 'Soybean Disease Loss Estimates for the United States, 1996-2006'. University of Missouri—Columbia Agriculture Experiment Station. November 2006 aes.missouri.edu/delta/research/soyloss.stm Dec. 5, 2007).

Complete or vertical resistance to *M. phaseolina* has not been identified in soybean, which strongly suggests that a single gene conferring resistance does not exist. In most field and greenhouse evaluations, the great majority of soybean cultivars have been found to be either highly or moderately susceptible to *M. phaseolina*. Only a few cultivars have been identified as possessing partial or horizontal resistance (Smith and Carville (1997) 'Field screening of commercial and experimental soybean cultivars for their reaction to *Macrophomina phaseolina*' Plant Dis 81:804-809).

It is the goal of the plant breeder to select plants and enrich the plant population for individuals that have desired traits, for example, pathogen tolerance, leading ultimately to increased agricultural productivity. It has been recognized for quite some time that specific chromosomal loci (or intervals) can be mapped in an organism's genome that correlate with particular quantitative phenotypes. Such loci are termed quantitative trait loci, or QTL. The plant breeder can advantageously use molecular markers to identify desired individuals by identifying marker alleles that show a statistically significant probability of co-segregation with a desired phenotype (e.g., pathogenic infection tolerance), manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select a desired phenotype by selecting for the proper molecular marker allele (a process called marker-assisted selection, or MAS). The more molecular markers that are placed on the genetic map, the more potentially useful that map becomes for conducting MAS.

Despite significant advances in research directed towards improved crop tolerance to Charcoal Rot Drought Complex, there remains a need in the art for improved soybean strains that are tolerant to Charcoal Rot and its causative agents, namely *Macrophomina phaseolina* infection and low-available water growth conditions. There is a need in the art for methods that identify soybean plants or populations (germplasm) that display tolerance to Charcoal Rot Drought Complex. What is needed in the art is to identify molecular genetic markers that are linked to Charcoal Rot Drought Complex tolerance loci in order to facilitate MAS. Such markers can be used to select individual plants and plant populations that show favorable marker alleles in soybean populations and then employed to select the tolerant phenotype, or alternatively, be used to counterselect plants or plant populations that show a Charcoal Rot Drought Complex susceptibility phenotype. The present invention provides these and other advantages.

BRIEF SUMMARY

Compositions and methods for identifying soybean plants or germplasm with tolerance to Charcoal Rot Drought Complex are provided. Methods of making soybean plants or germplasm that are tolerant to Charcoal Rot Drought Complex, e.g., through introgression of desired tolerance marker alleles and/or by transgenic production methods, as well as plants and germplasm made by these methods, are also provided. Systems and kits for selecting tolerant plants and germplasm are also a feature of the invention.

Disclosed are methods for identifying a first soybean plant or germplasm (e.g., a line or variety) that has tolerance, improved tolerance, or susceptibility to Charcoal Rot Drought Complex. In the methods, at least one allele of one or more marker locus (e.g., a plurality of marker loci) that is associated with the tolerance, improved tolerance, or susceptibility is detected in the first soybean plant or germplasm.

Also disclosed are methods of identifying a first soybean plant or germplasm that displays tolerance, improved tolerance, or susceptibility to Charcoal Rot; the method comprising detecting in the first soybean plant or germplasm at least one allele of a quantitative trait locus that is associated with the tolerance, improved tolerance, or susceptibility; wherein the quantitative locus is: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19.

Also disclosed are methods of identifying a first soybean plant or germplasm that displays tolerance, improved tolerance, or susceptibility to Charcoal Rot; the method comprising the steps of: (a) detecting in the first soybean plant or germplasm at least one allele of a quantitative trait locus that is associated with the tolerance, improved tolerance, or susceptibility; wherein the quantitative locus is: wherein the quantitative locus is: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19; (b) selecting the first soybean plant or germplasm, or selecting a progeny of the first soybean plant or germplasm comprising the at least one allele of a quantitative trait locus that is associated with the tolerance, improved tolerance, or susceptibility; and (c) crossing the selected first soybean plant or germplasm with a second soybean plant or germplasm to introgress the quantitative trait locus into progeny soybean germplasm.

Also disclosed are methods of identifying a first soybean plant or germplasm that displays tolerance, improved tolerance, or susceptibility to Charcoal Rot; the method comprising the steps of: (a) detecting in the first soybean plant or germplasm at least one allele of a quantitative trait locus that is associated with the tolerance, improved tolerance, or susceptibility; wherein the quantitative locus is: wherein the quantitative locus is: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19; (b) selecting the first soybean plant or germplasm, or selecting a progeny of the first soybean plant or germplasm comprising the at least one allele of a quantitative trait locus that is associated with the tolerance, improved tolerance, or susceptibility; (c) crossing the selected first soybean plant or germplasm with a second soybean plant or germplasm to introgress the quantitative trait locus into progeny soybean germplasm; (d) analyzing progeny soybean germplasm to determine the presence of tolerance to Charcoal Rot; and (d) selecting progeny soybean germplasm that tests positive for the presence of tolerance to Charcoal Rot as being soybean germplasm into which germplasm having said quantitative trait locus has been introgressed.

Also disclosed are introgressed soybean plants or germplasms produced by the disclosed methods.

Also disclosed are kits for selecting at least one soybean plant by marker assisted selection of a quantitative trait locus associated with the tolerance, improved tolerance, or susceptibility to Charcoal Rot comprising: (a) labeled primers or probes for detecting at least one nucleic acid sequence selected from the group consisting of: (i) 48,340-48,380 kbp of chromosome 19 (SEQ ID NO.: 26); (ii) 3,202-3,212 kbp of chromosome 15 (SEQ ID NO.: 25); (iii) S11315 (SEQ ID NO.: 1); (iv) S11316 (SEQ ID NO.: 6); (v) S29725 (SEQ ID NO: 11); (vi) S29742 (SEQ ID NO: 16); and (vii) S29741 (SEQ ID NO: 21); and (b) instructions for using the primers or probes to detect the marker loci and correlating the loci with predicted improved lodging resistance.

Also disclosed are methods for screening a plant for resistance to a plant pathogen, the method comprising: (a) providing at least one inoculation probe having a pointed end to a container of agar inoculated with a pathogen; wherein a surface of the inoculation probe is contact with the surface of the agar in the petri dish; (b) inoculating a plant, after a predetermined contact time between at least one inoculation probe and the pathogen, by inserting the pointed end of at least one inoculation probe, comprising pathogen on the surface thereof, into a site located on a plant stem; and (c) assessing plant tolerance to the pathogen at a predetermined time.

DETAILED DESCRIPTION

Figure 1:
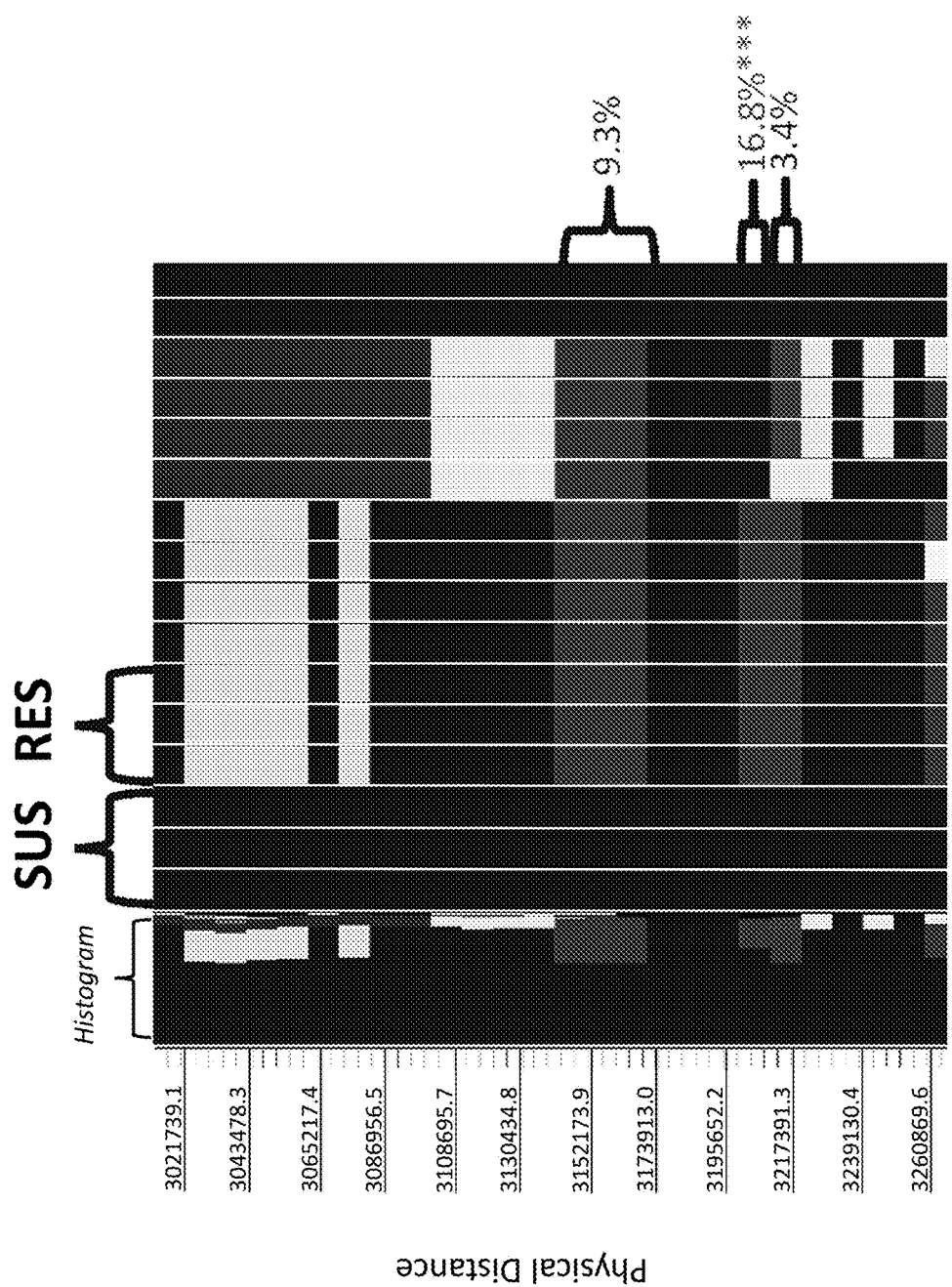
FIG. 1 shows representative data for haplotype analysis of Chromosome 15 in the region of approximately 3,012-3,946 kb on the Soybean Consensus Map 4.0 (Hyten D. L., et al., (2010) Crop Sci 50: 960-968) using 10 kb haplotype windows created using high density sequence data from 206 unique varieties. Displayed in columns are three known resistant and three known susceptible varieties, which are indicated respectively by "RES" and "SUS" in the figure. To the right are the results for 10 varieties with unknown QTL status. Indicated next to the last column on the right are regression values ($R^2$) for the effect of the indicated haplotype on charcoal rot drought complex across the set of 206 varieties. The left is a histogram (as indicated) representing the cumulative number of haplotypes from the columns to the right for each 10 kb window examined. The scale to the far left indicates the physical distance within the region examined in the columns to the right.

The disclosures herein will be described more fully hereinafter with reference to the accompanying drawings, in which some, but not all possible embodiments are shown. Indeed, disclosures may be embodied in many different forms and should not be construed as limited to the embodiments set forth herein; rather, these embodiments are provided so that this disclosure will satisfy applicable legal requirements.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

It is also to be understood that the terminology used herein is for the purpose of describing particular aspects only and is not intended to be limiting. As used in the specification and in the claims, the term "comprising" can include the aspect of "consisting of." Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

I. Definitions

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Thus, the term "soybean plant" includes whole soybean plants, soybean plant cells, soybean plant protoplast, soybean plant cell or soybean tissue culture from which soybean plants can be regenerated, soybean plant calli, soybean plant clumps and soybean plant cells that are intact in soybean plants or parts of soybean plants, such as soybean seeds, soybean pods, soybean flowers, soybean cotyledons, soybean leaves, soybean stems, soybean buds, soybean roots, soybean root tips and the like.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

The term "allele" refers to one of two or more different nucleotide sequences that occur at a specific locus. For example, a first allele can occur on one chromosome, while a second allele occurs on a second homologous chromosome, e.g., as occurs for different chromosomes of a heterozygous individual, or between different homozygous or heterozygous individuals in a population. A "favorable allele" is the allele at a particular locus that confers, or contributes to, an agronomically desirable phenotype, e.g., tolerance to Charcoal Rot Drought Complex, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease-prone plants. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele "positively" correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal region where a polymorphic nucleic acid, trait determinant, gene or marker is located. Thus, for example, a "gene locus" is a specific chromosome location in the genome of a species where a specific gene can be found.

The term "quantitative trait locus" or "QTL" refers to a polymorphic genetic locus with at least one allele that correlates with the differential expression of a phenotypic trait in at least one genetic background, e.g., in at least one breeding population or progeny. A QTL can act through a single gene mechanism or by a polygenic mechanism.

The terms "marker", "molecular marker", "marker nucleic acid", and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele", alternatively an "allele of a marker locus", is one of a plurality of polymorphic nucleotide sequences found at a marker locus in a population that is polymorphic for the marker locus. In some aspects, the present invention provides marker loci correlating with tolerance to Charcoal Rot Drought Complex in soybean. Each of the identified markers is expected to be in close physical and genetic proximity (resulting in physical and/or genetic linkage) to a genetic element, e.g., a QTL that contributes to tolerance.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes.

Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map.

A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

As used herein, the term "linkage" is used to describe the degree with which one marker locus is "associated with" another marker locus or some other locus (for example, a tolerance locus).

As used herein, linkage equilibrium describes a situation where two markers independently segregate, i.e., sort among progeny randomly. Markers that show linkage equilibrium are considered unlinked (whether or not they lie on the same chromosome).

As used herein, linkage disequilibrium describes a situation where two markers segregate in a non-random manner, i.e., have a recombination frequency of less than 50% (and by definition, are separated by less than 50 cM on the same linkage group). Markers that show linkage disequilibrium are considered linked. Linkage occurs when the marker locus and a linked locus are found together in progeny plants more frequently than not together in the progeny plants. As used herein, linkage can be between two markers, or alternatively between a marker and a phenotype. A marker locus can be associated with (linked to) a trait, e.g., a marker locus can be associated with tolerance or improved tolerance to a plant pathogen when the marker locus is in linkage disequilibrium with the tolerance trait. The degree of linkage of a molecular marker to a phenotypic trait is measured, e.g., as a statistical probability of co-segregation of that molecular marker with the phenotype.

As used herein, the linkage relationship between a molecular marker and a phenotype is given as a "probability" or "adjusted probability". The probability value is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "insignificant". In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p=0.5). For example, a significant probability can be less than 0.25, less than 0.20, less than 0.15, or less than 0.1.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The term "physically linked" is sometimes used to indicate that two loci, e.g., two marker loci, are physically present on the same chromosome.

Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic tolerance). For example, in some aspects, these markers can be termed linked QTL markers. In other aspects, especially useful molecular markers are those markers that are linked or closely linked.

In some aspects, linkage can be expressed as any desired limit or range. For example, in some embodiments, two linked loci are two loci that are separated by less than 50 cM map units. In other embodiments, linked loci are two loci that are separated by less than 40 cM. In other embodiments, two linked loci are two loci that are separated by less than 30 cM. In other embodiments, two linked loci are two loci that are separated by less than 25 cM. In other embodiments, two linked loci are two loci that are separated by less than 20 cM. In other embodiments, two linked loci are two loci that are separated by less than 15 cM. In some aspects, it is advantageous to define a bracketed range of linkage, for example, between 10 and 20 cM, or between 10 and 30 cM, or between 10 and 40 cM.

The more closely a marker is linked to a second locus, the better an indicator for the second locus that marker becomes. Thus, in one embodiment, closely linked loci such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

As used herein, the terms "chromosome interval" or "chromosome segment" designate a contiguous linear span of genomic DNA that resides in planta on a single chromosome. The genetic elements or genes located on a single chromosome interval are physically linked. The size of a chromosome interval is not particularly limited.

In some aspects, for example in the context of the present invention, generally the genetic elements located within a single chromosome interval are also genetically linked, typically within a genetic recombination distance of, for example, less than or equal to 20 cM, or alternatively, less than or equal to 10 cM. That is, two genetic elements within a single chromosome interval undergo recombination at a frequency of less than or equal to 20% or 10%.

In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The phrase "Charcoal Rot" refers to the plant disease caused by an infection of the plant with the fungal pathogen *Macrophomina phaseolina*. While Charcoal Rot is more common in the presence of low-available water growth conditions, it can exist even in the absence of such growth conditions.

The phrase "Charcoal Rot," "Charcoal Rot Drought Complex," or "CRDC" refers to a condition in a plant in which the disease caused by an infection with the fungal pathogen *Macrophomina phaseolina* interacts with low-available water growth conditions to subdue the plant. It is a combination of the infection of the fungus and the low-available water conditions that are most commonly encountered under field conditions. Under these field conditions, the plant is stressed by both the pathogen and environment and is subdued by the two stresses operating substantially simultaneously.

"Tolerance" or "improved tolerance" in a soybean plant to Charcoal Rot Drought Complex is an indication that the soybean plant is less affected with respect to yield and/or survivability or other relevant agronomic measures, upon introduction of the causative agents of that disease, e.g., *Macrophomina* infection and low-available water growth conditions. "Tolerance" or "improved tolerance" in a soybean plant to *Macrophomina* infection is an indication that the soybean plant is less affected with respect to yield and/or survivability or other relevant agronomic measures, upon infection of the plant with *Macrophomina* species, than a less tolerant or more "susceptible" plant. "Tolerance" or "improved tolerance" in a soybean plant to low-available water growth conditions is an indication that the soybean plant is less affected with respect to yield and/or survivability or other relevant agronomic measures, when faced with low-available water growth conditions or less-than-ideal hydration conditions, than a less tolerant or more "susceptible" plant. Tolerance is a relative term, indicating that the infected plant produces better yield of soybean than another, similarly treated, more susceptible plant. That is, the conditions cause a reduced decrease in soybean survival and/or yield in a tolerant soybean plant, as compared to a susceptible soybean plant.

One of skill will appreciate that soybean plant tolerance to Charcoal Rot Drought Complex varies widely, can represent a spectrum of more tolerant or less tolerant phenotypes, and can vary depending on the severity of the infection. However, by simple observation, one of skill can determine the relative tolerance or susceptibility of different plants, plant lines or plant families to Charcoal Rot Drought Complex, and furthermore, will also recognize the phenotypic gradations of "tolerant."

Ratings are assigned by evaluating all plants of a cultivar in a 2 row by 15 foot plot. Cultivar scores are based on a 1 to 9 system where a score of '9' would indicate that all plants in the plot are normal with no disease symptoms and a score of '1' would indicate that all plants in the plot are dead from disease. The experiments described herein score soybean tolerance to Charcoal Rot Drought Complex using the following scale: 9=no disease symptoms with normal plant growth; 8=very slight symptoms including up to a 10% reduction in leaflet and overall canopy size with no wilting; 7=wilting beginning to appear at the uppermost two nodes; 6=wilting at the uppermost three nodes and leaflet yellowing beginning appear; 5=Up to 5% plant death with wilting and yellowing of leaflets occurring at the uppermost four nodes; 4=Up to 10% plant death with wilting and yellowing of leaflets occurring at the uppermost four nodes; 3=Up to 25% plant death with wilting and yellowing of leaflets occurring at the uppermost four nodes; 2=up to 50% plant death; 1=50-100% plant death.

Charcoal Rot Drought Complex "tolerance" differs from *Macrophomina* "resistance" in that tolerance is a measure of a soybean plant's ability to survive and yield soybean despite the presence of *Macrophomina* infection, as opposed to a measure of the soybean plant's ability to resist infection, just as low-available water growth condition tolerance describes a soybean plant's ability to survive and yield soybean despite the existence of low-available water growth conditions. As used in the art, "tolerance" is sometimes referred to as "general resistance", "rate-reducing resistance" or "partial resistance".

As used herein, "microsclerotia" refers to a compact mass of mycelia with an outer melanized rind; produced as a resting structure by some fungi, including *Macrophomina phaseolis.*

As used herein, "inoculum" refers to a pathogen or its parts that can cause infection; that portion of individual pathogens that are brought into contact with the host.

As used herein, "inoculate" refers to bringing a pathogen into contact with a host plant or plant organ.

The term "crossed" or "cross" in the context of this invention means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, or the like. In any case, offspring comprising the desired allele can be repeatedly backcrossed to a line having a desired genetic background and selected for the desired allele, to result in the allele becoming fixed in a selected genetic background.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a "subline" has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. In the context of the invention, marker-based sublines, that differ from each other based on qualitative polymorphism at the DNA level at one or more specific marker loci, are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (yield, tolerance, etc.).

An "ancestral line" is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and its parents, grand parents, great-grand parents, etc.

An "elite line" or "elite strain" is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

In contrast, an "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, or enhancer regions) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

An "exogenous nucleic acid" is a nucleic acid that is not native to a specified system (e.g., a germplasm, plant, or variety), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts.

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term "recombinant" in reference to a nucleic acid or polypeptide indicates that the material (e.g., a recombinant nucleic acid, gene, polynucleotide, or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural context and cloned into any type of artificial nucleic acid vector. Protocols and reagents to produce recombinant molecules, especially recombinant nucleic acids, are common and routine in the art. In one embodiment, an artificial chromosome can be created and inserted into maize plants by any method known in the art (e.g., direct transfer processes, such as, e.g., PEG-induced DNA uptake, protoplast fusion, microinjection, electroporation, and microprojectile bombardment). An artificial chromosome is a piece of DNA that can stably replicate and segregate alongside endogenous chromosomes. It has the capacity to accommodate and express heterologous genes inserted therein. Integration of heterologous DNA into the megareplicator region (primary replication initiation site of centromeres) or in close proximity thereto, initiates a large-scale amplification of megabase-size chromosomal segments, which leads to de novo chromosome formation. See, e.g., U.S. Pat. No. 6,077,697, incorporated herein by reference.

The term recombinant can also refer to an organism that harbors recombinant material, e.g., a plant that comprises a recombinant nucleic acid is considered a recombinant plant. In some embodiments, a recombinant organism is a transgenic organism.

The term "introduced" when referring to translocating a heterologous or exogenous nucleic acid into a cell refers to the incorporation of the nucleic acid into the cell using any methodology. The term encompasses such nucleic acid introduction methods as "transfection", "transformation" and "transduction".

As used herein, the term "vector" is used in reference to polynucleotide or other molecules that transfer nucleic acid segment(s) into a cell. The term "vehicle" is sometimes used interchangeably with "vector". A vector optionally comprises parts which mediate vector maintenance and enable its intended use (e.g., sequences necessary for replication, genes imparting drug or antibiotic resistance, a multiple cloning site, or operably linked promoter/enhancer elements which enable the expression of a cloned gene). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term "expression vector" as used herein refers to a vector comprising operably linked polynucleotide sequences that facilitate expression of a coding sequence in a particular host organism (e.g., a bacterial expression vector or a plant expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes.

The term "transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

A specified nucleic acid is "derived from" a given nucleic acid when it is constructed using the given nucleic acid's sequence, or when the specified nucleic acid is constructed using the given nucleic acid. For example, a cDNA or EST is derived from an expressed mRNA.

The term "genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome segment.

The terms "phenotype", or "phenotypic trait" or "trait" refers to one or more trait of an organism. The phenotype can be observable to the naked eye, or by any other means of evaluation known in the art, e.g., microscopy, biochemical analysis, genomic analysis, or an assay for a particular disease resistance. In some cases, a phenotype is directly controlled by a single gene or genetic locus, i.e., a "single gene trait". In other cases, a phenotype is the result of several genes.

A "molecular phenotype" is a phenotype detectable at the level of a population of (one or more) molecules. Such molecules can be nucleic acids such as genomic DNA or RNA, proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

A "set" of markers or probes refers to a collection or group of markers or probes, or the data derived therefrom, used for a common purpose, e.g., identifying soybean plants with a desired trait (e.g., tolerance to Charcoal Rot Drought Complex). Frequently, data corresponding to the markers or probes, or data derived from their use, is stored in an electronic medium. While each of the members of a set possess utility with respect to the specified purpose, individual markers selected from the set as well as subsets including some, but not all of the markers, are also effective in achieving the specified purpose.

A "look up table" is a table that correlates one form of data to another, or one or more forms of data with a predicted outcome that the data is relevant to. For example, a look up table can include a correlation between allele data and a predicted trait that a plant comprising a given allele is likely to display. These tables can be, and typically are, multidimensional, e.g., taking multiple alleles into account simultaneously, and, optionally, taking other factors into account as well, such as genetic background, e.g., in making a trait prediction.

A "computer readable medium" is an information storage media that can be accessed by a computer using an available or custom interface. Examples include memory (e.g., ROM, RAM, or flash memory), optical storage media (e.g., CD-ROM), magnetic storage media (computer hard drives, floppy disks, etc.), punch cards, and many others that are commercially available. Information can be transmitted between a system of interest and the computer, or to or from the computer to or from the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

Specific physical map positions referenced herein throughout are to the physical position (bp) on the Glyma 1 Assembly reference (Schmutz, Jeremy, et al. "Genome sequence of the palaeopolyploid soybean." Nature 463.7278 (2010): 178-183).

Genetic map positions referenced herein throughout are to the genetic position (cM) on the Soybean Consensus Map 4.0 (Hyten D. L., et al., (2010) Crop Sci 50: 960-968).

II. Overview

Charcoal Rot is a disease of soybean, causing reduced plant viability and reductions in yield. This disease is caused by infection of the plant with *Macrophomina phaseolina*, a fungal pathogen. Though this disease is most prevalent during low-available water growth conditions, it can exist even in the absence of such growth conditions. While *Macrophomina* resistant plants have been previously developed, the strong selective pressures that resistant soybean impose on *Macrophomina* is likely to cause relatively rapid loss of resistance against races of *Macrophomina* that evolve to combat resistance traits in the resistant soybean, as has been seen with other soybean fungal pathogens, such as *Sclerotinia*. Accordingly, tolerance to Charcoal Rot and/or *Macrophomina* infection, in which the plant survives, thrives and produces high yields, despite a productive *Macrophomina* infection, is an alternate strategy to combat losses due to Charcoal Rot and/or *Macrophomina* infection. That is, there is not a strong negative selection against *Macrophomina* imposed by tolerance, because tolerant soybean plants support a productive *Macrophomina* infection.

Further, as plant stress caused by low-available water growth conditions is related to the existence and severity of Charcoal Rot and/or *Macrophomina* infection, with plants showing reduced survivability and yield from these conditions when coupled with low-available water growth conditions, soybean plants tolerant to low-available water growth conditions would show increased Charcoal Rot and/or *Macrophomina* infection tolerance, as well, and are therefore desirable. In addition, as low-available water growth condition is itself a major cause of loss of plant viability and yield, even in the absence of Charcoal Rot and/or *Macrophomina* infection, plants tolerant to such growth conditions are desirable for their direct benefits, not related to Charcoal Rot as well.

The identification and selection of soybean plants that show tolerance to Charcoal Rot Drought Complex using MAS can provide an effective and environmentally friendly approach to overcoming losses caused by this disease. The present invention provides soybean marker loci that demonstrate statistically significant co-segregation with Charcoal Rot Drought Complex tolerance. Detection of these loci or additional linked loci can be used in marker assisted soybean breeding programs to produce tolerant plants, or plants with improved tolerance. The marker loci identified herein include S29725-001; S29741-001; S29742-001; S11315-1; and S11316-1.

Each of the marker loci can be visualized as PCR amplicons as described herein. The PCR primer pairs that are used to generate the marker loci amplicons include: SEQ ID NO: 12 and SEQ ID NO: 13 used to amplify an amplicon associated with S29725 (SEQ ID NO.: 11); SEQ ID NO: 17 and SEQ ID NO: 18 used to amplify the amplicon associated with S29742 (SEQ ID NO.: 21); SEQ ID NO: 22 and SEQ ID NO: 23 used to amplify the amplicon associated with S29741 (SEQ ID NO.: 21); SEQ ID NO: 2 and SEQ ID NO: 3 used to amplify the amplicon associated with S11315 (SEQ ID NO.: 1); and SEQ ID NO: 7 and SEQ ID NO: 8 used to amplify the amplicon associated with S11316 (SEQ ID NO.: 6). In various further aspects, the marker loci can be visualized by probes such as the group consisting of SEQ ID NOs: 4, 5, 9, 10, 14, 15, 19, 20, and 24.

The invention also provides chromosomal QTL intervals that correlate with Charcoal Rot Drought Complex tolerance. These intervals are located Chromosomes 5, 15, and 19. Any marker located within these intervals finds use as a marker for Charcoal Rot Drought Complex tolerance. These intervals include: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19.Alternatively, these intervals can be specified as follows: (i) a chromosomal interval located within about 2 Mbp of an interval at 7,975-8,015 kpb of chromosome 5; (ii) a chromosomal interval located within about 2 Mbp of an interval at 3,202-3,212 kbp of chromosome 15 (SEQ ID NO.: 25); (iii) a chromosomal interval located within about 2 Mbp of an interval at 27,178-27,218 kbp; or (iv) a chromosomal interval located within about 2 Mbp of an interval at 48,340-48,380 kbp of chromosome 19 (SEQ ID NO.: 26).

Methods for identifying soybean plants or germplasm that carry preferred alleles of tolerance marker loci are a feature of the invention. In these methods, any of a variety of marker detection protocols is used to identify marker loci, depending on the type of marker loci. Typical methods for marker detection include amplification and detection of the resulting amplified markers, e.g., by PCR, LCR, transcription based amplification methods, or the like. These include ASH, SSR detection, RFLP analysis and many others.

In various aspects, disclosed are methods for identifying a first soybean plant or germplasm (e.g., a line or variety) that has tolerance, improved tolerance, or susceptibility to Charcoal Rot Drought Complex. In the methods, at least one allele of one or more marker locus (e.g., a plurality of marker loci) that is associated with the tolerance, improved tolerance, or susceptibility is detected in the first soybean plant or germplasm.

Also disclosed are methods of identifying a first soybean plant or germplasm that displays tolerance, improved tolerance, or susceptibility to Charcoal Rot; the method comprising detecting in the first soybean plant or germplasm at least one allele of a quantitative trait locus that is associated with the tolerance, improved tolerance, or susceptibility; wherein the quantitative locus is: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19.

Also disclosed are methods of identifying a first soybean plant or germplasm that displays tolerance, improved tolerance, or susceptibility to Charcoal Rot; the method comprising the steps of: (a) detecting in the first soybean plant or germplasm at least one allele of a quantitative trait locus that is associated with the tolerance, improved tolerance, or susceptibility; wherein the quantitative locus is: wherein the quantitative locus is: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19; (b) selecting the first soybean plant or germplasm, or selecting a progeny of the first soybean plant or germplasm comprising the at least one allele of a quantitative trait locus that is associated with the tolerance, improved tolerance, or susceptibility; and (c) crossing the selected first soybean plant or germplasm with a second soybean plant or germplasm to introgress the quantitative trait locus into progeny soybean germplasm.

Also disclosed are methods of identifying a first soybean plant or germplasm that displays tolerance, improved tolerance, or susceptibility to Charcoal Rot; the method comprising the steps of: (a) detecting in the first soybean plant or germplasm at least one allele of a quantitative trait locus that is associated with the tolerance, improved tolerance, or susceptibility; wherein the quantitative locus is: wherein the quantitative locus is: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19; (b) selecting the first soybean plant or germplasm, or selecting a progeny of the first soybean plant or germplasm comprising the at least one allele of a quantitative trait locus that is associated with the tolerance, improved tolerance, or susceptibility; (c) crossing the selected first soybean plant or germplasm with a second soybean plant or germplasm to introgress the quantitative trait locus into progeny soybean germplasm; (d) analyzing progeny soybean germplasm to determine the presence of tolerance to Charcoal Rot; and (d) selecting progeny soybean germplasm that tests positive for the presence of tolerance to Charcoal Rot as being soybean germplasm into which germplasm having said quantitative trait locus has been introgressed.

In various aspects, the quantitative trait locus is localized at a chromosomal interval of about 18 cM to about 37 cM of chromosome 5. In a further aspect, the quantitative trait locus is localized at a chromosomal interval of about 16 cM to about 35 cM of chromosome 5. In a still further aspect, the quantitative trait locus is localized at a chromosomal interval of about 25.8 cM to about 29.9 cM of chromosome 5. In a yet further aspect, the quantitative trait locus is localized at a chromosomal interval of about 26.3 cM to about 29.4 cM of chromosome 5. In an even further aspect, the quantitative trait locus is localized at a chromosomal interval of about 26.8 cM to about 28.9 cM of chromosome 5. In a still further aspect, the quantitative trait locus is localized at a chromosomal interval of about 27.3 cM to about 29.4 cM of chromosome 5.

In various aspects, wherein the quantitative trait locus is localized at a chromosomal interval of about 6 cM to about 25 cM of chromosome 15. In a further aspect, the quantitative trait locus is localized at a chromosomal interval of about 8 cM to about 23 cM of chromosome 15. In a still further aspect, the quantitative trait locus is localized at a chromosomal interval of about 13.5 cM to about 17.5 cM of chromosome 15. In a yet further aspect, the quantitative trait locus is localized at a chromosomal interval of about 14 cM to about 17 cM of chromosome 15. In an even further aspect, the quantitative trait locus is localized at a chromosomal interval of about 14.5 cM to about 16.5 cM of chromosome 15. In a still further aspect, the quantitative trait locus is localized at a chromosomal interval of about 15 cM to about 16 cM of chromosome 15. In a still further aspect, the quantitative trait locus is localized at a chromosomal interval of about 15.25 cM to about 15.75 cM of chromosome 15.

In various aspects, a marker locus of the quantitative trait locus on chromosome 15 is S29725-001. In a further aspect, a marker locus of the quantitative trait locus on chromosome 15 is S29742-001. In a still further aspect, a marker locus of the quantitative trait locus on chromosome 15 is S29741-001.

In various aspects, the quantitative trait locus on chromosome 15 is flanked by and including S29725-001 and S29741-001. In a further aspect, the quantitative trait locus on chromosome 15 is flanked by and including S29725-001 and S29742-001.

In various aspects, the quantitative trait locus is localized at a chromosomal interval of about 20 cM to about 39 cM of chromosome 19. In a further aspect, the quantitative trait locus is localized at a chromosomal interval of about 22 cM to about 37 cM of chromosome 19. In a still further aspect, the quantitative trait locus is localized at a chromosomal interval of about 27.3 cM to about 31.4 cM of chromosome 19. In a yet further aspect, the quantitative trait locus is localized at a chromosomal interval of about 27.8 cM to about 30.9 cM of chromosome 19. In an even further aspect, the quantitative trait locus is localized at a chromosomal interval of about 28.3 cM to about 30.4 cM of chromosome 19. In a still further aspect, the quantitative trait locus is localized at a chromosomal interval of about 28.8 cM to about 29.9 cM of chromosome 19.

In various aspects, the quantitative trait locus is localized at a chromosomal interval of about 82 cM to about 101 cM of chromosome 19. In a further aspect, the quantitative trait locus is localized at a chromosomal interval of about 84 cM to about 99 cM of chromosome 19. In a still further aspect, the quantitative trait locus is localized at a chromosomal interval of about 86 cM to about 97 cM of chromosome 19. In a yet further aspect, the quantitative trait locus is localized at a chromosomal interval of about 90.1 cM to about 93.1 cM of chromosome 19. In an even further aspect, the quantitative trait locus is localized at a chromosomal interval of about 90.6 cM to about 92.5 cM of chromosome 19. In a still further aspect, the quantitative trait locus is localized at a chromosomal interval of about 91.0 cM to about 92.2 cM of chromosome 19. In a yet further aspect, the quantitative trait locus is localized at a chromosomal interval of about 91.2 cM to about 92.0 cM of chromosome 19.

In various aspects, a marker locus of the quantitative trait locus on chromosome 19 is S11315-1. In a further aspect, a marker locus of the quantitative trait locus on chromosome 19 is S11316-1.

In various aspects, the quantitative trait locus on chromosome 15 is flanked by and including S11315-1 and S11316-1.

Although particular marker alleles can show co-segregation with a disease tolerance or susceptibility phenotype, it is important to note that the marker locus is not necessarily part of the QTL locus responsible for the tolerance or susceptibility. For example, it is not a requirement that the marker polynucleotide sequence be part of a gene that imparts disease resistance (for example, be part of the gene open reading frame). The association between a specific marker allele with the tolerance or susceptibility phenotype is due to the original "coupling" linkage phase between the marker allele and the QTL tolerance or susceptibility allele in the ancestral soybean line from which the tolerance or susceptibility allele originated. Eventually, with repeated recombination, crossing over events between the marker and QTL locus can change this orientation. For this reason, the favorable marker allele may change depending on the linkage phase that exists within the tolerant parent used to create segregating populations. This does not change the fact that the genetic marker can be used to monitor segregation of the phenotype. It only changes which marker allele is considered favorable in a given segregating population.

Identification of soybean plants or germplasm that include a marker locus or marker loci linked to a tolerance trait or traits provides a basis for performing marker assisted selection of soybean. Soybean plants that comprise favorable markers or favorable alleles are selected for, while soybean plants that comprise markers or alleles that are negatively correlated with tolerance can be selected against. Desired markers and/or alleles can be introgressed into soybean having a desired (e.g., elite or exotic) genetic background to produce an introgressed tolerant soybean plant or germplasm. In some aspects, it is contemplated that a plurality of tolerance markers are sequentially or simultaneous selected and/or introgressed. The combinations of tolerance markers that are selected for in a single plant is not limited, and can include any combination of markers recited in FIG. 1, any markers linked to the markers recited in FIG. 1, or any markers located within the QTL intervals defined herein.

Various methods are known in the art for determining (and measuring) the tolerance of a soybean plant to Charcoal Rot Drought Complex. They describe a tolerance measurement scale of 1-9, with 9=no disease and 1=total necrosis caused by *Macrophomina phaseolina*. It will be appreciated that all such scales are relative and that numbering and precise correlation to any scale can be performed at the discretion of the practitioner.

Typically, individual field tests are monitored for Charcoal Rot symptoms during the middle to late vegetative stages, but such symptoms typically appear in the early reproductive stage (during flowering and early pod set). Data collection is usually done in 3 or 4 successive scorings about 7 days apart. Scorings continue until worsening symptoms can no longer be quantified or until the symptoms are confounded by other factors such as other diseases, insect pressure, severe weather, or advancing maturity.

In general, while there is a certain amount of subjectivity to assigning severity measurements for disease caused symptoms, assignment to a given scale as noted above is well within the skill of a practitioner in the field. Measurements can also be averaged across multiple scorers to reduce variation in field measurements. Furthermore, although protocols using artificial inoculation of field nurseries with *Macrophomina phaseolina* can certainly be used in assessing tolerance, it is also typical for tolerance ratings to be based on actual field observations of fortuitous natural disease incidence, with the information corresponding to disease incidence for a cultivar being averaged over many locations and, typically, several years of crop growing.

If there is no disease present, the rating system above is inapplicable, because everything in an uninfected field scores as tolerant. However, if Charcoal Rot does occur in a specific field location, all of the lines at that location can be scored as noted above. These scores can accumulate over locations and years to show disease tolerance for given cultivars. Thus, older lines can have more years of observation than newer ones etc. However, relative measurements can easily be made using the scoring system noted above. Furthermore, the tolerance ratings can be updated and refined each year based on the previous year's observations in the field. Based on this, Charcoal Rot scores for a cultivar are relative measurements of tolerance.

The experiments described herein score soybean tolerance to Charcoal Rot Drought Complex using the following scale: 9=no disease symptoms with normal plant growth; 8=very slight symptoms including up to a 10% reduction in leaflet and overall canopy size with no wilting; 7=wilting beginning to appear at the uppermost two nodes; 6=wilting at the uppermost three nodes and leaflet yellowing beginning appear; 5=Up to 5% plant death with wilting and yellowing of leaflets occurring at the uppermost four nodes; 4=Up to 10% plant death with wilting and yellowing of leaflets occurring at the uppermost four nodes; 3=Up to 25% plant death with wilting and yellowing of leaflets occurring at the uppermost four nodes; 2=up to 50% plant death; 1=50-100% plant death.

Tolerance assays are useful to verify that the tolerance trait still segregates with the marker in any particular plant or population, and, of course, to measure the degree of tolerance improvement achieved by introgressing or recombinantly introducing the trait into a desired background.

Systems, including automated systems for selecting plants that comprise a marker of interest and/or for correlating presence of the marker with tolerance are also a feature of the invention. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

Also disclosed are introgressed soybean plants or germplasms produced by the disclosed methods.

Kits are also a feature of the invention. For example, a kit can include appropriate primers or probes for detecting tolerance associated marker loci and instructions in using the primers or probes for detecting the marker loci and correlating the loci with predicted Charcoal Rot Drought Complex tolerance. The kits can further include packaging materials for packaging the probes, primers or instructions, controls such as control amplification reactions that include probes, primers or template nucleic acids for amplifications, molecular size markers, or the like.

Also disclosed are kits for selecting at least one soybean plant by marker assisted selection of a quantitative trait locus associated with the tolerance, improved tolerance, or susceptibility to Charcoal Rot comprising: (a) labeled primers or probes for detecting at least one nucleic acid sequence selected from the group consisting of: (i) 48,340-48,380 kbp of chromosome 19 (SEQ ID NO.: 26); (ii) 3,202-3,212kbp of chromosome 15 (SEQ ID NO.: 25); (iii) S11315 (SEQ ID NO.: 1); (iv) S11316 (SEQ ID NO.: 6); (v) S29725 (SEQ ID NO: 11); (vi) S29742 (SEQ ID NO: 16); and (vii) S29741 (SEQ ID NO: 21); and (b) instructions for using the primers or probes to detect the marker loci and correlating the loci with predicted improved lodging resistance.

In various aspects, the labeled primers of the kit comprise a pair of olignucleotides selected from the group consisting of: (a) SEQ ID NO: 2 and SEQ ID NO: 3; (b) SEQ ID NO: 7 and SEQ ID NO: 8; (c) SEQ ID NO: 12 and SEQ ID NO: 13; (d) SEQ ID NO: 17 and SEQ ID NO: 18; and (e) SEQ ID NO: 22 and SEQ ID NO: 23; wherein at least one of the oligonucleotides is linked to a detectable label.

In various aspects, the labeled probes of the kit comprise an oligonucleotide selected from the group consisting of: SEQ ID NOs: 4, 5, 9, 10, 14, 15, 19, 20, and 24; and wherein the oligonucleotide is linked to a detectable label.

III. Tolerance Markers and Favorable Alleles

In traditional linkage analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked". The frequency with which the traits are inherited together is the primary measure of how tightly the traits are linked, i.e., traits which are inherited together with a higher frequency are more closely linked than traits which are inherited together with lower (but still above random) frequency. Traits are linked because the genes which underlie the traits reside on the same chromosome. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in two genes segregating separately into progeny.

A common measure of linkage is the frequency with which traits cosegregate. This can be expressed as a percentage of cosegregation (recombination frequency) or, also commonly, in centiMorgans (cM). The cM is named after the pioneering geneticist Thomas Hunt Morgan and is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency. For example, in soybean, 1 cM correlates, on average, to about 400,000 base pairs (400 Kb).

Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation. The marker loci, including S29725-001; S29741-001; S29742-001;S11315-1; and S11316-1, as well as any of the chromosome intervals: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19; have been found to correlate with tolerance, improved tolerance or susceptibility to Charcoal Rot Drought Complex in soybean. Alternatively, these intervals can be specified as follows: (i) a chromosomal interval located within about 2 Mbp of an interval at 7,975-8,015 kpb of chromosome 5; (ii) a chromosomal interval located within about 2 Mbp of an interval at 3,202-3,212 kbp of chromosome 15 (SEQ ID NO.: 25); (iii) a chromosomal interval located within about 2 Mbp of an interval at 27,178-27,218 kbp; or (iv) a chromosomal interval located within about 2 Mbp of an interval at 48,340-48,380 kbp of chromosome 19 (SEQ ID NO.: 26).

The marker loci 529725-001; 529741-001; 529742-001; 511315-1; and 511316-1 are localized as specified in Table 1 below.

TABLE 1

| No. | Loci Name | Chromosome | Physical Map Position* | Genetic Map Position** |
|---|---|---|---|---|
| 1 | S29725-001 | 15 | 2,938,271 | 15.07 |
| 2 | S29741-001 | 15 | 3,210,335 | 15.75 |
| 3 | S29742-001 | 15 | 3,211,837 | 16.72 |
| 4 | S11315-1 | 19 | 48,354,468 | 91.43 |
| 5 | S11316-1 | 19 | 48,384,426 | 91.53 |

*Physical position (bp) on the Glyma 1 Assembly reference (Schmutz, Jeremy, et al. "Genome sequence of the palaeopolyploid soybean." Nature 463.7278 (2010): 178-183).
**Genetic position (cM) on the Soybean Consensus Map 4.0 (Hyten D. L., et al., (2010) Crop Sci 50: 960-968).

This means that the markers are sufficiently proximal to a tolerance trait that they can be used as a predictor for the tolerance trait. This is extremely useful in the context of marker assisted selection (MAS), discussed in more detail herein. In brief, soybean plants or germplasm can be selected for markers or marker alleles that positively correlate with tolerance, without actually raising soybean and measuring for tolerance or improved tolerance (or, contrarily, soybean plants can be selected against if they possess markers that negatively correlate with tolerance or improved tolerance). MAS is a powerful shortcut to selecting for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

A favorable allele of a marker is that allele of the marker that co-segregates with a desired phenotype (e.g., disease tolerance). As used herein, a QTL marker has a minimum of one favorable allele, although it is possible that the marker might have two or more favorable alleles found in the population. Any favorable allele of that marker can be used advantageously for the identification and construction of tolerant soybean lines. Optionally, one, two, three or more favorable allele(s) of different markers are identified in, or introgressed into a plant, and can be selected for or against during MAS. Desirably, plants or germplasm are identified that have at least one such favorable allele that positively correlates with tolerance or improved tolerance.

Alternatively, a marker allele that co-segregates with disease susceptibility also finds use with the invention, since that allele can be used to identify and counter select disease-susceptible plants. Such an allele can be used for exclusionary purposes during breeding to identify alleles that negatively correlate with tolerance, to eliminate susceptible plants or germplasm from subsequent rounds of breeding.

In some embodiments of the invention, a plurality of marker alleles are simultaneously selected for in a single plant or a population of plants. In these methods, plants are selected that contain favorable alleles from more than one tolerance marker, or alternatively, favorable alleles from more than one tolerance marker are introgressed into a desired soybean germplasm. One of skill in the art recognizes that the simultaneous selection of favorable alleles from more than one disease tolerance marker in the same plant is likely to result in an additive (or even synergistic) protective effect for the plant.

One of skill recognizes that the identification of favorable marker alleles is germplasm-specific. The determination of which marker alleles correlate with tolerance (or susceptibility) is determined for the particular germplasm under study. One of skill recognizes that methods for identifying the favorable alleles are routine and well known in the art, and furthermore, that the identification and use of such favorable alleles is well within the scope of the invention. Furthermore still, identification of favorable marker alleles in soybean populations other than the populations used or described herein is well within the scope of the invention.

The PCR primer pairs that are used to generate the marker loci amplicons include: SEQ ID NO: 12 and SEQ ID NO: 13 used to amplify an amplicon associated with S29725 (SEQ ID NO.: 11); SEQ ID NO: 17 and SEQ ID NO: 18 used to amplify the amplicon associated with S29742 (SEQ ID NO.: 21); SEQ ID NO: 22 and SEQ ID NO: 23 used to amplify the amplicon associated with S29741 (SEQ ID NO.: 21); SEQ ID NO: 2 and SEQ ID NO: 3 used to amplify the amplicon associated with S11315(SEQ ID NO.: 1); and SEQ ID NO: 7 and SEQ ID NO: 8 used to amplify the amplicon associated with S11316 (SEQ ID NO.: 6), are a feature of the invention. Another feature of the invention are probes that are can be used to genotype the marker loci, and these probes include the group consisting of SEQ ID NOs: 4, 5, 9, 10, 14, 15, 19, 20, and 24. However, one of skill will immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the invention is not limited to the primers and probes specifically recited herein.

In some aspects, methods of the invention utilize an amplification step to detect/genotype a marker locus. However, it will be appreciated that amplification is not a requirement for marker detection—for example, one can directly detect unamplified genomic DNA simply by performing a Southern blot on a sample of genomic DNA. Procedures for performing Southern blotting, amplification (PCR, LCR, or the like) and many other nucleic acid detection methods are well established and are taught, e.g., in Sambrook, et al., (2000) Molecular Cloning—A Laboratory Manual (3rd Ed.), Vol. 1-3, Cold Spring Harbor Laboratory, Cold Spring Harbor, N.Y., ("Sambrook"); Current Protocols in Molecular Biology, Ausubel, et al., eds., Current Protocols, a joint venture between Greene Publishing Associates, Inc. and John Wiley & Sons, Inc., (supplemented through 2002) ("Ausubel")) and PCR Protocols A Guide to Methods and Applications (Innis, et al., eds) Academic Press Inc. San Diego, Calif. (1990) (Innis). Additional details regarding detection of nucleic acids in plants can also be found, e.g., in Plant Molecular Biology (1993) Croy (ed.) BIOS Scientific Publishers, Inc.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. Any of the aforementioned marker types can be employed in the context of the invention to identify chromosome segments encompassing genetic element that contribute to superior agronomic performance (e.g., tolerance or improved tolerance).

IV. QTL Chromosome Intervals

In some aspects, the invention provides QTL chromosome intervals, where a QTL (or multiple QTLs) that segregate with Charcoal Rot Drought Complex tolerance are contained in those intervals. A variety of methods well known in the art are available for identifying chromosome intervals, including those methods described herein. The boundaries of such chromosome intervals are drawn to encompass markers that will be linked to one or more QTL. In other words, the chromosome interval is drawn such that any marker that lies within that interval (including the terminal markers that define the boundaries of the interval) can be used as markers for disease tolerance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

The present invention provides soybean chromosome intervals, where the markers within that interval demonstrate co-segregation with tolerance to Charcoal Rot Drought Complex. Thus, each of these intervals comprises at least one Charcoal Rot Drought Complex tolerance QTL. These intervals include: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19. Alternatively, these intervals can be specified as follows: (i) a chromosomal interval located within about 2 Mbp of an interval at 7,975-8,015 kpb of chromosome 5; (ii) a chromosomal interval located within about 2 Mbp of an interval at 3,202-3,212kbp of chromosome 15 (SEQ ID NO.:

25); (iii) a chromosomal interval located within about 2 Mbp of an interval at 27,178-27,218 kbp; or (iv) a chromosomal interval located within about 2 Mbp of an interval at 48,340-48,380 kbp of chromosome 19 (SEQ ID NO.: 26).

Each of the intervals described above shows a clustering of markers that co-segregate with Charcoal Rot Drought Complex tolerance. This clustering of markers occurs in relatively small domains on the linkage groups, indicating the presence of one or more QTL in those chromosome regions. QTL intervals were drawn to encompass the markers that co-segregate with tolerance. The intervals are defined by the markers on their termini, where the interval encompasses all the markers that map within the interval as well as the markers that define the termini.

In some cases, an interval can be drawn, where the interval is defined by linkage to a particular marker locus. For example, an interval on Chr. 15 can be defined where any marker that is linked to the marker S29725-001, S29741-001, and/or S29742-001 is a member of that interval. For example, as used here, linkage is defined as any marker that is within 25 cM from S29725-001, S29741-001, and/or S29742-001. In other aspects, an interval on Chr. 15 can be defined where any marker that is linked to the marker S11315-1 and/or S11316-1 is a member of that interval. For example, as used here, linkage is defined as any marker that is within 25 cM from S11315-1 and/or S11316-1.

As described above, an interval (e.g., a chromosome interval or a QTL interval) need not depend on an absolute measure of interval size such as a centimorgans value. An interval can be described by the terminal markers that define the endpoints of the interval, and typically the interval will include the terminal markers that define the extent of the interval. An interval can include any marker localizing within that chromosome domain, whether those markers are currently known or unknown.

In situations where the interval is close to or comprises one end of the linkage group, the interval can be described by one marker, for example the interval on Chr. 15 can be described as including marker S29741-001 and below, or for example the interval on Chr. 15 can be described as including marker S29741-001 and below. In various further aspect, the interval on Chr. 15 can be described as including marker S29725-001 and above. In a further aspect, the interval on Chr. 15 can be described as flanked by and including S29725-001 and S29741-001. In a still further aspect, the interval on Chr. 15 can be described as flanked by and including S29725-001 and S29742-001.

In various aspects, the interval can be described by one marker, for example the interval on Chr. 19 can be described as including marker S11315-1 and above, or for example the interval on Chr. 19 can be described as including marker S11316-1 and below. In a further aspect, the interval on Chr. 19 can be described as flanked by and including S11315-1 and S13116-1.

"Above" and "below" are the terms commonly used in the art to describe the marker's position relative to the distal end (position zero), with above being closer to position zero. The invention provides a variety of means for defining a chromosome interval in references cited herein (e.g., Song, et al., (2004) "A New Integrated Genetic Linkage Map of the Soybean" Theor Appl Genet 109:122-128).

V. Genetic Maps

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL/marker genetic map relationships. However, it is not intended that the invention be limited to any particular mapping populations, use of any particular software, or any particular set of software parameters to determine linkage of a particular marker or chromosome interval with the Charcoal Rot Drought Complex tolerance phenotype. It is well within the ability of one of ordinary skill in the art to extrapolate the novel features described herein to any soybean gene pool or population of interest, and using any particular software and software parameters. Indeed, observations regarding tolerance markers and chromosome intervals in populations in additions to those described herein are readily made using the teaching of the present disclosure.

Any suitable soybean strains can be used to generate mapping data or for marker association studies. A large number of commonly used soybean lines (e.g., commercial varieties) and mapping populations are known in the art. A broad range of mapping populations were used to obtain the results described in Examples.

A variety of commercial software is available for genetic mapping and marker association studies (e.g., QTL mapping). This software includes but is not limited to: Join-Map® (VanOoijen, and Voorrips (2001) "JoinMap 3.0 software for the calculation of genetic linkage maps," Plant Research International, Wageningen, the Netherlands; and, Stam, The Plant Journal 3(5): 739-744 (1993)); MapQTL® (J. W. vanOoijen, "Software for the mapping of quantitative trait loci in experimental populations" Kyazma B. V., Wageningen, Netherlands); MapManager QT (Manly and Olson, Genome 10: 327-334 (1999)); MapManager QTX (Manly, Cudmore and Meer, Mamm. Genome 12: 930-932 (2001)); GeneFlow® and QTLocate™ (GENEFLOW, Inc., Alexandria, Va.); and TASSEL ("Trait Analysis by aSSociation, Evolution, and Linkage" by Edward Buckler, and information about the program can be found on the Buckler Lab web page at the Institute for Genomic Diversity at Cornell University).

"Unified", "consensus" or "integrated" genetic maps have been created that incorporate mapping data from two or more sources, including sources that used different mapping populations and different modes of statistical analysis. The merging of genetic map information increases the marker density on the map, as well as improving map resolution. These improved maps can be advantageously used in marker assisted selection, map-based cloning, provide an improved framework for positioning newly identified molecular markers and aid in the identification of QTL chromosome intervals and clusters of advantageously-linked markers.

In some aspects, a consensus map is derived by simply overlaying one map on top of another. In other aspects, various algorithms, e.g., JoinMap® analysis, allows the combination of genetic mapping data from multiple sources, and reconciles discrepancies between mapping data from the original sources. See, Van Ooijen, and Voorrips (2001) "JoinMap 3.0 software for the calculation of genetic linkage maps," Plant Research International, Wageningen, the Netherlands; and, Stam (1993) "Construction of integrated genetic linkage maps by means of a new computer package: JoinMap," The Plant Journal 3(5):739-744.

Additional integrated maps are known in the art. See, e.g., Cregan, et al., (1999) "An Integrated Genetic Linkage Map of the Soybean Genome", Crop Science 39:1464-1490; the Soybean Consensus Map 4.0 described by Hyten D. L., et al., (2010) "A high density integrated genetic linkage map of soybean and the development of a 1536 universal soy linkage panel for quantitative trait locus mapping." Crop Sci 50: 960-968; and International Application Number PCT/US2004/024919 by Sebastian, filed Jul. 27, 2004, entitled "Soybean Plants Having Superior Agronomic Performance and Methods for their Production".

Song, et al., provides another integrated soybean genetic map that incorporates mapping information from five different mapping populations (Song, et al., (2004) "A New Integrated Genetic Linkage Map of the Soybean," Theor Appl Genet 109:122-128). This integrated map contains approximately 1,800 soybean markers, including SSR and SNP-type markers, as well as EST markers, RFLP markers, AFLP, RAPD, isozyme and classical markers (e.g., seed coat color). The markers that are on this map are known in the art and have been previously characterized. This information is also available at the website for the Soybean Genomics and Improvement Laboratory (SGIL) at the USDA Beltsville Agricultural Research Center (BARC). See, specifically, the description of projects in the Cregan Laboratory on that website.

The soybean integrated linkage map provided in Song, et al., (2004) is based on the principle described by Stam (1993) "Construction of integrated genetic linkage maps by means of a new computer package: JoinMap," The Plant Journal 3(5):739-744; and Van Ooijen and Voorrips (2001) "JoinMap 3.0 software for the calculation of genetic linkage maps," Plant Research International, Wageningen, the Netherlands. Mapping information from five soybean populations was used in the map integration, and also used to place recently identified SSR markers onto the soybean genome. These mapping populations were Minsoy×Noir 1 (MN), Minsoy×Archer (MA), Noir 1×Archer (NA), Clark×Harosoy (CH) and A81-356022×P1468916 (MS). The Join-Map® analysis resulted in a map with 20 linkage groups containing a total of 1849 markers, including 1015 SSRs, 709 RFLPs, 73 RAPDs, 24 classical traits, six AFLPs, ten isozymes and 12 others. Among the mapped SSR markers were 417 previously uncharacterized SSRs.

Initially, LOD scores and pairwise recombination frequencies between markers were calculated. A LOD of 5.0 was used to create groups in the MS, MA, NA populations and LOD 4.0 in the MN and CH populations. The map of each linkage group was then integrated. Recombination values were converted to genetic distances using the Kosambi mapping function.

VI. Linkage Maps

From the present disclosure and widely recognized in the art, it is clear that any genetic marker that has a significant probability of co-segregation with a phenotypic trait of interest (e.g., in the present case, a tolerance or improved tolerance trait) can be used as a marker for that trait. Useful QTL markers identified herein include S29725-001; S29741-001; 529742-001; 511315-1; and 511316-1.

Additional markers linked to the QTL markers can also be used to predict the tolerance or improved tolerance trait in a soybean plant. In other words, any other marker showing less than 50% recombination frequency (separated by a genetic distance less than 50 cM) with a QTL marker of the invention is also a feature of the invention. Any marker that is linked to a QTL marker can also be used advantageously in marker-assisted selection for the particular trait.

Genetic markers that are linked to QTL markers are particularly useful when they are sufficiently proximal (e.g., closely linked) to a given QTL marker so that the genetic marker and the QTL marker display a low recombination frequency. In the present invention, such closely linked markers are a feature of the invention. As defined herein, closely linked markers display a recombination frequency of about 10% or less (the given marker is within 10 cM of the QTL). Put another way, these closely linked loci co-segregate at least 90% of the time. Indeed, the closer a marker is to a QTL marker, the more effective and advantageous that marker becomes as an indicator for the desired trait.

Thus, in other embodiments, closely linked loci such as a QTL marker locus and a second locus display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Similarly, linked markers (including closely linked markers) of the invention can be determined by review of any suitable soybean genetic map. For example, the integrated genetic map described in Song, et al., (2004) also provides a means to identify linked (including closely linked) markers. See, Song, et al., (2004) "A New Integrated Genetic Linkage Map of the Soybean" Theor Appl Genet 109:122-128; see also the website for the Soybean Genomics and Improvement Laboratory (SGIL) at the USDA Beltsville Agricultural Research Center (BARC), and see specifically the description of projects in the Cregan Laboratory on that website. That genetic map incorporates a variety of genetic markers that are known in the art or alternatively are described in that reference. Detailed descriptions of numerous markers, including many of those described in Song, et al., (2004) can be found at the SOYBASE website resource.

It is not intended that the determination of linked or closely linked markers be limited to the use of any particular soybean genetic map. Indeed, a large number of soybean genetic maps are available and are well known to one of skill in the art. Another map that finds use with the invention in this respect is the integrated soybean genetic maps found on the SOYBASE website resource. Alternatively still, the determination of linked and closely linked markers can be made by the generation of an experimental dataset and linkage analysis.

It is not intended that the identification of markers that are linked (e.g., within about 50 cM or within about 10 cM) to the Charcoal Rot Drought Complex tolerance QTL markers identified herein be limited to any particular map or methodology. Indeed, linked markers as defined herein can be determined from any genetic map known in the art (an experimental map or an integrated map), or alternatively, can be determined from any new mapping dataset.

It is noted that lists of linked and closely linked markers may vary between maps and methodologies due to various factors. First, the markers that are placed on any two maps may not be identical, and furthermore, some maps may have a greater marker density than another map. Also, the mapping populations, methodologies and algorithms used to construct genetic maps can differ. One of skill in the art recognizes that one genetic map is not necessarily more or less accurate than another, and furthermore, recognizes that any soybean genetic map can be used to determine markers that are linked and closely linked to the QTL markers of the present invention.

VII. Techniques for Marker Detection

The invention provides molecular markers that have a significant probability of co-segregation with QTL that impart a Charcoal Rot Drought Complex tolerance phenotype. These QTL markers find use in marker assisted selection for desired traits (tolerance or improved tolerance), and also have other uses. It is not intended that the invention be limited to any particular method for the detection of these markers.

Markers corresponding to genetic polymorphisms between members of a population can be detected by numerous methods well-established in the art (e.g., PCR-based sequence specific amplification, restriction fragment length polymorphisms (RFLPs), isozyme markers, allele specific hybridization (ASH), amplified variable sequences of the plant genome, self-sustained sequence replication, simple sequence repeat (SSR), single nucleotide polymorphism (SNP), random amplified polymorphic DNA ("RAPD") or amplified fragment length polymorphisms (AFLP)). In one additional embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) Laboratory Techniques in Biochemistry and Molecular Biology—Hybridization with Nucleic Acid Probes Elsevier, New York; Berger and Kimmel, Guide to Molecular Cloning Techniques, Methods in Enzymology volume 152 Academic Press, Inc., San Diego, Calif. ("Berger"); as well as in Sambrook and Ausubel (herein).

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each cross is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) Handbook of Fluorescent Probes and Research Chemicals Sixth Edition by Molecular Probes, Inc. (Eugene Oreg.); or Haugland (2001) Handbook of Fluorescent Probes and Research Chemicals Eighth Edition by Molecular Probes, Inc. (Eugene Oreg.) (Available on CD ROM).

PCR, RT-PCR and LCR are in particularly broad use as amplification and amplification-detection methods for amplifying nucleic acids of interest (e.g., those comprising marker loci), facilitating detection of the markers. Details regarding the use of these and other amplification methods can be found in any of a variety of standard texts, including, e.g., Sambrook, Ausubel, Berger and Croy, herein. Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR"). See also Ausubel, Sambrook and Berger, above.

In one aspect, real time PCR or LCR is performed on the amplification mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone, et al., (1995) "Molecular beacon probes combined with amplification by NASBA enable homogenous real-time detection of RNA" Nucleic Acids Res 26:2150-2155; Tyagi and Kramer, (1996) "Molecular beacons: probes that fluoresce upon hybridization" Nature Biotechnology 14:303-308; Blok and Kramer, (1997) "Amplifiable hybridization probes containing a molecular switch" Mol Cell Probes 11:187-194; Hsuih, et al., (1997) "Novel, ligation-dependent PCR assay for detection of hepatitis C in serum" J Clin Microbiol 34:501-507; Kostrikis, et al., (1998) "Molecular beacons: spectral genotyping of human alleles" Science 279:1228-1229; Sokol, et al., (1998) "Real time detection of DNA:RNA hybridization in living cells" Proc Natl Acad Sci USA 95:11538-11543; Tyagi, et al., (1998) "Multicolor molecular beacons for allele discrimination" Nature Biotechnology 16:49-53; Bonnet, et al., (1999) "Thermodynamic basis of the chemical specificity of structured DNA probes" Proc Natl Acad Sci USA 96:6171-6176; Fang, et al., (1999) "Designing a novel molecular beacon for surface-immobilized DNA hybridization studies" J Am Chem Soc 121:2921-2922; Marras, et al., (1999) "Multiplex detection of single-nucleotide variation using molecular beacons" Genet Anal Biomol Eng 14:151-156; and Vet, et al., (1999) "Multiplex detection of four pathogenic retroviruses using molecular beacons" Proc Natl Acad Sci USA 96:6394-6399. Additional details regarding MB construction and use is found in the patent literature, e.g., U.S. Pat. No. 5,925,517 (Jul. 20, 1999) to Tyagi, et al., entitled "Detectably labeled dual conformation oligonucleotide probes, assays and kits;" U.S. Pat. No. 6,150,097 (Nov. 21, 2000) to Tyagi, et al., entitled "Nucleic acid detection probes having non-FRET fluorescence quenching and kits and assays including such probes" and U.S. Pat. No. 6,037,130 (Mar. 14, 2000) to Tyagi, et al., entitled "Wavelength-shifting probes and primers and their use in assays and kits."

PCR detection and quantification using dual-labeled fluorogenic oligonucleotide probes, commonly referred to as "TagMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TagMan™ probes are oligonucleotides that have a label and a quencher, where the label is released during amplification by the exonuclease action of the polymerase used in amplification. This provides a real time measure of amplification during synthesis. A variety of TagMan™ reagents are commercially available, e.g., from Applied Biosystems (Division Headquarters in Foster City, Calif.) as well as from a variety of specialty vendors such as Biosearch Technologies (e.g., black hole quencher probes).

Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) RNase H, and (3) a DNA-dependent RNA polymerase (Guatelli, et al., (1990) Proc Natl Acad Sci USA 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos, et al., (1995) Nucleic Acids Res 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants (Becker, et al., (1995) Mol Gen Genet 249:65; and Meksem, et al., (1995) Mol Gen Genet 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are also appropriate.

Isozyme markers can be employed as genetic markers, e.g., to track markers other than the tolerance markers herein, or to track isozyme markers linked to the markers herein. Isozymes are multiple forms of enzymes that differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

As herein, nucleic acid amplification techniques such as PCR and LCR are well known in the art and can be applied to the present invention to amplify and/or detect nucleic acids of interest, such as nucleic acids comprising marker loci. Examples of techniques sufficient to direct persons of skill through such in vitro methods, including the polymerase chain reaction (PCR), the ligase chain reaction (LCR), Qββ-replicase amplification and other RNA polymerase mediated techniques (e.g., NASBA), are found in the references noted above, e.g., Innis, Sambrook, Ausubel, Berger and Croy. Additional details are found in Mullis, et al., (1987) U.S. Pat. No. 4,683,202; Arnheim and Levinson, (Oct. 1, 1990) C&EN 36-47; The Journal Of NIH Research (1991) 3:81-94; Kwoh, et al., (1989) Proc Natl Acad Sci USA 86:1173; Guatelli, et al., (1990) Proc Natl Acad Sci USA 87:1874; Lomeli, et al., (1989) J Clin Chem 35:1826; Landegren, et al., (1988) Science 241:1077-1080; Van Brunt, (1990) Biotechnology 8:291-294; Wu and Wallace, (1989) Gene 4:560; Barringer, et al., (1990) Gene 89:117, and Sooknanan and Malek, (1995) Biotechnology 13:563-564. Improved methods of amplifying large nucleic acids by PCR, which is useful in the context of positional cloning, are further summarized in Cheng, et al., (1994) Nature 369:684, and the references therein, in which PCR amplicons of up to 40 kb are generated.

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers, (1981) Tetrahedron Letts 22(20):1859-1862, e.g., using a commercially available automated synthesizer, e.g., as described in Needham-VanDevanter, et al., (1984) Nucleic Acids Res 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company, The Great American Gene Company, ExpressGen Inc., Operon Technologies Inc. (Alameda, Calif.) and many others. Similarly, PNAs can be custom ordered from any of a variety of sources, such as PeptidoGenic, HTI Bio-Products, Inc., BMA Biomedicals Ltd (U.K.), Bio•Synthesis, Inc., and many others.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as the Basic Local Alignment Search Tool BLAST® (National Library of Medicine), or even simple word processors.

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers".

It will be appreciated that, although many specific examples of primers are provided herein (see, FIG. 2), suitable primers to be used with the invention can be designed using any suitable method. It is not intended that the invention be limited to any particular primer or primer pair. For example, primers can be designed using any suitable software program, such as LASERGENE®.

In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons.

It is not intended that the primers of the invention be limited to generating an amplicon of any particular size. For example, the primers used to amplify the marker loci and alleles herein are not limited to amplifying the entire region of the relevant locus. In some embodiments, marker amplification produces an amplicon at least 20 nucleotides in length, or alternatively, at least 50 nucleotides in length, or alternatively, at least 100 nucleotides in length, or alternatively, at least 200 nucleotides in length.

VIII. Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly soybean plants, that are tolerant, exhibit improved tolerance or are susceptible to Charcoal Rot Drought Complex by identifying plants having a specified allele at one of those loci, e.g., S29725-001; S29741-001; 529742-001; 511315-1; and 511316-1.

Similarly, by identifying plants lacking the desired marker locus, susceptible or less tolerant plants can be identified, and, e.g., eliminated from subsequent crosses. Similarly, these marker loci can be introgressed into any desired genomic background, germplasm, plant, line, variety, etc., as part of an overall MAS breeding program designed to enhance soybean yield.

The invention also provides chromosome QTL intervals that find equal use in MAS to select plants that demonstrate Charcoal Rot Drought Complex tolerance or improved tolerance. Similarly, the QTL intervals can also be used to counter-select plants that are susceptible or have reduced tolerance to Charcoal Rot Drought Complex. Any marker that maps within the QTL interval (including the termini of the intervals) finds use with the invention. These intervals include: ((i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19. In a further aspect, the interval on Chr. 15 can be described as flanked by and including S29725-001 and S29741-001. Alternatively, these intervals can be specified as follows: (i) a chromosomal interval located within about 2 Mbp of an interval at 7,975-8,015 kpb of chromosome 5; (ii) a chromosomal interval located within about 2 Mbp of an interval at 3,202-3,212 kbp of chromosome 15 (SEQ ID NO.: 25); (iii) a chromosomal interval located within about 2 Mbp of an interval at 27,178-27,218 kbp; or (iv) a chromosomal interval located within about 2 Mbp of an interval at 48,340-48,380 kbp of chromosome 19 (SEQ ID NO.: 26). In a still further aspect, the interval on Chr. 15 can be described as flanked by and including S29725-001 and S29742-001. In a further aspect, the interval on Chr. 19 can be described as flanked by and including S11315-1 and S13116-1.

In general, MAS uses polymorphic markers that have been identified as having a significant likelihood of co-segregation with a tolerance trait. Such markers are presumed to map near a gene or genes that give the plant its tolerance phenotype, and are considered indicators for the desired trait, and are termed QTL markers. Plants are tested for the presence of a desired allele in the QTL marker. The most preferred markers (or marker alleles) are those that have the strongest association with the tolerance trait.

Linkage analysis is used to determine which polymorphic marker allele demonstrates a statistical likelihood of co-segregation with the tolerance phenotype (thus, a "tolerance marker allele"). Following identification of a marker allele for co-segregation with the tolerance phenotype, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is unknown. Tissue samples can be taken, for example, from the first leaf of the plant and screened with the appropriate molecular marker, and it is rapidly determined which progeny will advance. Linked markers also remove the impact of environmental factors that can often influence phenotypic expression.

A polymorphic QTL marker locus can be used to select plants that contain the marker allele (or alleles) that correlate with the desired tolerance phenotype. In brief, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. A variety of procedures for detecting markers are described herein, e.g., in the section entitled "TECHNIQUES FOR MARKER DETECTION." After the presence (or absence) of a particular marker allele in the biological sample is verified, the plant is selected, e.g., used to make progeny plants by selective breeding.

Soybean plant breeders desire combinations of tolerance loci with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein, when genetically-linked to tolerance loci, provide an effective method for selecting resistant varieties in breeding programs. For example, one advantage of marker-assisted selection over field evaluations for tolerance resistance is that MAS can be done at any time of year, regardless of the growing season. Moreover, environmental effects are largely irrelevant to marker-assisted selection.

When a population is segregating for multiple loci affecting one or multiple traits, e.g., multiple loci involved in tolerance, or multiple loci each involved in tolerance or resistance to different diseases, the efficiency of MAS compared to phenotypic screening becomes even greater, because all of the loci can be evaluated in the lab together from a single sample of DNA. In the present instance, include: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19; and these intervals can be assayed simultaneously or sequentially from a single sample or a population of samples. Alternatively, these intervals can be specified as follows: (i) a chromosomal interval located within about 2 Mbp of an interval at 7,975-8,015 kpb of chromosome 5; (ii) a chromosomal interval located within about 2 Mbp of an interval at 3,202-3,212 kbp of chromosome 15 (SEQ ID NO.: 25); (iii) a chromosomal interval located within about 2 Mbp of an interval at 27,178-27,218 kbp; or (iv) a chromosomal interval located within about 2 Mbp of an interval at 48,340-48,380 kbp of chromosome 19 (SEQ ID NO.: 26).

In a further aspect, the interval on Chr. 15 can be described as flanked by and including S29725-001 and S29741-001. In a still further aspect, the interval on Chr. 15 can be described as flanked by and including S29725-001 and S29742-001. In a further aspect, the interval on Chr. 19 can be described as flanked by and including S11315-1 and S13116-1.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding soybean line). The more cycles of backcrossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait such as tolerance to Charcoal Rot Drought Complex.

IX. Introgression of Favorable Alleles

One application of MAS, in the context of the present invention is to use the tolerance or improved tolerance markers to increase the efficiency of an introgression or backcrossing effort aimed at introducing a tolerance QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

Thus, the markers and methods of the present invention can be utilized to guide marker assisted selection or breeding of soybean varieties with the desired complement (set) of allelic forms of chromosome segments associated with superior agronomic performance (tolerance, along with any other available markers for yield, disease resistance, etc.). Any of the disclosed marker alleles can be introduced into a soybean line via introgression, by traditional breeding (or introduced via transformation, or both) to yield a soybean plant with superior agronomic performance. The number of alleles associated with tolerance that can be introduced or be present in a soybean plant of the present invention ranges from 1 to the number of alleles disclosed herein, each integer of which is incorporated herein as if explicitly recited.

The present invention also extends to a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant of the present invention in that it comprises at least one of the allelic forms of the markers of the present invention, such that the progeny are capable of inheriting the allele.

Often, a method of the present invention is applied to at least one related soybean plant such as from progenitor or descendant lines in the subject soybean plant's pedigree such that inheritance of the desired tolerance allele can be traced. The number of generations separating the soybean plants being subject to the methods of the present invention will generally be from 1 to 20, commonly 1 to 5, and typically 1, 2 or 3 generations of separation, and quite often a direct descendant or parent of the soybean plant will be subject to the method (i.e., one generation of separation).

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present invention can be used for MAS in crosses involving elite x exotic soybean lines by subjecting the segregating progeny to MAS to maintain major yield alleles, along with the tolerance marker alleles herein.

X. Generation of Transgenic Cells and Plants

The present invention also relates to host cells and organisms which are transformed with nucleic acids corresponding to tolerance QTL identified according to the invention. For example, such nucleic acids include chromosome intervals (e.g., genomic fragments) that encode a tolerance or improved tolerance trait.

General texts which describe molecular biological techniques for the cloning and manipulation of nucleic acids and production of encoded polypeptides include Berger, Sambrook, and Ausubel, herein. These texts describe mutagenesis, the use of vectors, promoters and many other relevant topics related to, e.g., the generation of clones that comprise nucleic acids of interest, e.g., marker loci, marker probes, QTL that segregate with marker loci, etc.

Host cells are genetically engineered (e.g., transduced, transfected, transformed, etc.) with the vectors of this invention which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells or plant protoplasts by a variety of standard methods known in the art, including but not limited to electroporation (Fromm, et al., (1985) Proc Natl Acad Sci USA 82:5824), infection by viral vectors such as cauliflower mosaic virus (CaMV) (Hohn, et al., (1982) Molecular Biology of Plant Tumors Academic Press, New York, pp. 549-560; Howell, U.S. Pat. No. 4,407,956), high velocity ballistic penetration by small particles with the nucleic acid either within the matrix of small beads or particles, or on the surface (Klein, et al., (1987) Nature 327:70), use of pollen as vector (WO85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch, et al., (1984) Science 233:496; Fraley, et al., (1983) Proc Natl Acad Sci USA 80:4803). Additional details regarding nucleic acid introduction methods are found in Sambrook, Berger and Ausubel, supra. The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, supra, plant regeneration from cultured protoplasts is described in Evans, et al., (1983) "Protoplast Isolation and Culture," Handbook of Plant Cell Cultures 1:124-176 (MacMillan Publishing Co., New York; Davey, (1983) "Recent Developments in the Culture and Regeneration of Plant Protoplasts," Protoplasts, pp. 12-29, (Birkhauser, Base 1); Dale, (1983) "Protoplast Culture and Plant Regeneration of Cereals and Other Recalcitrant Crops," Protoplasts pp. 31-41, (Birkhauser, Base 1); Binding (1985) "Regeneration of Plants," Plant Protoplasts, pp. 21-73, (CRC Press, Boca Raton, Fla.). Additional details regarding plant cell culture and regeneration include Payne, et al., (1992) Plant Cell and Tissue Culture in Liquid Systems John Wiley & Sons, Inc. New York, N.Y.; Gamborg and Phillips, (eds) (1995) Plant Cell, Tissue and Organ Culture; Fundamental Methods Springer Lab Manual, Springer-Verlag (Berlin Heidelberg New York) and Plant Molecular Biology (1993) Croy, Ed.

Bios Scientific Publishers, Oxford, U.K. ISBN 0 12 198370 6. Cell culture media in general are also set forth in Atlas and Parks, (eds) The Handbook of Microbiological Media (1993) CRC Press, Boca Raton, Fla. Additional information for cell culture is found in available commercial literature such as the Life Science Research Cell Culture Catalogue (1998) from Sigma-Aldrich, Inc (St Louis, Mo.) ("Sigma-LSRCCC") and, e.g., the Plant Culture Catalogue and supplement (e.g., 1997 or later) also from Sigma-Aldrich, Inc (St Louis, Mo.) ("Sigma-PCCS").

The present invention also relates to the production of transgenic organisms, which may be bacteria, yeast, fungi, animals or plants, transduced with the nucleic acids of the invention (e.g., nucleic acids comprising the marker loci and/or QTL noted herein). A thorough discussion of techniques relevant to bacteria, unicellular eukaryotes and cell culture is found in references enumerated herein and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QlAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith, (1979) Gene 8:81; Roberts, et al., (1987) Nature 328:731; Schneider, et al., (1995) Protein Expr Purif 6435:10; Ausubel, Sambrook, Berger (all supra). A catalogue of Bacteria and Bacteriophages useful for cloning is provided, e.g., by the ATCC, e.g., The ATCC Catalogue of Bacteria and Bacteriophaqe (1992) Gherna, et al., (eds) published by the ATCC. Additional basic procedures for sequencing, cloning and other aspects of molecular biology and underlying theoretical considerations are also found in Watson, et al., (1992) Recombinant DNA, Second Edition, Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

Techniques for transforming plant cells with nucleic acids are widely available and can be readily adapted to the invention. In addition to Berger, Ausubel and Sambrook, all supra, useful general references for plant cell cloning, culture and regeneration include Jones, (ed) (1995) Plant Gene Transfer and Expression Protocols—Methods in Molecular Biology, Volume 49 Humana Press Towata N.J.; Payne, et al., (1992) Plant Cell and Tissue Culture in Liquid Systems John Wiley & Sons, Inc. New York, N.Y. (Payne); and Gamborg and Phillips, (eds) (1995) Plant Cell, Tissue and Organ Culture; Fundamental Methods Springer Lab Manual, Springer-Verlag (Berlin Heidelberg New York) (Gamborg). A variety of cell culture media are described in Atlas and Parks, (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in Croy, (ed.) (1993) Plant Molecular Biology, Bios Scientific Publishers, Oxford, U.K.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Techniques for transforming a wide variety of higher plant species are also well known and described in widely available technical, scientific, and patent literature. See, for example, Weissinger, et al., (1988) Ann Rev Genet 22:421-477. The DNA constructs of the invention, for example plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones, (ed) (1995) Plant Gene Transfer and Expression Protocols—Methods in Molecular Biology, Volume 49 Humana Press, Towata, N.J., as well as in the other references noted herein and available in the literature.

For example, the introduction of DNA constructs using polyethylene glycol precipitation is described in Paszkowski, et al., (1984) EMBO J 3:2717. Electroporation techniques are described in Fromm, et al., (1985) Proc Natl Acad Sci USA 82:5824. Ballistic transformation techniques are described in Klein, et al., (1987) Nature 327:70-73. Additional details are found in Jones, (1995) and Gamborg and Phillips, (1995), supra, and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example, Horsch, et al., (1984) Science 233:496; and Fraley, et al., (1984) Proc Natl Acad Sci USA 80:4803 and recently reviewed in Hansen and Chilton, (1998) Current Topics in Microbiology 240:22; and Das, (1998) Subcellular Biochemistry 29: Plant Microbe Interactions, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller, (1987) In: Genetic Engineering, vol. 6, P W J Rigby, Ed., London, Academic Press; and Lichtenstein and Draper (1985) In: DNA Cloning, Vol. II, Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman, et al., (1984) Plant Cell Physiol 25:1353), (3) the vortexing method (see, e.g., Kindle, (1990) Proc Natl Acad Sci USA 87:1228.

DNA can also be introduced into plants by direct DNA transfer into pollen as described by Zhou, et al., (1983) Methods in Enzymology 101:433; Hess, (1987) Intern Rev Cytol 107:367; Luo, et al., (1988) Plant Mol Biol Rep 6:165. Expression of polypeptide coding genes can be obtained by injection of the DNA into reproductive organs of a plant as described by Pena, et al., (1987) Nature 325:274. DNA can also be injected directly into the cells of immature embryos and the desiccated embryos rehydrated as described by Neuhaus, et al., (1987) Theor Appl Genet 75:30; and Benbrook, et al., (1986) in Proceedings Bio Expo Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne, et al., (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York); Evans, et al., (1983) Protoplasts Isolation and Culture, Handbook of Plant Cell Culture pp. 124-176, Macmillian Publishing Company, New York; and Binding (1985) Regeneration of Plants, Plant Protoplasts pp. 21-73, CRC Press, Boca Raton. Regeneration can also be obtained from plant callus, explants, somatic embryos (Dandekar, et al., (1989) J Tissue Cult Meth 12:145; McGranahan, et al., (1990) Plant Cell Rep 8:512) organs, or parts thereof. Such regeneration techniques are described generally in Klee, et al., (1987) Ann Rev Plant Phys 38:467-486. Additional details are found in Payne, (1992) and Jones (1995), both supra, and Weissbach and Weissbach, eds. (1988) Methods for Plant Molecular Biology Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing QTLs according to the methods of the invention.

In addition, the regeneration of plants containing nucleic acids of the present invention and introduced by *Agrobacterium* into cells of leaf explants can be achieved as described by Horsch, et al., (1985) Science 227:1229-1231. In this procedure, transformants are grown in the presence of a selection agent and in a medium that induces the regeneration of shoots in the plant species being transformed as described by Fraley, et al., (1983) Proc Natl Acad Sci USA 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

It is not intended that plant transformation and expression of polypeptides that provide disease tolerance, as provided by the present invention, be limited to soybean species. Indeed, it is contemplated that the polypeptides that provide the desired tolerance in soybean can also provide such tolerance when transformed and expressed in other agronomically and horticulturally important species. Such species include primarily dicots, e.g., of the families: Leguminosae (including pea, beans, lentil, peanut, yam bean, cowpeas, velvet beans, soybean, clover, alfalfa, lupine, vetch, lotus, sweet clover, wisteria and sweetpea); and Compositae (the largest family of vascular plants, including at least 1,000 genera, including important commercial crops such as sunflower).

Additionally, preferred targets for modification with the nucleic acids of the invention, as well as those specified above, plants from the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna* and many others.

Common crop plants which are targets of the present invention include soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant and tomato.

In construction of recombinant expression cassettes of the invention, which include, for example, helper plasmids comprising virulence functions, and plasmids or viruses comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of nucleic acids of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds or flowers.

Any of a number of promoters which direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella, et al., (1983) Nature 303: 209. Viral promoters include the 35S and 19S RNA promoters of cauliflower mosaic virus. See, Odell, et al., (1985) Nature 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) EMBO J 7:3315. Many other promoters are in current use and can be coupled to an exogenous DNA sequence to direct expression.

If expression of a polypeptide from a cDNA is desired, a polyadenylation region at the 3'-end of the coding region is typically included. The polyadenylation region can be derived from the natural gene, from a variety of other plant genes, or from, e.g., T-DNA.

A vector comprising sequences of the invention will typically include a nucleic acid subsequence, a marker gene which confers a selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorosulforon, or phosphinothricin (the active ingredient in the herbicides bialaphos or Basta). See, e.g., Padgette, et al., (1996) In: Herbicide-Resistant Crops (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil, (1996) In: Herbicide-Resistant Crops (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic or introgressed plants comprising nucleic acids of the present invention can be screened for transmission of the nucleic acid of the present invention by, for example, standard nucleic acid detection methods or by immunoblot protocols.

A preferred embodiment of the invention is a transgenic plant that is homozygous for the added heterologous nucleic acid; e.g., a transgenic plant that contains two added nucleic acid sequence copies. A homozygous transgenic plant can be obtained by sexually mating (self-fertilizing) a heterozygous transgenic plant that contains a single added heterologous nucleic acid. Back-crossing to a parental plant and out-crossing with a non-transgenic plant can be used to introgress the heterologous nucleic acid into a selected background (e.g., an elite or exotic soybean line).

XI. Methods for Charcoal Rot Drought Complex Tolerant Soybean Plants

Experienced plant breeders can recognize tolerant soybean plants in the field, and can select the tolerant individuals or populations for breeding purposes or for propagation. In this context, the plant breeder recognizes "tolerant" and "non-tolerant" or "susceptible", soybean plants.

Such plant breeding practitioners will appreciate that plant tolerance is a phenotypic spectrum consisting of extremes in tolerance, susceptibility and a continuum of intermediate tolerance phenotypes. Tolerance also varies due to environmental effects and the severity of pathogen infection. Evaluation of phenotypes using reproducible assays and tolerance scoring methods are of value to scientists who seek to identify genetic loci that impart tolerance, conduct marker assisted selection for tolerant populations, and for introgression techniques to breed a tolerance trait into an elite soybean line, for example.

In contrast to fortuitous field observations that classify plants as either "tolerant" or "susceptible", various systems are known for scoring the degree of plant tolerance or susceptibility. These techniques can be applied to different fields at different times, and provide approximate tolerance scores that can be used to characterize a given strain regardless of growth conditions or location.

Ratings are assigned by evaluating all plants of a cultivar in a 2 row by 15 foot plot. Cultivar scores are based on a 1 to 9 system where a score of 9=no disease symptoms with normal plant growth; 8=very slight symptoms including up to a 10% reduction in leaflet and overall canopy size with no wilting; 7=wilting beginning to appear at the uppermost two nodes; 6=wilting at the uppermost three nodes and leaflet yellowing beginning appear; 5=Up to 5% plant death with wilting and yellowing of leaflets occurring at the uppermost four nodes; 4=Up to 10% plant death with wilting and yellowing of leaflets occurring at the uppermost four nodes; 3=Up to 25% plant death with wilting and yellowing of leaflets occurring at the uppermost four nodes; 2=up to 50% plant death; 1=50-100% plant death.

XII. Automated Detection/Correlation Systems of the Invention

In some embodiments, the present invention includes an automated system for detecting markers of the invention and/or correlating the markers with a desired phenotype (e.g., tolerance). Thus, a typical system can include a set of marker probes or primers configured to detect at least one favorable allele of one or more marker locus associated with tolerance or improved tolerance to Charcoal Rot Drought Complex. These probes or primers are configured to detect the marker alleles noted in the tables and examples herein, e.g., using any available allele detection format, e.g., solid or liquid phase array based detection, microfluidic-based sample detection, etc.

For example, in one embodiment, the marker locus is S29725-001; S29741-001; S29742-001; S11315-1; and S11316-1, or any combination thereof, as well as any of the chromosome intervals such as: (i) a chromosomal interval located at about 5 cM to about 26 cM of chromosome 15; (ii) a chromosomal interval located at about 81 cM to about 102 cM of chromosome 19; (iii) the interval on Chr. 15 flanked by and including S29725-001 and S29741-001; or (iv) the interval on Chr. 19 flanked by and including S11315-1 and S13116-1.

For example, in an alternative embodiment, the marker locus is a locus in any of the chromosome intervals such as: (i) a chromosomal interval located at about 17 cM to about 38 cM of chromosome 5; (ii) a chromosomal interval located at about 5 cM to about 26 cM of chromosome 15; (iii) a chromosomal interval located at about 19 cM to about 40 cM of chromosome 19; or (iv) a chromosomal interval located at about 81 cM to about 102 cM of chromosome 19. In a further alternative embodiment, the marker locus is a locus in any of the chromosome intervals such as: (i) a chromosomal interval located within about 2 Mbp of an interval at 7,975-8,015kpb of chromosome 5; (ii) a chromosomal interval located within about 2 Mbp of an interval at 3,202-3,212 kbp of chromosome 15 (SEQ ID NO.: 25); (iii) a chromosomal interval located within about 2 Mbp of an interval at 27,178-27,218 kbp; or (iv) a chromosomal interval located within about 2 Mbp of an interval at 48,340-48,380kbp of chromosome 19 (SEQ ID NO.: 26).

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scanns, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector embodiments include light (e.g., fluorescence) detectors or radioactivity detectors. For example, detection of a light emission (e.g., a fluorescence emission) or other probe label is indicative of the presence or absence of a marker allele. Fluorescent detection is especially preferred and is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele.

The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also a feature of the invention. For example, the instructions can include at least one look-up table that includes a correlation between the presence or absence of the favorable alleles and the predicted tolerance or improved tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical embodiment, the system instructions include at least one look-up table that includes a correlation between the presence or absence of the favorable alleles and predicted tolerance or improved tolerance. The instructions also typically include instructions providing a user interface with the system, e.g., to permit a user to view results of a sample analysis and to input parameters into the system.

The system typically includes components for storing or transmitting computer readable data representing or designating the alleles detected by the methods of the present invention, e.g., in an automated system. The computer readable media can include cache, main, and storage memory and/or other electronic data storage components (hard drives, floppy drives, storage drives, etc.) for storage of computer code. Data representing alleles detected by the method of the present invention can also be electronically, optically, or magnetically transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" in the context of this invention refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program", by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g., C/C++ programs for computing, Delphi and/or Java programs for GUI interfaces, and productivity tools (e.g., Microsoft Excel and/or Sigma-Plot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems of the invention.

For example, tolerance marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase) suitable for recording data in a computer readable medium is acceptable as a database in the context of the present invention. Data regarding genotype for one or more molecular markers, e.g., ASH, SSR, RFLP, RAPD, AFLP, SNP, isozyme markers or other markers as described herein, are similarly recorded in a computer accessible database. Optionally, marker data is obtained using an integrated system that automates one or more aspects of the assay(s) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like (for, e.g., selecting files, retrieving data, reviewing tables of maker information), and an output device (e.g., a monitor, a printer) for viewing or recovering the product of the statistical analysis.

Thus, in one aspect, the invention provides an integrated system comprising a computer or computer readable medium comprising a set of files and/or a database with at least one data set that corresponds to the marker alleles herein. The system also includes a user interface allowing a user to selectively view one or more of these databases. In addition, standard text manipulation software such as word processing software (e.g., Microsoft Word™ or Corel WordPerfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent Technologies (Palo Alto, Calif.).

Systems for molecular marker analysis of the present invention can, thus, include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype (s) for particular markers or alleles, e.g., to facilitate marker assisted selection of soybean plants with favorable allelic forms of chromosome segments involved in agronomic performance (e.g., tolerance or improved tolerance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS 95™ based machines), MACINTOSH™, LINUX, or UNIX based (e.g., SUN™ work station) computers.

XIII. Methods to Screen Plants for Resistance to a Plant Pathogen

In some embodiments, the present invention includes methods for screening a plant for tolerance to a plant pathogen, the method comprising: (a) providing at least one inoculation probe having a pointed end to a container of agar inoculated with a pathogen; wherein a surface of the inoculation probe is contact with the surface of the agar in the petri dish; (b) inoculating a plant, after a predetermined contact time between at least one inoculation probe and the pathogen, by inserting the pointed end of at least one inoculation probe, comprising pathogen on the surface thereof, into a site located on a plant stem; and (c) assessing plant tolerance to the pathogen at a predetermined time. The method is significantly better at phenotyping for resistance or sensitivity to a plant pathogen. Thus, the disclosed new method enables reliable phenotyping in the growth chamber that more accurately matches field based results.

For example, as disclosed herein, this method when used for screening plant resistance to charcoal rot tolerance provides results that match with field observations. The results obtained using the disclosed method are superior to other methods for screening for resistance to charcoal rot, including, for example, the previously described standard of Twizeyimana et al., (Plant Disease (2012) 96(8):1210-1215). Without wishing to be bound by a particular theory, it is believed that the disclosed method for screening provides for superior results, in part, because the pathogen grows in intimate contact with the inoculation probe and that the inoculation probe is made of a material suitable for pathogen growth. In various aspects, without wishing to be bound by a particular theory, it is believed that the disclosed method permits more efficient transfer of pathogen to the plant.

In various aspects, the pathogen is a *Macophomina phaseolina* isolate. In a further aspect, the plant is *Glycine max*. In a still further aspect, the pathogen is a *Macophomina phaseolina* isolate; and the plant is *Glycine max*.

In various aspects, the pathogen is a *Macophomina phaseolina* isolate; the plant is *Glycine max*; and the agar is potato dextrose agar. In a further aspect, the pathogen is a *Macophomina phaseolina* isolate; the plant is *Glycine max*;

and the pathogen is grown in contact with the at least one inoculation probe is 7-9 days. In a still further aspect, the pathogen is a *Macophomina phaseolina* isolate; the plant is *Glycine max*; and the located on the plant stem about 0.1 to 1.5 cm above cotyledons of the plant. In a yet further aspect, the pathogen is a *Macophomina phaseolina* isolate; the plant is *Glycine max*; and the site located on the plant stem is sealed following insertion of the pointed end of at least one inoculation probe. In an even further aspect, the pathogen is a *Macophomina phaseolina* isolate; the plant is *Glycine max*; and the site located on the plant stem is sealed with petroleum jelly following insertion of the pointed end of at least one inoculation probe. In a still further aspect, the pathogen is a *Macophomina phaseolina* isolate; the plant is *Glycine max*; and the plant tolerance is assessed at 14-21 days after inoculation of the plant.

In various aspects, the present invention includes methods for screening a *Glycine max* plant for tolerance to *Macophomina phaseolina*, the method comprising: (a) providing at least one inoculation probe having a pointed end to a container of agar inoculated with *Macophomina phaseolina*; wherein a surface of the inoculation probe is contact with the surface of the agar in the petri dish; (b) inoculating a plant, after contact time 5-15 days between at least one inoculation probe and the pathogen, by inserting the pointed end of at least one inoculation probe, comprising pathogen on the surface thereof, into a site located on the plant stem about 0.1 to 1.5 cm above cotyledons of the *Glycine max* plant; and (c) assessing *Glycine max* plant tolerance to *Macophomina phaseolina* at 14-21 days after inoculation of the plant. The method is significantly better at phenotyping for resistance or sensitivity to a plant pathogen. Thus, the disclosed new method enables reliable phenotyping in the growth chamber that more accurately matches field based results.

The shape, size, and material of inoculation probe can be varied as deemed appropriate by the skilled artisan. The inoculation probe should be of size and shape that allows it to be inserted into the plant that is to be inoculated. The material from which the inoculation probe is made or fabricated should be a material that permits growth of the pathogen on the inoculation probe when it is incontact with agar in a petri dish. In a further aspect, the inoculation probe is sterilized prior to use. Sterilization of the probe prior to use can be by any method that allows sterilization of the inoculation probe without comprising the structure of the inoculation probe, e.g., autoclaving the sterilization probe. In a still further aspect, the inoculation probe is about 0.5-1.5 cm in length and about 0.01-0.1 cm in width. In a yet further aspect, the inoculation probe is cylindrical in shape; wherein the diameter of the cylinder is about 0.01-0.1 cm; wherein the cylinder is about 0.5-1.5 cm in length; and wherein one end of the cylinder forms the point of the inoculation probe. In various aspects, the inoculation probe is solid and/or without an open end. In a further aspect, the inoculation probe is not hollow or an open tube. A key aspect of the inoculation probe is that one end of it is pointed and allows for insertion into the plant to be inoculated. In a further aspect, the inoculation probe is made of a material suitable for pathogen growth or adherence, e.g. wood.

In various aspects, the inoculation probe is fabricated from a wooden toothpick, wherein about 0.5-1.5 cm is removed from one end of the toothpick and leaving intact a pointed end, thereby forming a pointed inoculation probe about 0.5-1.5 in length with a pointed end.

In a further aspect, the number of inoculation probes placed on the surface of agar in the petri dish is of a density such that at least a portion of the surface of the inoculation probe is in contact with the agar surface. For example, when inoculation probes are prepared from wooden toothpicks as described herein above, it is desirable to evenly distribute about 70 to about 110 such inoculation probes on the agar surface of a petri dish with about a 100 mm diameter.

The skilled artisan may seal the insertion following inoculation of the plant. Various materials can be used to seal the insertion site, including, but not limited to, petroleum jelly and the like.

EXAMPLES

Example 1

Growth Chamber Screening Method

Plants were grown in 10.1 cm$^2$ plastic pots (W.H. Milikowski, Inc.) in Metro Mix 900 potting soil (Sun Gro Horticulture Inc.). Six pots (replicates) were planted of each soybean entry, with 5 seeds planted per pot. Seedlings were grown out for 8 days prior to inoculation. During this period, seedlings were maintained in a growth chamber at 26.7° C. with a 16 hour photoperiod (ppd) under metal halide lighting. Plants were watered for optimal seed germination and health. On the ninth day following planting (unifoliate growth stage), plants were inoculated.

All plants were inoculated with microsclerotia of *Macrophomina phaseolina* (causal agent of charcoal rot) isolate MP3, collected in May 2008 from Champaign County, Ill. The isolate was maintained on Microbank cryopreservation beads (Pro-Lab Diagnostics) at −80° C. and re-isolated periodically from infected plants to maintain isolate virulence. To prepare for inoculum production, *M. phaseolina* infested microbeads were removed from cold storage and grown on full-strength potato dextrose agar (PDA; 39 grams potato dextrose agar/liter water) at 23° C. for 3 days. An agar plug was excised from the leading edge of the actively growing *M. phaseolina* culture and transferred to a full-strength PDA plate; these plates were incubated at 23° C. for 2 days. Round wooden toothpicks, cut approximately 1 cm from the tip with the tip sections retained, were sterilized by autoclaving at 121° C. Six 3-mm agar plugs were excised from the actively growing edge of the *M. phaseolina* culture plates and evenly distributed on the surface of a 100×25 mm full-strength PDA plate; 80 to 100 sterile toothpick tips were distributed over the surface of these PDA plates, which were incubated at 23° C. for nine days, at which point large quantities of black microsclerotia were visible on the surface of the toothpicks.

A new method screening was developed and used in studies described herein. Plants were inoculated by inserting a microsclerotia-infested toothpick, tip first, into the plant stem 5 to 8 mm above the cotyledons. Only three plants were inoculated per pot, for a total of 18 plants per entry. Plants without fully unrolled unifoliate leaves were discarded. The wound at the inoculation site was sealed with petroleum jelly. Inoculated plants were placed in a dew room at 25.6° C. with a 16 hour ppd for 48 hours. During this period, plants were misted at 100 cc/min by an oscillating Aquafog XE-330 Turbo (Jaybird Manufacturing Inc.) humidifier for 30 mins of each daylight hour and 15 mins of each nighttime hour. As discussed herein below, the efficacy of this screening method was compared to a standard, publicly available method (Twizeyimana, M., et al., Plant Disease (2012) 96(8):1210-1215).

After 48 hours, plants were returned to the growth chamber at 25.6° C. and 16 hour ppd until they reached the first trifoliate growth stage, at which time the temperature was raised by 1° C. each day until the temperature reached 29.4° C. Light intensity during the post-inoculation period was 50 percent on the first day, and then increased to 75 percent for the remainder of the experiment. One day after being removed from the dew chamber, pots were placed in a pre-assigned location within the growth chamber in randomized complete block design. Pots were watered daily and staked as needed to maintain plant health. All plants were fertilized 5 to 6 days post-inoculation with 15-5-15 Cal-Mag Excel fertilizer.

Plants were assessed for level of charcoal rot tolerance 14 to 21 days post-inoculation. The scoring date for each experiment was determined based on the observed incidence of dead plants among the susceptible and tolerant check varieties. Plants were scored on a 1 to 9 scale, with 1 representing the most susceptible end of the scale and 9 representing the most tolerant. To assess incidence and severity of internal stem lesions, the stems of all living plants were cut longitudinally from 3 to 5 cm below the point of inoculation to 10 to 15 cm above the point of inoculation. A score of 1 indicates that the plant was heavily infected, completely wilting, dying, or dead. A score of 3 indicates that the plant had a long external and/or internal lesion and was partially wilted. A score of 5 indicates that the plant had an internal lesion greater than 1.3 cm in length with no wilting observed. A score of 7 indicates the presence of an internal lesion of less than 1.3 cm with no wilting. A score of 9 indicates that no charcoal rot symptoms were visible; there may have been a small internal scar visible at the point of inoculation. Plants scoring 5, 7, or 9 typically had no visible external symptoms. Plants with a score of 1 or 3 were considered susceptible. Plants with a score of 5 or 7 were considered moderately tolerant, and plants with a score of 9 were considered highly tolerant.

The three plant scores from each pot were averaged and the score of each pot was adjusted to account for spatial variation using a Best Linear Unbiased Estimation ("BLUE") as previously described (Henderson, C. R. 1975. Best linear unbiased estimation and prediction under a selection model. Biometrics 31:423-447). A single BLUE value was assigned to each entry in the assay. A Best Linear Unbiased Prediction ("BLUP"; ibid) was calculated for each entry to account for experiment effects. The BLUP of each entry was compared to the BLUP of the established controls to determine the entry's level of charcoal rot tolerance.

Example 2

Comparison of Screening Methods

Ten soybean varieties were phenotyped using the public standard method, the claimed new method, and screened in the field for charcoal rot tolerance. Regression analysis was used to compare the two growth chamber screening methods to field based scores (Table 2). The data in Table 2 show regression analysis of the growth chamber results compared to field-collected charcoal rot phenotypes (2-76 repetitions) across 10 plant varieties. Results show that the new method disclosed herein (see Example 1) is significantly better at phenotyping for charcoal rot tolerance that matches with field observations than is the previously described standard method of Twizeyimana et al., (Plant Disease (2012) 96(8): 1210-1215). The disclosed new method enables reliable phenotyping in the growth chamber that more accurately matches field based results.

TABLE 2

| Method | Reps | $R^2$ | p-value |
|---|---|---|---|
| Disclosed New Method | 24 | 0.60 | 0.008 |
| Twizeyimana, et al. | 6-18 | 0.22 | 0.176 |

Example 3

Recombinant Inbred Line (RIL) Data

Two recombinant inbred line (RIL) populations were created by crossing two varieties that contrasted for charcoal rot tolerance. Seed was bulk generation advanced in Puerto Rico four generations and F5 RILs were derived to create the populations. The soybean entries assessed in the charcoal rot laboratory bioassay were 377 recombinant inbred lines (RILs) from population 1 (parent 1×parent 2) screened across 6 experiments, and 354 RILs from population 2 (parent 1×parent 3) screened across 5 experiments. Six replications of each RIL along with a standard set of tolerant, moderately tolerant, and susceptible checks with established charcoal rot tolerance scores were included in the experiments. Table 3 shows the results of QTL mapping within the populations in which a total of 4 unique QTL were identified.

TABLE 3

| P1 | P2 | QTL Peak Marker[†] | QTL Chr. | Physical Position[*] | Genetic Position[**] | LOD | Variance |
|---|---|---|---|---|---|---|---|
| 1 | 2 | S01353-1 | 15 | 3,012,488 | 15.51 | 7.03 | 14% |
| 1 | 3 | S11318-1 | 19 | 48,436,397 | 91.68 | 12 | 11.8 |
| 1 | 3 | S03394-1 | 19 | 27,198,319 | 29.32 | 9.9 | 9.6 |
| 1 | 2 | S04257-1 | 5 | 7,995,435 | 27.82 | 5 | 6% |

[†]Marker nearest to QTL peak.
[*]Physical position (bp) on the Glyma 1 Assembly reference (Schmutz, Jeremy, et al. "Genome sequence of the palaeopolyploid soybean." Nature 463.7278 (2010): 178-183).
[**]Genetic position (cM) on the Soybean Consensus Map 4.0 (Hyten D. L., et al., (2010) Crop Sci 50: 960-968).

Example 4

Near Isogenic Line (NIL) Data

Near isogenic lines (NILs) were created by identifying F3 varieties that were heterozygous across the QTL interval. Individual F3:5 plants within the F3 varieties were derived to create a population that contrasted for the parental haplotypes at the QTL but were near isogenic across the rest of the genome. Individual NILs were phenotyped using the described method at six replications, NIL families are composed of multiple F3 varieties from the same parentage. Table 4 shows results for NIL families of contrasts of 3 of the QTL. This data additionally confirms that the previously identified QTL are indeed operating as expected among different individuals than those in the mapping populations.

TABLE 4

| NIL P1 Haplotype | N P1[†] | NIL P2 Haplotype | N P2[††] | Flanking Markers | | Chr. | NIL Region | p-value | Increase[‡] |
|---|---|---|---|---|---|---|---|---|---|
| 4 | 8 | 8 | 7 | | | | | | |
|   | 9 |   | 6 | S01353-1 | S04330-1 | 15 | 15.52-17.25 | p < 0.01 | 35 |
| 4 | 6 | 9 | 4 | | | | | | |
|   | 9 |   | 4 | S03409-1 | S04330-1 | 15 | 10.1-17.25 | p < 0.05 | 49 |
| 6 | 3 | 5 | 3 | S01481-1 | S01818-1 | 19 | 89.53-94.75 | p = 0.087 | 27 |
| 7 | 5 | 5 | 9 | S01481-1 | S01818-1 | 19 | 89.53-94.75 | p = 0.009 | 42 |
| 4 | 7 | 10 | 7 | | | | 27.93-27.81 | | |
|   | 3 |   | 0 | S04793-1 | S05933-1 | 5 | (misassembly) | p < 0.05 | 50 |

[†]Number of P1 NILs.
[††]Number of P2 NILs.
[‡]% increase for positive haplotype associated with resistance to Charcoal Rot Drought Complex.

Example 5

Regression Analysis of Haplotypes

Two QTL regions were further explored by regression analysis of haplotypes assigned using high density sequence data. A large set of elite breeding germplasm was phenotyped using the described method, these same germplasm were genotyped using high density resequencing at a 0.1× density. The germplasm was classified into 10 kb length haplotypes, 90% similar across the window, across the QTL regions.

FIG. 1 shows the QTL region on chromosome 15 from approximately 3,012 kb to 3,946 kb on the Glyma 1 Assembly reference (Schmutz, Jeremy, et al. "Genome sequence of the palaeopolyploid soybean." Nature 463.7278 (2010): 178-183) using 10 kb haplotype windows created using high density sequence data from 206 unique varieties. The different colors show haplotypes that are different in 10 kb windows along the chromosome. Displayed in columns are three known resistant and three known susceptible varieties, which are indicated respectively by "RES" and "SUS" in the figure. To the right are the results for 10 varieties with unknown QTL status. Regression analysis was employed to determine which haplotype window explained the greatest variation in the phenotypic data across the germplasm set. Indicated next to the last column on the right are regression values ($R^2$) for the effect of the indicated haplotype on charcoal rot drought complex across the set of 206 varieties. It was determined that the region from 3,202 kb-3,212 kb explained the greatest amount of phenotypic variation ($R^2$=16.8%).

Figure 2:
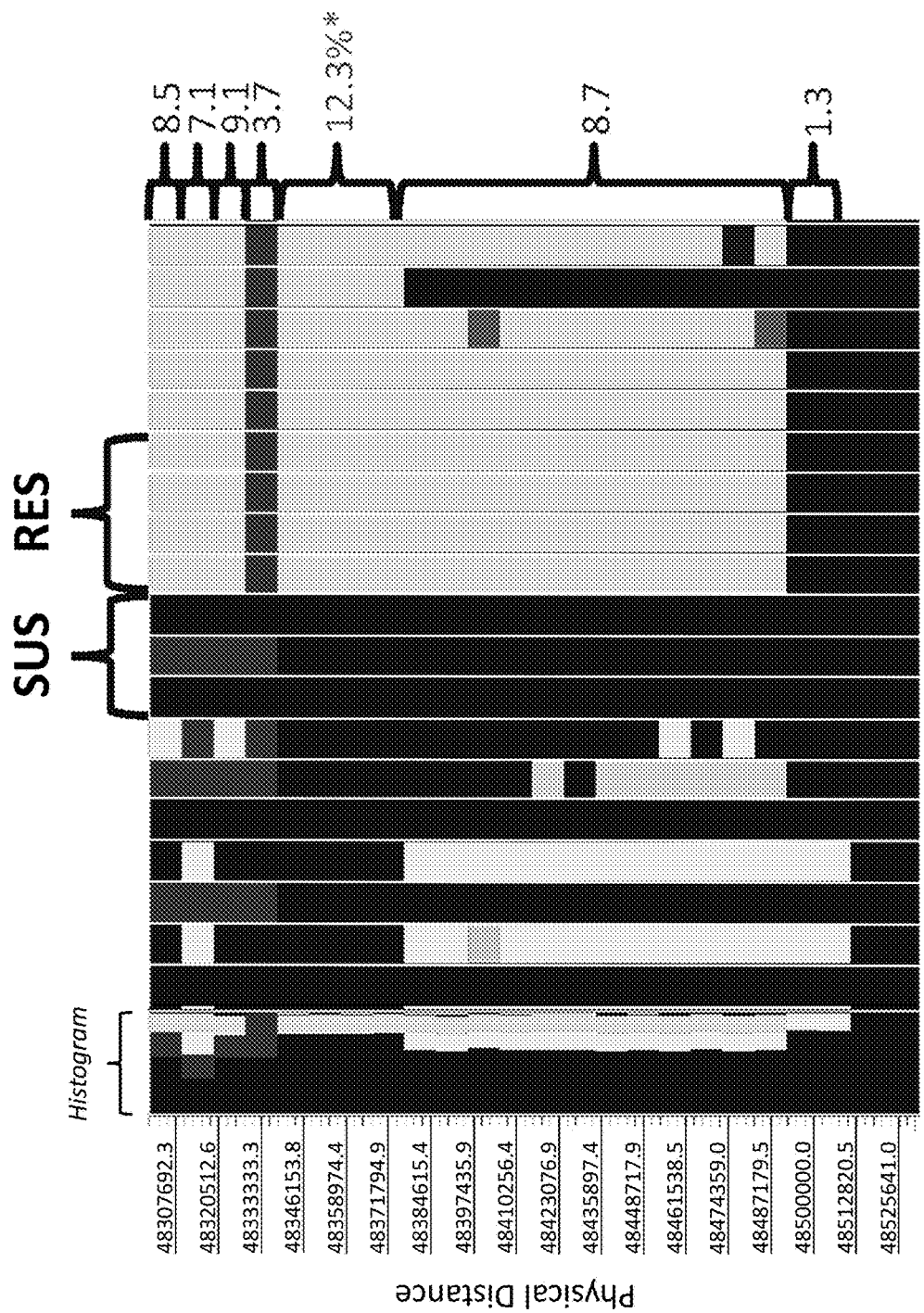
FIG. 2 shows representative data for haplotype analysis of Chromosome 19 in the region of approximately 48,300-48,550 kb on the Soybean Consensus Map 4.0 (Hyten D. L., et al., (2010) Crop Sci 50: 960-968) using 10 kb haplotype windows created using high density sequence data from 148 unique varieties. Displayed in columns are four known resistant and three known susceptible varieties, which are indicated respectively by "RES" and "SUS" in the figure. The figure also shows results for 12 varieties with unknown QTL status. Indicated next to the last column on the right are regression values ($R^2$) for the effect of the indicated haplotype on charcoal rot drought complex across the set of 148 varieties. The left is a histogram (as indicated) representing the cumulative number of haplotypes from the columns to the right for each 10 kb window examined. The scale to the far left indicates the physical distance within the region examined in the columns to the right.

FIG. 2 shows the QTL region on chromosome 19 from approximately 48,300 kb to 48,550 kb on the Glyma 1 Assembly reference (Schmutz, Jeremy, et al. "Genome sequence of the palaeopolyploid soybean." Nature 463.7278 (2010): 178-183) using 10 kb haplotype windows created using high density sequence data from 148 unique varieties. The different colors show haplotypes that are different in 10 kb windows along the chromosome. Displayed in columns are four known resistant and three known susceptible varieties, which are indicated respectively by "RES" and "SUS" in the figure. The figure also shows results for 12 varieties with unknown QTL status. Regression analysis was employed to determine which haplotype window explained the greatest variation in the phenotypic data across the germplasm set. Indicated next to the last column on the right are regression values ($R^2$) for the effect of the indicated haplotype on charcoal rot drought complex across the set of 148 varieties. It was determined that the region from 48,340 kb-48,380 kb explained the greatest amount of phenotypic variation ($R^2$=12.3%).

Charcoal rot phenotypic data obtained using the growth chamber screening method (see Example 1 above) was available on both haplotypes for these two QTL (Chr. 15, 3,202 kb-3,212 kb; and Chr. 19, 48,340 kb-48,380 kb) across 141 elite soybean varieties. When both haplotypes are considered together (Table 5), the data strongly indicate that the effect of these two QTL loci are additive in nature for charcoal rot tolerance. The resistant haplotype class for the Ch 15 QTL significantly increases tolerance by a mean of 1.44 compared to the double susceptible. Adding the resistant haplotype for the Ch 19 QTL increases numerically 0.86 compared to the double susceptible, but the difference is not significant and likely due to the smaller sample size. The double resistant class is significantly higher than either single resistant class and has a 2.59 higher mean (approximately 95% increase) than the double susceptible.

TABLE 5

| | | Ch 19, 48 340 kb-48, 380 kb | |
|---|---|---|---|
| | | RES | SUS |
| Ch 15, 3202 kb-3212 kb | RES | 5.33 (18)[A] | 4.18 (22)[B] |
| | SUS | 3.60 (15)[B,C] | 2.74 (86)[C] |

*Values are mean phenotypic score, N in parenthesis, different letters denote means are significantly different using Fisher's LSD (p < .05)

The disclosed novel phenotyping procedure for the charcoal rot pathogen provides a method to much more accurately phenotype soybean varieties' genetic tolerance. As disclosed herein, the use of this novel phenotyping procedure on two mapping populations lead to the identification of four QTLs that have significant effects on charcoal rot tolerance. Two of these QTLs (Chr. 15, 3,202 kb-3,212 kb; Chr. 19, 48,340 kb-48,380 kb) were further validated using NILs and their effects demonstrated across a large set of breeding germplasm. Additionally the effect of these QTLs has been shown herein to be additive in nature across the same breeding germplasm. These novel QTLs can allow soybean breeders to more efficiently develop soybean varieties with higher levels of tolerance by using marker assisted selection. In addition, the use of these QTLs can permit more accurate phenotyping of soybean varieties.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. A method of breeding a soybean plant tolerant to Charcoal Rot, the method comprising:
   a. isolating nucleic acid or tissue containing nucleic acid from a soybean plant;
   b. detecting in the nucleic acid the presence of one or more markers associated with Charcoal Rot tolerance, wherein the one or more markers are located in a chromosomal interval located between about 48,354,468 and 48,384,426 of chromosome 19, and wherein said chromosomal interval includes a sequence that hybridizes with the S11315-1 marker at position 48,354,468 and/or a sequence that hybridizes with the S11316-1 marker at position 48,384,426;
   c. thereby identifying and/or selecting a Charcoal Rot tolerant soybean plant;
   d. crossing the soybean plant identified and/or selected in step c with a second plant not having said one or more markers in said chromosomal interval;
   e. collecting seeds from said cross; and
   f. growing a progeny soybean plant from said seed which comprises said one or more markers in said chromosomal interval, thereby producing a soybean plant with increased tolerance to Charcoal Rot compared to a soybean plant not comprising said one or more markers in said chromosomal interval.

* * * * *